United States Patent
Atamanyuk et al.

(10) Patent No.: US 9,975,911 B2
(45) Date of Patent: May 22, 2018

(54) ANTIBACTERIAL COMPOUNDS AND BIOLOGICAL APPLICATIONS THEREOF

(71) Applicant: LABORATOIRE BIODIM, Paris (FR)

(72) Inventors: Dmytro Atamanyuk, Chelles (FR); Vincent Gerusz, Paris (FR); Francois Moreau, Orsay (FR); Vivien Henryon, Lyons (FR); Jerome Monbrun, Seyssuel (FR); Etienne Airiau, Vienne (FR)

(73) Assignee: MUTABILIS, Paris (FR)

( * ) Notice: Subject to any disclaimer, the term of this patent is extended or adjusted under 35 U.S.C. 154(b) by 0 days. days.

(21) Appl. No.: 14/438,929

(22) PCT Filed: Oct. 28, 2013

(86) PCT No.: PCT/EP2013/072526
§ 371 (c)(1),
(2) Date: Apr. 28, 2015

(87) PCT Pub. No.: WO2014/067904
PCT Pub. Date: May 8, 2014

(65) Prior Publication Data
US 2015/0291636 A1   Oct. 15, 2015

(30) Foreign Application Priority Data

Oct. 29, 2012 (EP) .................. 12306350

(51) Int. Cl.
*C07F 9/09* (2006.01)
*A61K 31/661* (2006.01)
(Continued)

(52) U.S. Cl.
CPC .............. *C07F 9/09* (2013.01); *A61K 31/661* (2013.01); *A61K 45/06* (2013.01); *C07F 9/091* (2013.01); *C07F 9/38* (2013.01)

(58) Field of Classification Search
None
See application file for complete search history.

(56) References Cited

FOREIGN PATENT DOCUMENTS

WO    2012073214 A2    6/2012

OTHER PUBLICATIONS

Bonnette, Corinne et al. Tet. Lett. 1996, 37(8), 1221-4.*
European Patent Office, PCT International Search Report regarding corresponding PCT Application No. PCT/EP2013/072526 dated Nov. 25, 2013, pp. 1-3.
(Continued)

*Primary Examiner* — Clinton A Brooks
(74) *Attorney, Agent, or Firm* — Duane Morris LLP

(57) ABSTRACT

The invention relates to compounds of formulae (Ia), (Ib) or (Ic) wherein, $A_1$ and $A_2$, identical or different, are H, $(C_1-C_6)$ alkyl, $(C_1-C_6)$ fluoroalkyl, $(C_2-C_6)$ alkenyl, $(C_2-C_6)$ alkynyl, $(C_1-C_6)$ alkyl-$OR_a$, $(C_1-C_6)$ alkyl-$SR_a$, $(C_1-C_6)$ alkyl-$NR_aR_b$, $OR_a$, $SR_a$, $NR_aR_b$, or $COR_a$; $A_3$ is H, OH or form a carbonyl with $A_4$; $A_4$ is H, OH or form a carbonyl with $A_3$; $A_5$ is H, $CR_aR_bOH$, F, OH or forms a double bond with X in the case where X is CH; $A_6$ is H or F; X is $CH_2$, CHF, $CF_2$, CHOH, O, S, $NR_a$ or a simple bond, or X is CH in the case where $A_5$ forms with X a double bond; Y is $P(O)(OR_a)(OR_b)$ or $P(O)(OR_a)(NR_aR_b)$; V is O or S; $A_7$ is H, $(C_1-C_6)$ alkyl, $(C_1-C_6)$ fluoroalkyl, $(C_2-C_6)$ alkenyl, $(C_2-C_6)$ alkynyl or $(C_1-C_6)$ alkyl-$OR_a$; $A_8$ is OH or H, $R_a$ and $R_b$, identical or different, are H, $(C_1-C_6)$ alkyl, $(C_1-C_6)$ fluoroalkyl, $(C_1-C_6)$ alkyl-OH or $(C_1-C_6)$ alkyl-O—$(C_1-C_6)$ alkyl; and their addition salts thereof with acids and bases, their preparation and their use in the antibacterial prevention and therapy, used alone or in association with antibacterials, antivirulence agents or drugs reinforcing the host innate immunity.

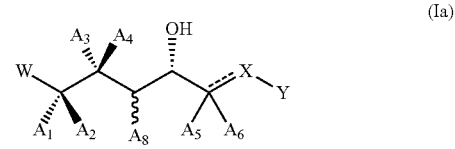

(Ia)

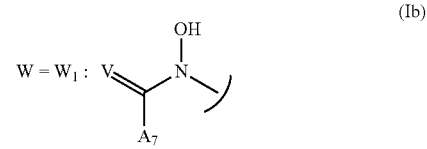

(Ib)

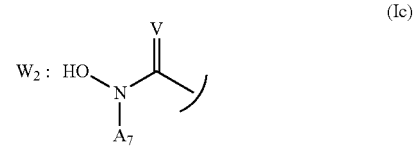

(Ic)

16 Claims, 1 Drawing Sheet

(51) Int. Cl.
*A61K 45/06* (2006.01)
*C07F 9/38* (2006.01)

(56) References Cited

OTHER PUBLICATIONS

Durka, Maxime et al., Systematic Synthesis of Inhibitors of the Two First Enzymes of the Bacterial Heptose Biosynthetic Pathway: Towards Antivirulence Molecules Targeting Lipopolysaccharide Biosynthesis, Chem. Eur. J. 2011, 17, pp. 11305-11313.

* cited by examiner

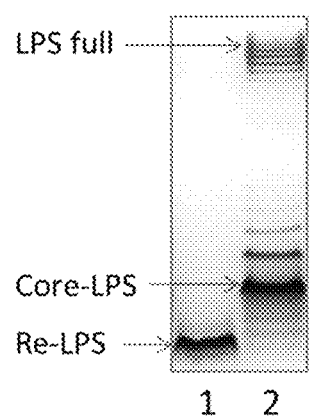

ANTIBACTERIAL COMPOUNDS AND BIOLOGICAL APPLICATIONS THEREOF

CROSS-REFERENCE TO RELATED APPLICATIONS

The present application is a U.S. national phase application filed under 35 U.S.C. § 371 of International Application No. PCT/EP2013/072526, which was filed Oct. 28, 2013 and which claims priority to European Application No. 12306350.5 filed on Oct. 29, 2012, both of which are incorporated herein by reference in their entirety.

The invention relates to new antibacterial compounds, their preparation and intermediates, their use as drugs and pharmaceutical compositions containing them.

The invention relates to new compounds capable of inhibiting bacterial heptose biosynthesis and thereby lowering or suppressing bacterial virulence, as well as their antibacterial pharmaceutical applications in preventive or curative treatment or in combination therapy.

The invention particularly relates to new compounds capable of inhibiting the GmhA enzyme of bacterial heptose synthesis, thereby lowering or suppressing bacterial virulence, as well as their antibacterial pharmaceutical applications.

The lipopolysaccharide (LPS) is a major component of the outer membrane of Gram-negative bacteria. It is composed of three regions: the lipid A, the core oligosaccharide and the O antigen. The core oligosaccharide is divided into the inner core and the outer core. The inner core consists in a motif of five sugars: two Kdo (Kdo: 3-deoxy-D-manno-octulosonic acid) and three successive heptoses. The first heptose transfer is catalysed by the Heptosyltransferase I (protein WaaC) and the second heptose transfer by the Heptosyltransferase II (protein WaaF). The natural donor substrate of these transferases is ADP heptose, which is synthesized in bacteria from sedoheptulose-7-phosphate by the successive enzymatic steps catalyzed by the following enzymes: GmhA, HldE-K (former or other nomenclature: RfaE-K), GmhB, HldE-AT (former or other nomenclature: RfaE-AT) and HldD (former or other nomenclature: RfaD, WaaD) (Journal of Bacteriology, 2002, 184, 363).

Heptose synthetic pathway is conserved among Gram negative bacterial species and is necessary for full LPS synthesis. It has been demonstrated that a complete LPS is necessary for Gram negative bacterial pathogenesis. Bacteria lacking heptoses display a so-called "deep-rough phenotype" due to the absence of the outer core and the O-antigen. While still able to survive as the commensal flora, they are unable to yield a productive infection in the host and are very sensitive to detergents or hydrophobic antibiotics as well as to the bactericidal effect of the host complement (Annu. Rev. Biochem. 2002, 635).

By preventing full LPS development in Gram negative bacteria, inhibitors of bacterial GmhA would be expected to induce a high sensitivity to the host complement and therefore be able to prevent or inhibit bacterial infection.

Such inhibitors would provide a novel way to treat or prevent bloodstream infections caused by pathogenic Gram negative bacteria, without affecting the commensal flora and with less selective pressure than conventional antibacterial agents.

A few inhibitors of bacterial heptose synthesis have been reported in the literature, targeting GmhA (Chem. Eur. J. 2011, 11305; WO2012073214), HldE (Chem. Eur. J. 2011, 11305; Chem. Biol. 2006, 437; WO2006058796; WO2008038136; Bioorg. Med. Chem. 2009, 1276; WO2010001220; WO2012073214) and Waac/Waaf (Bioorg. Med. Chem. Lett. 2008, 4022; Chem. Eur. J. 2008, 9530). However, no precise data on the bacterial inhibition of the LPS biosynthesis have been reported yet for these inhibitors, raising concern on their ability to reach their cytosolic target at an effective concentration. Thus, despite their attractiveness, these bacterial targets are still largely unexploited at this time since there are no drugs on market or on advanced clinical phases. One of the purposes of the present invention is therefore to provide novel compounds active on these targets while also demonstrating the ability to inhibit LPS formation on clinically relevant Gram-negative bacteria.

BRIEF DESCRIPTION OF THE DRAWINGS

FIG. 1 shows an LPS gel electrophoresis analysis performed as described in the Examples. Lane 1 is a sample obtained from an *E. coli* delta-hldE mutant defective for LPS-heptosylation biosynthesis. The delta-hldE mutant synthesizes only Re-LPS, which contains lipid A branched with two Kdo (3-deoxy-D-manno-octulosonic acid) residues. Lane 2 is a sample obtained from a wild type *E. coli* strain. The wild type strain synthesizes several higher molecular weight LPS species, including those for the full length and the core LPS, but does not synthesize Re-LPS.

The invention relates to new compounds having the general formula (I)

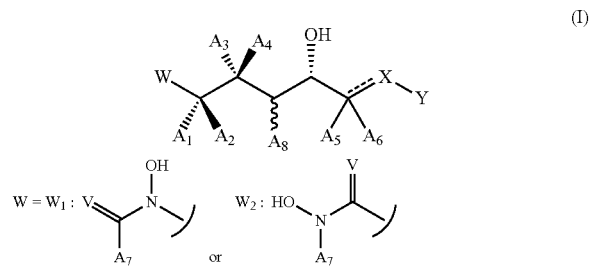

wherein, $A_1$ and $A_2$, identical or different, are H, $(C_1\text{-}C_6)$alkyl, $(C_1\text{-}C_6)$ fluoroalkyl, $(C_2\text{-}C_6)$alkenyl, $(C_2\text{-}C_6)$alkynyl, $(C_1\text{-}C_6)$alkyl-$OR_a$, $(C_1\text{-}C_6)$alkyl-$SR_a$, $(C_1\text{-}C_6)$alkyl-$NR_aR_b$, $OR_a$, $SR_a$, $NR_aR_b$, or $COR_a$;

$A_3$ is H, OH or form a carbonyl with $A_4$;

$A_4$ is H, OH or form a carbonyl with $A_3$;

$A_5$ is H, $CR_aR_bOH$, F, OH or forms a double bond with X in the case where X is CH;

$A_6$ is H or F;

X is $CH_2$, CHF, $CF_2$, CHOH, O, S, $NR_a$ or a simple bond, or X is CH in the case where $A_5$ forms with X a double bond;

Y is $P(O)(OR_a)(OR_b)$ or $P(O)(OR_a)(NR_aR_b)$;

V is O or S;

$A_7$ is H, $(C_1\text{-}C_6)$alkyl, $(C_1\text{-}C_6)$ fluoroalkyl, $(C_2\text{-}C_6)$alkenyl, $(C_2\text{-}C_6)$alkynyl or $(C_1\text{-}C_6)$alkyl-$OR_a$;

$A_8$ is OH or H $R_a$ and $R_b$, identical or different, are selected from the group consisting of H, $(C_1\text{-}C_6)$alkyl, $(C_1\text{-}C_6)$ fluoroalkyl, $(C_1\text{-}C_6)$alkyl-OH and $(C_1\text{-}C_6)$alkyl-O—$(C_1\text{-}C_6)$alkyl;

as well as the cyclic hemiketal or cyclic hemiacetal forms for compounds bearing carbonyl and hydroxyl groups, and their addition salts thereof with acids and bases.

It must be understood that $R_a$ and $R_b$, hereabove and hereafter in the processes, can be identical or different when they both appear in the definition of substituents $A_1$, $A_2$, $A_5$, $A_7$, X and Y taken individually as well as when they appear in the definition of these substituents and of leaving groups, with respect to each other.

Moreover it is understood that the invention doesn't extend to compounds wherein $A_5$ is OH when X is O, S or NR, and wherein $A_6$ is F when $A_5$ is OH.

In formula (I) the hydroxy substituent indicated in undetermined position can be in R, S or RS configuration and therefore the invention extends to the compounds of formula (I) in the form of pure diastereoisomers and mixtures of diastereoisomers.

Among the acid salts of the products of formula (I), there may be cited, among others, those formed with mineral acids, such as hydrochloric, hydrobromic, hydroiodic, sulfuric or phosphoric acid or with organic acids such as formic, acetic, trifluoroacetic, propionic, benzoic, maleic, fumaric, succinic, tartaric, citric, oxalic, glyoxylic, aspartic, alkanesulfonic acids, such as methanesulfonic and ethanesulfonic acids, arylsulfonic acids such as benzenesulfonic and para-toluenesulfonic acids.

Among the alkaline salts of the products of formula (I), there may be cited, among others, those formed with mineral alkalis such as, for example, sodium, potassium, lithium, calcium, magnesium or ammonium or organic bases such as, for example, methylamine, ethylamine, propylamine, trimethylamine, diethylamine, triethylamine, N,N-dimethylethanolamine, tris(hydroxymethyl)aminomethane, ethanolamine, pyridine, piperidine, piperazine, picoline, dicyclohexylamine, morpholine, benzylamine, procaine, lysine, arginine, histidine, N-methylglucamine.

In the general formula (I), as applied herein:

"$(C_1-C_6)$alkyl" means any linear, branched, mono or bicyclic hydrocarbon groups comprising 1 (or 3 for a cycle) to 6 carbon atoms, preferably methyl, ethyl, n-propyl, isopropyl, n-butyl, isobutyl and t-butyl, n-pentyl, isopentyl, neopentyl, cyclopropyl, cyclobutyl, cyclopentyl, cyclohexyl, bicyclo[3.1.0]hexane, bicyclo[2.2.0]hexane, spiro[2.2]pentane or spiro[2.3]hexane, or means an alkyl chain including or substituted by a small cycloalkyl, itself possibly substituted by an alkyl, or means a small cycloalkyl substituted by alkyl;

"$(C_2-C_6)$alkenyl" and "$(C_2-C_6)$alkynyl" as applied herein means any linear, branched or cyclic hydrocarbon groups of 2 to 6 carbon atoms, having at least one double bond or one triple bond and preferably ethenyl, propenyl, butenyl, cyclohexenyl, ethynyl, propargyl or butynyl.

"$(C_1-C_6)$fluoroalkyl" as applied herein means any mono or polyfluoro linear, branched or cyclic alkyl and preferably mono, di or trifluoalkyl.

By "cyclic hemiketal or cyclic hemiacetal forms" is understood all possible lactol forms existing in equilibrium with the open forms, for compounds bearing carbonyl and hydroxyl groups susceptible of reacting intramolecularly as commonly observed in carbohydrate chemistry (see for example Monosaccharides: Their chemistry and their roles in natural products. P. Collins and R. Ferrier 1995 John Wiley & Sons or Carbohydrate Chemistry B. G. Davis and A. J. Fairbanks 2002 Oxford University Press).

According to a preferred embodiment, Y is $P(O)(OH)_2$.

According to another preferred embodiment, X is $CH_2$, CHF, $CF_2$, CHOH or O.

According to another preferred embodiment, W is $W_1$ as defined above.

According to another preferred embodiment, $A_1$ and $A_2$ are H or one of them is H and the other is $(C_1-C_6)$alkyl, or one of them is H and the other is fluoro$(C_1-C_6)$alkyl, or one of them is H and the other is $(C_1-C_6)$alkyl-$OR_a$, or one of them is H and the other is $(C_1-C_6)$alkyl-$SR_a$, or one of them is H and the other is $COR_a$, $R_a$ being as defined above, or one of them is H and the other is OH.

According to another preferred embodiment, when $A_3$ forms a carbonyl with $A_4$, $A_5$ is OH or $CR_aR_bOH$, $R_a$ and $R_b$ being as defined above, or when $A_3$ doesn't form a carbonyl with $A_4$, $A_5$ is H or F.

According to another preferred embodiment, $A_7$ is H or $(C_1-C_6)$alkyl.

According to another preferred embodiment, $A_8$ is OH.

Among the compounds of the invention, there may be cited the following compounds:

D-altronohydroxamic acid 6-(dihydrogen phosphate),
N-hydroxy-N-formylamino-1-deoxy-D-ribitol-5-phosphate,
[6-(Formyl-hydroxy-amino)-(3R,4R,5S)-3,4,5-trihydroxy-hexyl]-phosphonic acid,
[[6-(Formyl-hydroxy-amino)-(3R,4R,5S)-1,3,4,5-tetra-hydroxy-hexyl]-phosphonic acid,
[(2S,3S,4S)-5-(Formyl-hydroxy-amino)-2,3,4-trihydroxy-pentyl]-phosphonic acid (1-(N-benzyloxy-N-formylamino)-1,5-dideoxy-D-ribitol] 5-phosphonic acid),
1-(N-benzyloxy-N-formylamino)-1-deoxy-5,6-dihydroxy-D-ribo-hexitol)]-6-phosphonic acid,
[(3R,4R,5S)-6-(Formyl-hydroxy-amino)-3,4,5,7-tetrahydroxy-heptyl]-phosphonic acid (diastereoisomers DIA1 and DIA2),
[1-Fluoro-6-(formyl-hydroxy-amino)-(3R,4R,5S)-3,4,5-trihydroxy-hexyl]-phosphonic acid,
(3R,4S,5R)-3,4,5-trihydroxy-6-(N-hydroxyformamido)hexyl)phosphonic acid,
(3R,4R,5R)-3,4,5-trihydroxy-6-(N-hydroxyformamido)-hexylphosphonic acid,
[1,1-Difluoro-6-(formyl-hydroxy-amino)-(3R,4R,5S)-3,4,5-trihydroxy-hexyl]-phosphonic acid,
[1-(N-hydroxy-N-formylamino)-1,6-dideoxy-D-allo/L-talo-hexitol)] 6-phosphonic acid,
1-(N-benzyloxy-N-formylamino)-1-deoxy-D-ribo-5-(E)-hexenitol 6-phosphonic acid, and their addition salts thereof with acids and bases, in particular their sodium salts.

The compounds of formula I may be prepared by any processes known to be applicable to the preparation of chemically related compounds (for non-limiting examples see in particular: Chem. Rev. 2006, 106, 3868; Tetrahedron 1997, 53, 16609; J. Med. Chem. 2010, 53, 5342; J. Med. Chem. 2010, 53, 7836). Such processes may use known starting materials or intermediates which may be obtained by standard procedures of organic chemistry. The following processes provide a variety of non-limiting routes for the production of the compounds of formula (I) and their intermediates.

Examples of processes to prepare compounds of formula (I) and salts thereof include in non-limiting manner the transformation into compounds of formula (I) of compounds of formula (II):

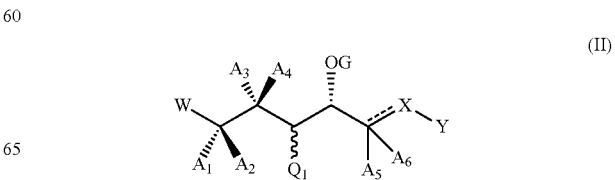

(II)

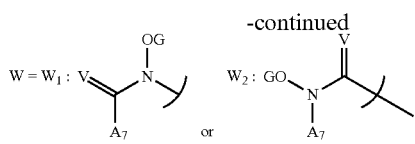

wherein X, Y, V, $A_1$, $A_2$, $A_3$, $A_4$, $A_5$, $A_6$, $A_7$, $W_1$ and $W_2$ are as above defined, when appropriate all of these groups are optionally protected by one or several identical or different groups PG, G is H or PG, PG is an appropriate protecting group (non-limiting examples of PG include optionally substituted alkyl, aryl, aralkyl and silyl, in particular methyl, ethyl, phenyl, benzyl, para-methoxybenzyl, trimethylsilyl, triphenylsilyl, tertbutyldimethylsilyl or tertbutyldiphenylsilyl, acyl, in particular acetyl or benzoyl, benzyloxycarbonyl and supported polymer resin), $Q_1$ is H or OG;
by one or more of the following reactions, performed in an appropriate order, to achieve the desired transformations on W and/or X and/or Y and/or $A_1$ and/or $A_2$ and/or $A_3$ and/or $A_4$ and/or $A_5$ and/or $A_6$ and/or $A_7$ and/or G, defined above:

protection of reactive functions,
deprotection of protected functions,
halogenation,
metathesis,
epoxidation,
epoxide opening,
dehalogenation,
dealkylation,
alkylation,
oxidation,
Wittig type reaction on carbonyl groups,
Mitsunobu type reaction,
dihydroxylation reaction of carbon-carbon double bonds,
reduction of nitro, esters, cyano, carbonyls, thioethers, double and triple bonds, hydroxy,
deoxygenation,
transition metal-catalyzed reactions,
etherification,
acylation,
sulfonylation/introduction of sulfonyl groups,
saponification/hydrolysis of esters groups,
halogen exchange,
nucleophilic substitution with amine, thiol or alcohol,
reductive amination,
phosphorylation,
sulphatation,
phosphitation, Arbuzov reaction, Michaelis-Becker reaction,
phosphorylation, (fluoro)methylphosphonylation,
amidation,
phosphoramidation,
oxime formation via addition of an hydroxylamine to a keto group or via nitroglycal reduction,
introduction of $R_a$, $R_b$ groups on $A_1$, $A_2$, $A_5$, $A_7$, X or Y groups;
deprotection of G to hydrogen when G is PG;
separation of diastereoisomers;
salification.

All these reactions are classical and known to the skilled chemist. General and more specific references can be cited, including, as a general reference, Michael B. Smith, Jerry March, March's Advanced Organic Chemistry: Reactions, Mechanisms, and Structure, 6th Edition, Wiley, 2007, and as more specific references, in particular those listed hereafter:

Protection and deprotection of reactive functions: Peter G. M. Wuts, Theodora W. Greene, Greene's Protective Groups in Organic Synthesis, 4th Edition, Wiley, 2006);
Halogenation reactions: Hanessian, Preparative Carbohydrate Chemistry, CRC Press, 1997;
DAST in the case of the fluoration of an hydroxyl leaving group;
Hydroxamate installation: J. Org. Chem 1998, 63, 1910;
Halogenoacylation reactions: Journal of Carbohydrate Chemistry 2007, 26, 141;
Halogenohydroxylation: Journal of Carbohydrate Chemistry 2001, 20, 359;
Epoxide formation and opening: J. Org. Chem. 1993, 58, 3761; Tet. Lett. 1994, 35, 8433;
Halogenophosphorylation reactions: Chem. Eur. J. 2008, 14, 9530;
Metathesis reaction: Tet. Lett. 2011, 52, 6767;
Oxidation reaction: Chem. Eur. J., 2010, 16, 8545;
Oxime formation via addition of an hydroxylamine to a keto group: Carbohydr. Res. 2009, 344, 2127; Carbohydr. Res. 1999, 320, 250; Tetrahedron 2001, 57, 7919; Tetrahedron: Asymmetry 2011, 22, 109; or via nitroglycal reduction: Eur. J. Org. Chem. 2010, 3579;
Wittig type reaction on carbonyl groups and homologations by Grignard reagents: J. Org. Chem. 2000, 65, 6493; Chem. Eur. J. 2008, 14, 9530; Pol. J. Chem. 1996, 70, 45; Angew. Chem. 2008, 120, 1731; Carbohydr. Res. 2005, 340, 2808; Carbohydr. Res. 1986, 152, 329; J. Am. Chem. Soc. 2006, 128, 8078; Tet. Lett. 2011, 52, 6767; Carbohydr. Res. 2001, 332, 225;
Dihydroxylation reaction of carbon-carbon double bonds: Noe, M. C., Letavic, M. A., Snow, S. L. 2005. and asymmetric dihydroxylation of alkenes: Organic Reactions. 109-625;
Transition metal-catalyzed reactions: Matthias Beller, Carsten Bolm, Transition Metals for Organic Synthesis, Wiley, 2004;
Mitsunobu reaction conditions: J. Org. Chem. 1998, 63, 1910;
Phosphorylation reaction: Chem. Eur. J. 2011, 17, 11305-11313; Carbohydrate Research 2005, 340, 2808; Carbohydrate Research 2003, 338, 2571, Tetrahedron Letters 1999, 40, 1869; Org. Lett. 2001, 3, 2009; J. Org. Chem. 2000, 65, 4498, Eur. J. Org. Chem. 2000, 3433;
Introduction of $R_a$, $R_b$ groups on $A_1$, $A_2$, $A_5$, $A_7$, X or Y groups are performed by known alkylation, acylation, alkoxylation, sulfenylation or amination reactions.
Separation of diastereoisomers can be carried out according to techniques known to a person skilled in the art, in particular chromatography or crystallization.
Compounds of formula (I) and salts thereof or intermediates of the synthetic route towards compounds of formula (I) may also be obtained in non-limiting manner by transformation of compounds of formula (III) or a salt thereof, by reacting a compound of formula (III):

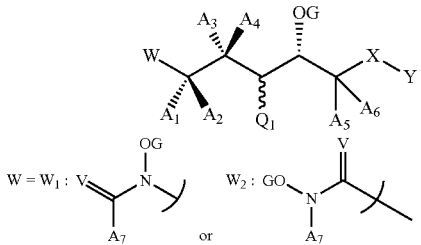
(III)

with Y-LG$_1$, POCl$_3$, PCl$_3$, PCl$_3$, POBr$_3$, PBr$_3$, P(OR$_a$)(OR$_b$)LG$_1$ or P(OR$_a$)(NR$_a$R$_b$)LG$_1$, followed as appropriate by one or more reactions including those listed above in the context of the transformation of compounds of formula (II) into compounds of formula (I).

Y, A$_1$, A$_2$, A$_3$, A$_4$, A$_5$, A$_6$, A$_7$, V, W$_1$, W$_2$, G and Q$_1$ are defined as above, X is O, S or NR$_a$, LG$_1$ is an appropriate leaving group (non-limiting examples of LG$_1$ include hydroxyl, OP(O)(OR$_a$)$_2$, NR$_a$R$_b$, OR$_a$, or halogen) and when appropriate X, Y, A$_1$, A$_2$, A$_3$, A$_4$, A$_5$, A$_6$, A$_7$, V, W$_1$ and W$_2$ are optionally protected by one or several identical or different protecting groups PG defined as above.

Non-limiting examples include phosphorylation with P(OR$_a$)(OR$_b$)LG$_1$, P(OR$_a$)(NR$_a$R$_b$)LG$_1$ or (R$_a$O)(R$_b$O)P(O)-LG$_1$, such as nucleophilic substitution in case LG$_1$ is halogen or diisopropylamine, or Mitsunobu reaction in case when LG$_1$ is hydroxy. In the case of phosphites synthesis with P(OR$_a$)(OR$_b$)LG$_1$ or P(OR$_a$)(NR$_a$R$_b$)LG$_1$ subsequent oxidation to phosphates is performed (non-limiting example includes mCPBA or DDQ oxidation of phosphite to phosphate derivatives).

Compounds of formula (I) and salts thereof or intermediates of the synthetic route towards compounds of formula (I) may also be obtained in non-limiting manner by transformation of compounds of formula (IV) or (V) or a salt thereof:

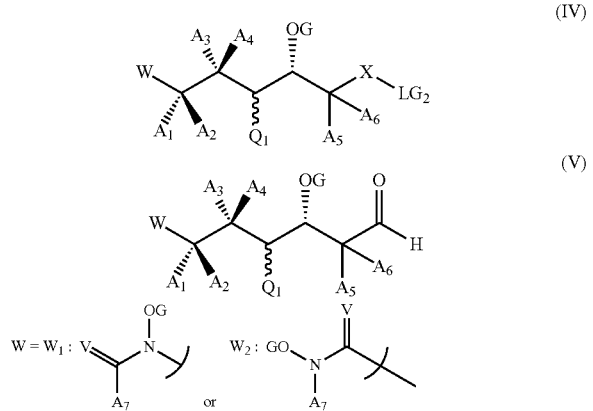

by their reaction with P(OR$_a$)$_3$, HP(O)(OR$_a$)(NR$_a$R$_b$) or HP(O)(OR$_a$)(OR$_b$) optionally in the presence of a suitable base and/or catalyst, followed as appropriate by one or more reactions including those listed above in the context of the transformation of compounds of formula (II) into compounds of formula (I).

A$_1$, A$_2$, A$_3$, A$_4$, A$_5$, A$_6$, A$_7$, V, R$_a$, R$_b$, W$_1$ and W$_2$, G and Q$_1$ are defined as above and when appropriate are optionally protected by one or several identical or different protecting groups PG, PG is as defined above, X is CH$_2$, CHF or CF$_2$ and LG$_2$ is an appropriate leaving group (non-limiting examples include OR$_a$, NR$_a$R$_b$, halogen, alkyl/fluoroalkylsulfonyloxy arylsulfonyloxy, thioalkyl/aryl, diazonium, fluorosulfonyloxy, trialkylammonium, O-acyl and phosphonium). Non-limiting examples of above reactions with compounds (IV) and (V) includes Arbuzov reaction of halides with trialkyl phosphites, base-catalyzed reactions between halides or aldehydes and H-phosphonate diesters with potassium hexamethylsilazane or sodium hydride (U.S. Pat. No. 4,693,742, DE2733658, Tet. Lett. 1993, 34, 8543); the addition of phosphites to aldehydes and aldimines (J. Am. Chem. Soc. 2008, 130, 10521).

Compounds of formula (I) and salts thereof or intermediates of the synthetic route towards compounds of formula (I) may also be obtained in non-limiting manner by transformation of compounds of formula (VI) or (VII) or a salt thereof:

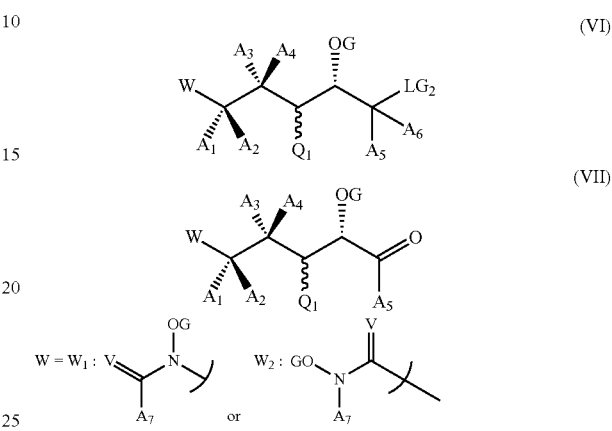

by their reaction with Y—XH, P(OR$_a$)$_3$, HP(O)(OR$_a$)(NR$_a$R$_b$), HP(O)(OR$_a$)(OR$_b$) or [P(O)(OR$_a$)(OR$_b$)]$_2$CH$_2$, optionally in the presence of a suitable base and/or catalyst, followed as appropriate by one or more reactions including those listed above in the context of the transformation of compounds of formula (II) into compounds of formula (I).

Y, X, A$_1$, A$_2$, A$_3$, A$_4$, A$_6$, A$_7$, V, R$_a$, R$_b$, W$_1$, W$_2$, G and Q$_1$ are defined as above and when appropriate are optionally protected by one or several identical or different protecting groups PG, PG is as defined above and LG$_2$ is an appropriate leaving group (non-limiting examples include OR$_a$, NR$_a$R$_b$, halogen, alkyl/fluoroalkylsulfonyloxy arylsulfonyloxy, thioalkyl/aryl, diazonium, fluorosulfonyloxy, trialkylammonium, O-acyl and phosphonium).

Non-limiting examples of above reactions with compounds (VI) and (VII) include methylphosphonylation, fluoromethylphosphonylation or difluoromethylphosphonylation in the presence of bases such as BuLi or LDA, Arbuzov reaction of halides with trialkyl phosphites, base-catalyzed reactions between halides or aldehydes and H-phosphonate diesters with potassium hexamethylsilazane or sodium hydride (U.S. Pat. No. 4,693,742, DE2733658, Tet. Lett. 1993, 34, 8543), addition of phosphites to aldehydes and aldimines (for example can be cited J. Am. Chem. Soc., 2008, 130, 10521).

Compounds of formula (I) and salts thereof or intermediates of the synthetic route towards compounds of formula (I) may also be obtained in non-limiting manner from compounds of formula (VIII), or a salt thereof:

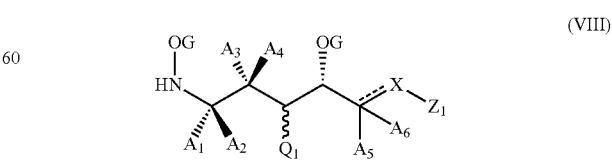

by coupling with A$_7$-C(V)LG$_3$, followed as appropriate by one or more reactions including those listed above in the context of the transformation of compounds of formula (II) into compounds of formula (I).

$Z_1$ is defined as Y or G, and X, Y, $A_1$, $A_2$, $A_3$, $A_4$, $A_5$, $A_6$, $A_7$, V, G and $Q_1$ are as above defined and when appropriate all of them are optionally protected by one or several identical or different protecting group PG, PG is as defined above, $LG_3$ is an appropriate leaving group typically used to activate carbonyl group towards acylation (non-limiting examples include $OR_a$, $NR_aR_b$, halogen, O-acyl, uronium, phosphonium, imidazolium, succinimide-N-oxy, phtalimide-N-oxy, pentafluorophenyloxy) (Bioorg. Med. Chem. 1996, 6, 2077).

Compounds of formula (VIII) may be prepared in non-limiting manner from compounds of formula (IX) or (X) or a salt thereof:

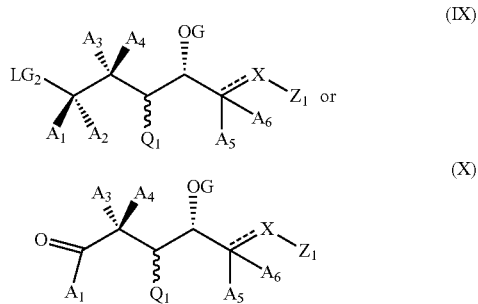

by their reaction with NHG-OG optionally in the presence of a suitable base and/or catalyst, and in the case of compounds of formula (X), in the presence of an appropriate reducing agent, followed as appropriate by one or more reactions including those listed above in the context of the transformation of compounds of formula (II) into compounds of formula (I).

$Z_1$ is defined as Y or G, and $A_1$, $A_2$, $A_3$, $A_4$, $A_5$, $A_6$, X, Y, $LG_2$, G and $Q_1$ are as above defined and when appropriate all of them are optionally protected by one or several identical or different protecting group PG, PG is as defined above.

Non-limiting examples of above reactions with compounds (IX) and (X) include:

Mitsunobu-type reaction where $LG_2$ is OH in the presence of di-alkylazodicarboxylate and triaryl/(cyclo)alkyl-phosphine (Org. Biomol. Chem. 2004, 2, 1145; WO2006/000294; U.S. Pat. No. 6,911,450); nucleophilic substitution-type reaction in the presence of appropriate base such as sodium hydride (WO2011/124712);

reductive amination of a compound of formula (X) with subsequent or one-pot reduction with reducing agents such as sodium cyanoborohydride or tris(acetoxy)borohydride (J. Med. Chem. 2001, 44, 937; Eur. J. Med. Chem. 2012, 51, 277).

Compounds of formula (I) where W is $W_1$ or intermediates of the synthetic route towards compounds of formula (I) and salts thereof may also be prepared in non-limiting manner from compounds of formula (IX) or a salt thereof:

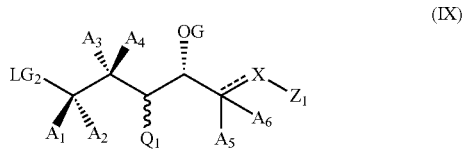

by their reaction with $NH(CVA_7)$-OG optionally in the presence of a suitable base and/or catalyst, followed as appropriate by one or more reactions including those listed above in the context of the transformation of compounds of formula (II) into compounds of formula (I).

$A_1$, $A_2$, $A_3$, $A_4$, $A_5$, $A_6$, $A_7$, V, X, $Z_1$ and $LG_2$, G and $Q_1$ are as defined above, when appropriate all of them are optionally protected by one or several identical or different protecting group PG, PG is as defined above.

Non-limiting examples of above reactions with compounds (IX) include:

substitution-type reactions of compound of formula (IX) with $NH(CVA_7)$-OPG in the presence of base such as potassium carbonate (Tet. Lett. 2004, 45, 491) or solid-state synthesis with N-acyl Wang-O-hydroxylamine resin in the presence of a base such as 1,8-diazabicyclo[5.4.0]undec-7-ene (Org. Lett. 2005, 7, 3761); Mitsunobu-type reaction where $LG_2$ is OH with $NH(CVA_7)$-OPG or N-acyl Wang-O-hydroxylamine resin in the presence of di-alkylazodicarboxylate (or 1,1'-(azodicarbonyl)diamine) and triaryl/(cyclo)alkyl-phosphine (J. Org. Chem. 1998, 63, 1910; Bioorg. Med. Chem. Lett. 2001, 11, 965; WO2008/033747; Org. Lett. 2005, 7, 3761).

Compounds of formula (I) where W is $W_2$ or intermediates of the synthetic route towards compounds of formula (I) where W is $W_2$ and salts thereof may also be prepared in non-limiting manner from compounds of formula (XI) or a salt thereof:

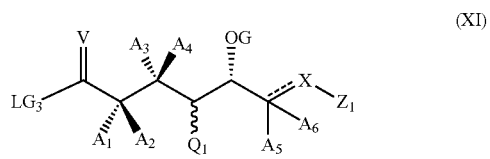

by coupling with $HNA_7$-OG optionally in the presence of appropriate base (non-limiting examples include 4-dimethylaminopyridine, triethylamine, lithium hexamethyldisilazane) and/or reagents typically used to activate carbonyl group towards acylations (non-limiting examples include benzotriazol-1-ol (HOBT), 1,1'-carbonyldiimidazole (CDI), dicyclohexylcarbodiimide (DCI), 2-(1H-7-azabenzotriazol-1-yl)-1,1,3,3-tetramethyl uronium hexafluorophosphate methanaminium (HATU), 1-ethyl-(3-(3-dimethylamino) propyl)-carbodiimide hydrochloride (EDAC)), followed as appropriate by one or more reactions including those listed above in the context of the transformation of compounds of formula (II) into compounds of formula (I).

$A_1$, $A_2$, $A_3$, $A_4$, $A_5$, $A_6$, $A_7$, V, $LG_3$, G and $Q_1$, $Z_1$ and X are as above defined, and when appropriate all of them are optionally protected by one or several identical or different protecting group PG, PG is as defined above.

It is also understood that $LG_3$ can be an oxygen atom which belongs to $A_1$, $A_2$, $A_3$, $A_4$ or $A_5$, or the oxygen of either group OG of the compound of formula (XI), in which case G is no longer present on the group involved, so to form a lactone, which will be substituted in a similar way in the coupling with $HNA_7$-OG. An illustration of such a lactone intermediate form is provided hereafter in the experimental part.

References illustrating reactions as performed above with the compounds of formula (XI) include inter alia the following: Eur. J. Med. Chem. 2012, 51, 277; WO2011/045703; J. Med. Chem. 2011, 54, 6796; J. Med. Chem. 2012, 55, 6566; J. Org. Chem. 2010, 75, 3203.

Compounds of formula (I) where W is W₁ or intermediates of the synthetic route towards compounds of formula (I) where W is W₁ and salts thereof may also be prepared in non-limiting manner from compounds of formula (XII) or a salt thereof:

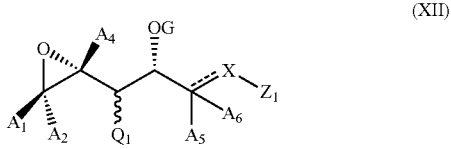

(XII)

by their reaction with NHG-OG or NH(CVA₇)-OG optionally in the presence of a suitable base and/or catalyst, followed as appropriate by one or more reactions including those listed above in the context of the transformation of compounds of formula (II) into compounds of formula (I). A₁, A₂, A₄, A₅, A₆, A₇, V, X, Z₁, G and Q₁ are as above defined and when appropriate all of them are optionally protected by one or several identical or different protecting group PG, PG is as defined above.

Moreover it is understood that this reaction doesn't extend to compounds wherein A₁, A₂ or A₄ is OH.

Non-limiting example includes reaction of epoxide opening with NH₂—OG in the presence of base such as triethylamine (Tetrahedron: Asymmetry, 2004, 15, 3201).

Compounds of formula (I) and salts thereof or intermediates of the synthetic route towards compounds of formula (I) may also be obtained in non-limiting manner by transformation of compounds of formula (XIII) or a salt thereof:

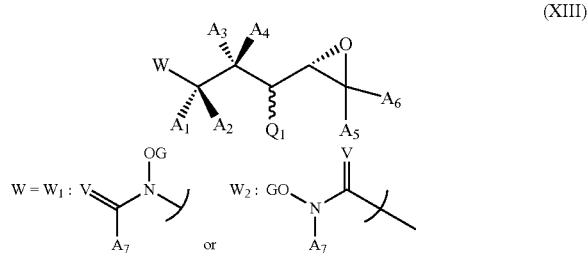

(XIII)

by their reaction with Y—XH or P(ORₐ)₃ optionally in the presence of a suitable base and/or catalyst, followed as appropriate by one or more reactions including those listed above in the context of the transformation of compounds of formula (II) into compounds of formula (I).

X, Y, A₁, A₂, A₃, A₄, A₅, A₆, A₇, V, Rₐ, W₁, W₂, G and Q₁ are defined as above, and when appropriate all of them are optionally protected by one or several identical or different protecting groups PG, PG is as defined above.

Moreover it is understood that this reaction doesn't extend to compounds wherein A₅ or A₆ is OH.

Non-limiting examples include methylphosphonylation, fluoromethylphosphonylation or difluoromethyl-phosphonylation with bases such as BuLi or LDA with optional presence of boron trifluoride diethyletherate (J. Med Chem. 2006, 49, 5309; J. Org. Chem. 1993, 58, 5779), phosphorylation with phosphoric acid with optional presence of CuI (U.S. Pat. No. 6,949,528).

Compounds of formula (I) wherein X is CH₂ and salts thereof or intermediates of the synthetic route towards compounds of formula (I) may also be obtained in non-limiting manner by transformation of compounds of formula (XIV) or a salt thereof:

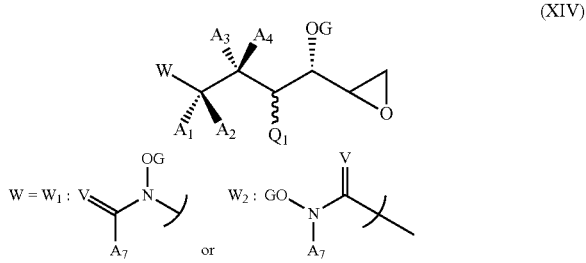

(XIV)

by their reaction with P(ORₐ)₃, HP(O)(ORₐ)(NRₐR_b) or HP(O)(ORₐ)(OR_b) optionally in the presence of a suitable base and/or catalyst, followed as appropriate by one or more reactions including those listed above in the context of the transformation of compounds of formula (II) into compounds of formula (I).

A₁, A₂, A₃, A₄, A₆, A₇, V, Rₐ, R_b, W₁, W₂, G and Q₂ are defined as above, and when appropriate are optionally protected by one or several identical or different protecting groups PG, PG is as defined above, and X is CH₂, CHF, CF₂. Non-limiting example includes base-catalyzed phosphonylation reactions between epoxydes and H-phosphonate diesters with BuLi as an example of base (Org. Lett. 2010, 12, 2302).

Compounds of formula (I) where W is W₁ and salts thereof or intermediates of the synthetic route towards compounds of formula (I) where W is W₁ and salts thereof may also be obtained in non-limiting manner by the reactions of compounds of formula (XV) or (XVI):

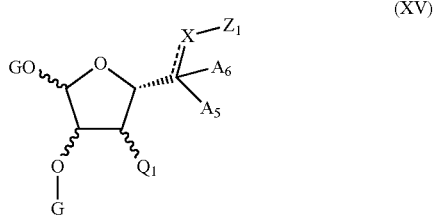

(XV)

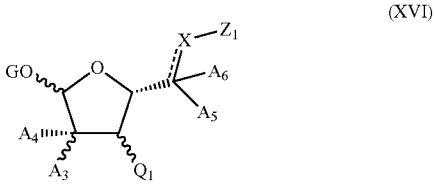

(XVI)

by their reaction with NH₂—OG in the presence of a suitable reducing agent and optionally in the presence of a suitable base and/or catalyst, followed by subsequent acylation with A₇-C(V)LG₃, followed as appropriate by one or more reactions including those listed above in the context of the transformation of compounds of formula (II) into compounds of formula (I).

A₃, A₄, A₅, A₆, A₇, V, X, Z₂, LG₃, G and Q₂ are as above defined, when appropriate all of them are optionally protected by one or several identical or different protecting group PG, PG is as defined above.

Non-limiting example includes reductive amination with protected hydroxylamine (Tet. Lett. 1998, 39, 2571) and reducing agents such as sodium cyanoborohydride or tris (acetoxy)borohydride).

In any of the above processes, if desired and appropriate, a separation of diastereoisomers can be carried out, according to techniques known to a person skilled in the art, in particular chromatography and/or crystallization.

The above intermediates of formulae (II) to (XVI) are known or compounds easily accessible from known compounds by classical techniques known to the skilled chemist. Illustrations of references which describe synthesis of such intermediates or usable techniques can be cited:

Tet. Lett. 1996, 37, 1221; J. Med. Chem. 1984, 27, 717; Tet. Lett. 1998, 39, 287; Tet. Lett. 1998, 39, 2571; U.S. Pat. No. 5,157,041 1992; ACS Med. Chem. Lett. 2010, 1, 101; Chem. Eur. J. 2004, 10, 1527; Tet. Lett. 1994, 35, 4935; J. Org. Chem. 2005, 70, 2398; J. Org. Chem. 1994, vol. 59, #20 p. 6063; Tet. Lett. 2005, 46, 2129; J. Org. Chem. 2006, 71, 3935; J. Org. Chem. 2005, 70, 2398; J. Org. Chem. 1987, 52, 1946; Tet. Lett. 40 (1999) 5095.

Compounds of formula (I) are capable of inhibiting bacterial heptose synthesis which makes them useful as drugs for preventing or treating bacterial infections and another object of the invention is the use of the compounds of formula (I) as drugs, and in particular for the prevention and therapeutical treatment of severe infections due to Gram-negative bacteria able to disseminate in blood such as the non-limiting following species (spp.): *Escherichia coli, Enterobacter, Salmonella, Shigella, Pseudomonas, Burkholderia, Acinetobacter, Neisseria, Klebsiella, Serratia, Citrobacter, Proteus, Yersinia, Haemophilus, Legionella, Moraxella* and *Helicobacter pylori*.

The invention also relates to pharmaceutical compositions comprising an effective amount of at least one compound of formula (I) such as above defined, in association with a pharmaceutically acceptable carrier.

Said pharmaceutical compositions are advantageously formulated to be administered under topic, oral, parenteral, and preferably injectable routes, with individual doses appropriate for the patient to be treated.

The compositions according to the invention can be solid or liquid and be present in the pharmaceutical forms commonly used in human medicine, such as for example, plain or sugar-coated tablets, gelatin capsules, granules, suppositories, inhalation spray, injectable preparations, ointments, creams, gels; they are prepared according to the customary methods.

The active ingredient(s) can be incorporated in same, using excipients which are customarily used in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting agents, dispersants or emulsifiers, preservatives.

These compositions can in particular be present in the form of a powder intended to be dissolved extemporaneously in an appropriate vehicle, for example, non-pyrogenic sterile water.

The dose administered varies according to the condition treated, the patient in question, the administration route and the product envisaged. It can, for example, be comprised between 0.01 g and 10 g per day, by oral route in humans or by intramuscular or intravenous route.

The drugs according to the invention can also be used, for the prevention as for the treatment of bacterial infections, in the form of associations with antibacterials or antivirulence agents or drugs reinforcing the host innate immunity. Of particular interest is the synergy obtained by the association with lipophilic compounds that have difficulties crossing the full hydrophilic LPS membrane, such as macrolides, streptogramins, pleuromutilins, FabI inhibitors, rifamycins and lipopeptides. Also of interest is the association with GM-CSF (Granulocyte macrophage colony-stimulating factor), an approved white blood cell growth factor.

A further object of the invention is therefore the associations of the compounds of formula (I) with antibacterials and/or antivirulence agents and/or drugs reinforcing the host innate immunity and, in particular, with antibacterials such as macrolides, streptogramins, pleuromutilins, FabI inhibitors, rifamycins, lipopeptides or with GM-CSF.

A further object of the invention is the pharmaceutical compositions containing the above associations with a pharmaceutically acceptable carrier.

Said pharmaceutical compositions are advantageously formulated as described above.

When the compound is administered in association, the doses administered vary according to the condition treated, the patient in question, the administration route and the associated active principles envisaged. The dose for the compound of formula (I) is the one indicated above and the dose for the associated active principle is the dose normally prescribed for such compound. For example, the compound of formula (I) can be administered in association with Erythromycin at doses of 250 to 500 mg every 6 hours in human (oral administration) or 1 g to 4 g per day in human in divided doses every 6 hours (intravenous administration) or by continuous infusion.

Illustrations of the invention are given in the following examples.

In the results concerning the pharmacological study of the compounds of the invention, it is referred to FIG. 1, which provides positive and negative controls obtained with a gel electrophoresis of (1) LPS of *E. coli* $C_7$-$\Delta$gmhA and (2) LPS of *E. coli* $C_7$ wild type.

EXPERIMENTAL PART

Materials and Procedures—

All chemicals are commercially available unless indicated otherwise and were used without further purification. Proton nuclear magnetic resonance (NMR) spectra were recorded on either a 300, 400 or 600 MHz Bruker instrument, and chemical shifts are reported in parts per million downfield from the internal standard tetramethylsilane (TMS). Abbreviations for NMR data are as follows: s=singlet, d=doublet, t=triplet, q=quadruplet, quint=quintuplet, sext=sextuplet, m=multiplet, dd=doublet of doublets, dt=doublet of triplets, td=triplet of doublets, tt=triplet of triplets, br=broad. J indicates the NMR coupling constant measured in Hertz. $CDCl_3$ is deuteriochloroform, DMSO-$d_6$ is hexadeuteriodimethylsulfoxide, and $CD_3OD$ is tetradeuteriomethanol. Mass spectra were obtained using electrospray ionization (ESI) techniques on an Agilent 1100 Series LCMS and 2795 Alliance Waters LCMS. Analtech Silica Gel GF and E. Merck Silica Gel 60 F-254 thin layer plates were used for thin layer chromatography. Flash chromatography was carried out on Flashsmart Pack cartridge irregular silica 40-60 µm or spherical silica 20-40 µm. Preparative thin layer chromatography was carried out on Analtech Silica Gel GF 1000 µm 20×20 cm.

The meaning of certain abbreviations is given herein. ESI refers to electrospray ionization, HPLC refers to high pressure liquid chromatography, LCMS refers to liquid chromatography coupled with a mass spectrometer, M in the context of mass spectrometry refers to the molecular weight, MS refers to mass spectrometry, ESI or ES refers to electrospray ionization, APCI refers to atmospheric-pressure chemical ionization, HRMS refers to high resolution mass spectrometry, NMR refers to nuclear magnetic resonance, pH refers to potential of hydrogen, TFA refers to trifluoroacetic acid, TEA refers to triethylamine, DIPEA refers to N,N-diisopropylethylamine, HOBt refers to 1-hydroxybenzotriazole, THF refers to tetrahydrofuran, DCM refers to dichloromethane, ACN or MeCN refers to acetonitrile, EtOAc or AcOEt refers to ethyl acetate, DME refers to 1,2-dimethoxyethane, DMF refers to N,N-dimethylformamide, TMSBr refers to trimethylsilyl-bromide, NBS refers to N-bromosuccinimide, NIS refers to N-iodosuccinimide, EDC, EDCI or EDAC refers N-(3-dimethylaminopropyl)-N'-ethylcarbodiimide hydrochloride, DMAP or 4-DMAP refers to 4-(dimethylamino)pyridine, Me refers to methyl, Et refers to ethyl, Bu refers to butyl, dppf refers to 1,1'-bis(diphenylphosphino)ferrocene, TBS or TBDMS refers to tetrabutyldimethylsilyl, TIPS refers to triisopropylsilyl, TBDPS refers to tert-butyldiphenylsilyl, TBAF refers to tetra-n-butylammonium fluoride, Ac refers to acetyl, Ph refers to phenyl, Bn refers to benzyl, Tf refers to triflate, Cbz refers to benzyl chloroformate, DMSO refers to dimethylsulfoxide, AIBN refers to azobisisobutyronitrile, 2,4-DNP or DNP refers to 2,4-dinitrophenol, NMO refers to N-methylmorpholine-N-oxide, TLC refers to thin layer chromatography, RT refers to room temperature. Florisil is the proprietary name for a type of activated magnesium silicate.

Example 1: D-altronohydroxamic acid 6-(dihydrogen phosphate)

Step 1: 1,2,3,4,6-Penta-O-acetyl-D-altropyranose (1a)

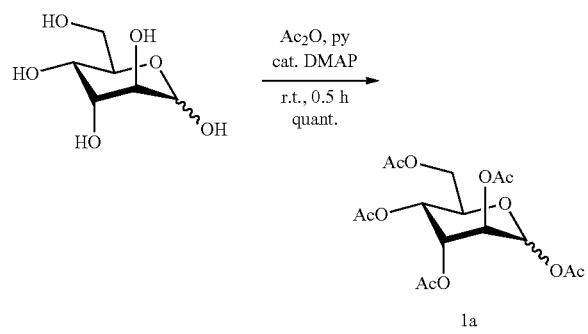

To a solution of D-altrose (2 g, 11 mmol) in pyridine (60 mL), were added acetic anhydride (50 mL) and a catalytic amount of DMAP. The mixture was stirred at room temperature for 30 min, whereupon TLC (3:2, hexane/EtOAc) showed complete conversion. Ethyl acetate (150 mL) was added and the mixture was washed with HCl 1N solution (200 mL). The aqueous phase was extracted with ethyl acetate (3×50 mL). The combined organic layers were washed with water and brine solution, then dried with magnesium sulfate, filtered and the solvent was evaporated. Diethyl ether was added to the residue and the solution was filtered through a short Florisil pad. The eluent was concentrated to afford the title compound (ratio α/β/furanose: 1:0.07:0.08) as a pale yellow oil (4.3 g, quant.) used as such for the next step.

Step 2: Phenyl 2,3,4,6-tetra-O-acetyl-1-thio-α-D-altropyranoside (1b)

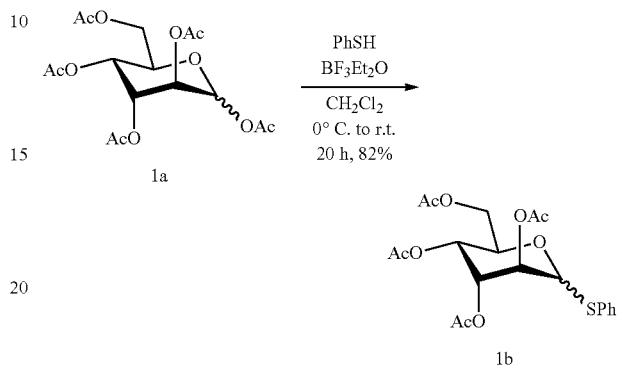

To a solution of penta-O-acetyl-D-altrose 1a (4.3 g, 11 mmol, ratio α-pyranose/β-pyr./fur.: 1:0.07:0.08) in anhydrous dichloromethane (60 mL), under argon atmosphere, was added thiophenol (16.5 mmol, 1.7 mL). Then at 0° C., BF$_3$.Et$_2$O (55 mmol, 6.8 mL) was added dropwise. The reaction mixture was allowed to warm at room temperature and it was stirred overnight, whereupon more thiophenol (8.8 mmol, 0.9 mL) and BF$_3$.Et$_2$O (0.04 mmol, 5.1 mL) were added. The mixture was stirred for more 4 h. Then it was diluted with dichloromethane, cooled to 0° C. and it was washed with a saturated solution of aqueous hydrogenocarbonate. The aqueous phase was extracted with dichloromethane. The combined organic phases were then washed with water and dried with magnesium sulfate. After filtration and evaporation of the solvent, the crude was purified by column chromatography on silica gel (hexane/EtOAc, from 7:3 to 3:2) to afford the phenyl thioglycoside as a colorless oil (4, 82%, ratio α-pyr/β-pyr./fur., 1:0.1:0.15), along with recovered starting material (244 mg, 6%).

$^1$H NMR (CDCl$_3$, 300 MHz, α-anomer) δ: 7.57-7.45 (m, 2H, Ph), 7.35-7.23 (m, 3H, Ph), 5.41 (brd, 1H, H-1), 5.33 (td, 1H, H-3, $J_{1,3}$=0.9 Hz, $J_{2,3}$=$J_{3,4}$=3.4 Hz), 5.24-5.17 (m, 2H, H-2, H-4), 4.81 (m, 1H, H-5, $J_{4,5}$=10.2 Hz, $J_{5,6a}$=5.7 Hz, $J_{5,6b}$=2.2 Hz), 4.36 (dd, part A of ABX system, 1H, H-6a, $J_{6a,6b}$=12.2 Hz), 4.20 (dd, part B of ABX system, 1H, H-6b).

$^{13}$C NMR (CDCl$_3$, 75 MHz, α-anomer) δ: 170.7, 169.6, 169.4, 169.4 (CO, Ac), 135.2 (Cq, Ph), 131.9, 129.2, 127.9, (CH, Ph), 86.1 (C-1), 71.4 (C-2), 66.9 (C-3), 65.6, 65.3 (C-4, C-5), 62.8 (C-6).

Step 3: Phenyl 1-thio-α-D-altropyranoside (1c)

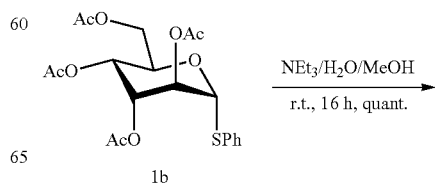

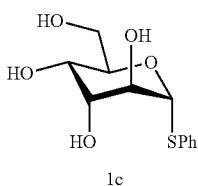

A solution of phenyl 2,3,4,6-tetra-O-acetyl-1-thio-α-D-altropyranoside 1b (97 mg, 0.22 mmol) in CH$_3$OH/H$_2$O/NEt$_3$ (8:1:1, 15 mL) was stirred overnight at room temperature. The solvents were evaporated under vacuum, the residue was lyophilized from water and the deprotected thioglycoside was obtained as a white solid (60 mg, quant). This protocol was also applied to a 1:0.11 mixture of α-pyranoside/furanoside (1.551 g, 3.52 mmol) and delivered the title product in 91% yield (873 mg).

$[α]_D^{23}$=+62 (c=1, in MeOH).

$^1$H NMR (MeOD, 300 MHz) δ: 7.58-7.48 (m, 2H, Ph), 7.33-7.15 (m, 3H, Ph), 5.27 (brd, 1H, H-1, $J_{1,2}$=1.6 Hz), 4.33 (ddd, 1H, H-5), 4.08 (dd, 1H, H-2, $J_{1,2}$=1.6 Hz, $J_{2,3}$=3.6 Hz), 3.96-3.74 (m, 4H, H-3, H-4, CH$_2$-6, $J_{3,4}$=3.6 Hz, $J_{4,5}$=9.7 Hz, $J_{5,6a}$=2.9 Hz, $J_{5,6b}$=5.2 Hz, $J_{6a,6b}$=11.7 Hz).

$^{13}$C NMR (MeOD, 75 MHz) δ: 139.0 (Cq, Ph), 132.2, 129.8, 127.8, (CH, Ph), 89.7 (C-1), 74.4 (C-2), 71.7, 71.4 (C-3, C-5), 66.0 (C-4), 63.0 (C-6).

HRMS (ESI$^+$): calcd for C$_{12}$H$_{16}$O$_5$S [M+NH$_4$]$^+$ 290.1057. found 290.1056.

Step 4: Phenyl 1-thio-6-O-triisopropylsilyl-α-D-altropyranoside (1d)

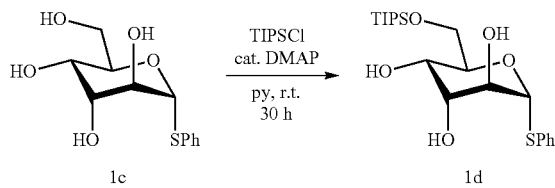

To a solution of phenyl 1-thio-D-altroside 1c (823 mg, 3.03 mmol, ratio α pyranoside/fur.: 1:0.11) in dry pyridine (30 mL), under argon, was added DMAP (cat. amount). Then, at 0° C., TIPSCl (2 equiv., 6.05 mmol, 1.16 g, 1.3 mL) was added dropwise. The mixture was allowed to warm at room temperature and after stirring for 3 h, more TIPSCl (1 equiv. 0.7 mL) and DMAP (catalytic amount) were added. The reaction mixture was left stirring overnight whereupon another spatula tip of DMAP and more TIPSCl (1 equiv., 0.7 mL) were added. After 7 h, TLC (EtOAc/MeOH, 1:9) showed virtually complete conversion. The mixture was diluted with EtOAc and washed with water. The aqueous phase was extracted with EtOAc. The combined organic phases were washed with water and dried with magnesium sulfate. After filtration and evaporation of the solvent, the residue was subjected to column chromatography on silica-gel (EtOAc/hexane, 2:3) to give the title compound as a colorless oil (1.222 g, 94%: 963 mg of a 1:0.07 α-pyranoside/furanoside mixture; amount of isolated furanoside: 60 mg).

$[α]_D^{22}$=+154 (c=1.2, in CHCl$_3$).

$^1$H NMR (CDCl$_3$, 300 MHz) δ: 7.52-7.44 (m, 2H, Ph), 7.33-7.20 (m, 3H, Ph), 5.31 (d, 1H, H-1, $J_{1,2}$=2.4 Hz), 4.37 (ddd, 1H, H-5), 4.18 (ddd, 1H, H-2), 4.11-3.98 (m, 3H, H-3, H-4, H-6a, $J_{5,6a}$=4.8 Hz, $J_{6a,6b}$=10.0 Hz), 3.93 (dd, part B of ABX system, 1H, H-6b, ($J_{5,6b}$=7.7 Hz), 3.71 (d, 1H, OH, J=1.6 Hz), 2.85 (d, 1H, OH, J=1.6 Hz), 2.18 (d, 1H, OH-2, J=6.3 Hz), 1.14-1.05 (m, 21H, 3×i-Pr, TIPS).

$^{13}$C NMR (CDCl$_3$, 75 MHz) δ: 136.3 (Cq, Ph), 131.2, 129.1, 127.3, (CH, Ph), 87.9 (C-1), 71.9 (C-3), 70.1 (C-2), 69.5 (C-4), 68.4 (C-5), 66.3 (C-6), 18.0 (Me, i-Pr, TIPS), 11.9 (CH, i-Pr, TIPS).

HRMS (ESI$^+$): calcd for C$_{21}$H$_{36}$O$_5$SSi [M+Na]$^+$ 451.1945. found 451.1958.

Step 5: Phenyl 2,3,4-tri-O-benzyl-1-thio-6-O-triisopropylsilyl-α-D-altropyranoside (1e)

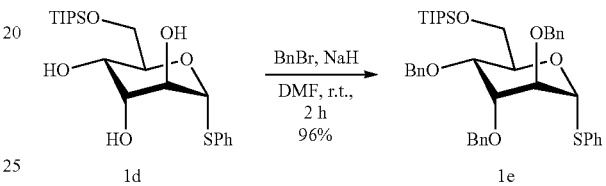

To a solution of 6-O-TIPS phenyl 1-thio-α-altroside (963 mg, 2.25 mmol, ratio α pyranoside/fur.: 1:0.07) in dry DMF (60 mL), under argon and at 0° C., NaH (60%, 6 equiv., 13.5 mmol, 540 mg) was added. After a few minutes, benzyl bromide (6 equiv., 13.5 mmol, 1.6 mL) was added dropwise. The mixture was stirred at room temperature for 2 h, whereupon TLC (EtOAc/hexane, 1:2) showed complete conversion. The mixture was cooled to 0° C. and water was added. The phases were separated and the aqueous phase was extracted with diethyl ether. The combined organic phases were washed with water and then dried with magnesium sulfate. After filtration and evaporation of the solvent under vacuum, the residue was purified by column chromatography on silica-gel (EtOAc/hexane, 1:23) to give the title compound as a colorless oil (1.5 g, 96%: 1.369 g of a 1:0.08 α-pyranoside/furanoside mixture; amount of isolated α-pyranoside: 131 mg).

$[α]_D^{20}$=+70 (c=1, in CHCl$_3$).

$^1$H NMR (CDCl$_3$, 600 MHz) δ: 7.53-7.50 (m, 2H, Ph), 7.39-7.17 (m, 18H, Ph), 5.47 (br.s, 1H, H-1), 4.71 (d, part A of AB system, 1H, H-a, Bn, J=12.4 Hz), 4.62 (d, part B of AB system, 1H, H-b, Bn), 4.57 (d, part A of AB system, 1H, H-a, Bn, J=12.4 Hz), 4.54-4.47 (m, 3H, CH$_2$, Bn, H-5), 4.39 (d, part B of AB system, 1H, H-b, Bn), 4.03-3.95 (m, 3H, H-4, CH$_2$-6, $J_{5,6a}$=4.0 Hz, $J_{6a,6b}$=11.0 Hz) 3.96 (dd, 1H, H-2, $J_{1,2}$=1.5 Hz, $J_{2,3}$=4.1 Hz), 3.83 (t, 1H, H-3, $J_{2,3}$=$J_{3,4}$), 1.14-1.04 (m, 21H, 3×i-Pr, TIPS).

$^{13}$C NMR (CDCl$_3$, 150 MHz) δ: 138.7, 138.4, 138.3, 138.1 (4×Cq, Ph), 130.5, 128.8, 128.6, 128.5, 128.4, 128.1, 128.0, 127.9, 127.8, 127.7, 127.6, 126.6 (CH, Ph), 85.6 (C-1), 78.1 (C-2), 73.7 (C-3), 72.9 (C-4), 72.6, 72.3, 72.0, 72.0, 70.2 (4×CH$_2$Ph, C-5), 63.2 (C-6), 18.2, 18.1 (Me, i-Pr, TIPS) 12.2 (CH, i-Pr, TIPS).

HRMS (ESI$^+$): calcd for C$_{42}$H$_{54}$O$_5$SSi [M+NH$_4$]$^+$ 716.3799. found 716.3803.

Step 6: Phenyl 2,3,4-tri-O-benzyl-1-thio-α-D-altropyranoside (1f)

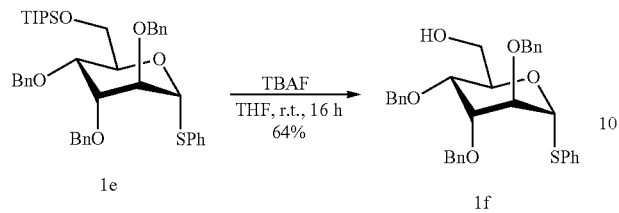

To a solution of benzylated 6-O-TIPS phenyl thioaltropyranoside (34 mg, 0.05 mmol) in THF (1.3 mL), under argon, was added TBAF (1 M in THF, 0.2 mmol, 0.2 mL). The reaction was stirred overnight at room temperature. The solution was diluted with diethyl ether and then it was washed with a saturated ammonium chloride solution. The aqueous layer was extracted with Et$_2$O. The combined organic layers were dried with magnesium sulfate. After filtration and evaporation of the solvent, the residue was purified by column chromatography on silica gel (hexane/EtOAc, 1:5 to 1:2.5) to give the title compound (17 mg, 64%) as colorless oil. This protocol was also applied to a 1:0.08 mixture of α-pyranoside/furanoside (1.369 g, 1.95 mmol), the reaction was completed within 1 h to afford 628 mg (60% yield) of the deprotected phenyl thioaltroside.

$[\alpha]_D^{25} = +103$ (c=0.6, in CHCl$_3$).

$^1$H NMR (toluene-d$_8$, 600 MHz) δ: 7.56-7.53 (m, 2H, Ph), 7.39-7.36 (m, 2H, Ph), 7.23-7-20 (m, 2H, Ph), 7.17-6.97 (m, 14H, Ph), 5.61 (br.s, 1H, H-1), 4.79 (dt, 1H, H-5, ($J_{5,6a}=J_{5,6b}=3.3$ Hz, $J_{4,5}=9.8$ Hz), 4.65 (d, part A of AB system, 1H, H-a, Bn, J=12.4 Hz), 4.56 (d, part B of AB system, 1H, H-b, Bn), 4.34 (s, 2H, CH$_2$, Bn), 4.26 (d, part A of AB system, 1H, H-a, Bn, J=12.1 Hz), 4.09-4.05 (m, 2H, H-b, Bn, H-4, $J_{3,4}=2.9$ Hz), 4.00 (br.d, 1H, H-2, $J_{2,3}=3.7$ Hz), 3.88-3.83 (m, 2H, H-3, H-6), 3.81 (dd, part B of ABX system, 1H, H-6b, ($J_{5,6a}=4.0$ Hz, $J_{6a,6b}=11.7$ Hz).

$^{13}$C NMR (toluene-d$_8$, 150 MHz) δ: 86.5 (C-1), 78.8 (C-2), 74.0 (C-3), 73.6, 73.1, 72.1, 71.8 (C-4, 3×CH$_2$Ph), 69.5 (C-5), 62.6 (C-6).

HRMS (ESI$^+$): calcd for C$_{33}$H$_{34}$O$_5$S [M+NH$_4$]$^+$ 560.2465. found 560.2467. calcd for [M+Na]$^+$ 565.2019. found 565.2024.

Step 7: Phenyl 2,3,4-tri-O-benzyl-6-O-[bis(phenoxy)phosphoryl]-1-thio-α-D-altropyranoside (1g)

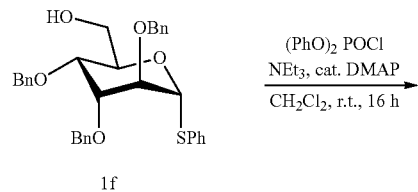

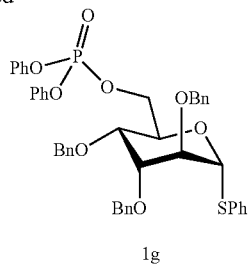

To a solution of phenyl 2,3,4-tri-O-benzyl-1-thio-α-D-altropyranoside (245 mg, 0.45 mmol) in dry dichloromethane (25 mL) were added, under argon, triethylamine (0.1 mL, 0.72 mmol) and DMAP (catalytic amount). The solution was cooled to 0° C. and diphenyl phosphorochloridate (0.1 mL, 0.48 mmol) was added. The reaction mixture was allowed to warm up to room temperature and it was stirred overnight. The mixture was diluted with dichloromethane (20 mL) and then washed with a saturated aqueous solution of hydrogenocarbonate (8 mL). The organic phase was dried with magnesium sulfate. After filtration and evaporation of the solvent, the residue was purified by column chromatography on silica gel (hexane/EtOAc, 1:4, containing 1% of NEt$_3$) to give the title compound (338 mg, 97%) as a colorless oil.

$[\alpha]_D^{24} = +20.7$ (c=0.5, in CHCl$_3$).

$^1$H NMR (CDCl$_3$, 300 MHz) δ: 7.50-7.42 (m, 2H, Ph), 7.40-7.15 (m, 28H, Ph), 5.46 (br.s, 1H, H-1), 4.74 (ddd, 1H, H-5), 4.68 (d, part A of AB system, 1H, H-a, Bn, J=12.3 Hz), 4.61-4.49 (m, 4H, CH$_2$-6, H-b, Bn, H-a, Bn), 4.38 (d, part B of AB system, 1H, H-a, Bn, J=12.2 Hz), 4.30 (br.s, 1H, CH$_2$Ph), 3.98 (dd, 1H, H-2, $J_{2,3}=3.5$ Hz), 3.90 (dd, 1H, H-4, $J_{3,4}=2.9$ Hz, $J_{4,5}=10.0$ Hz), 3.82 (t, 1H, H-3).

$^{13}$C NMR (CDCl$_3$, 75 MHz) δ: 150.7, 137.9, 137.6 (Cq, Ph), 130.7, 129.8, 129.7, 129.7, 129.0, 128.6, 128.5, 128.5, 128.1, 128.0, 127.9, 127.8, 126.9, 125.3, 120.4, 120.3, 120.3, 120.3 (CH, Ph), 85.9 (C-1), 77.4 (C-2), 72.6, 72.4, 72.3, 72.1 (2×CH$_2$Ph, C-3, C-4), 71.5 (CH$_2$Ph), 68.5 (C-6, $J_{C-6,P}=5.6$ Hz), 67.3 (C-5, $J_{C-5,P}=8.2$ HZ).

$^{31}$P NMR (CDCl$_3$, 121.5 MHz) δ: −11.97

Step 8: 2,3,4-Tri-O-benzyl-6-O-[bis(phenoxy)phosphoryl]-D-altropyranose (1h)

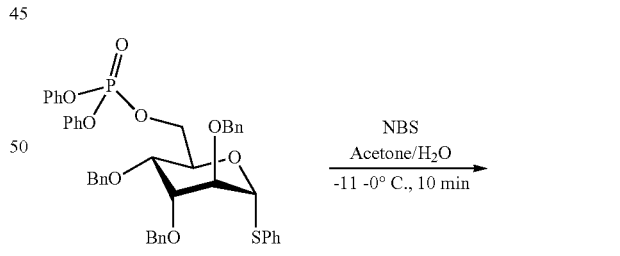

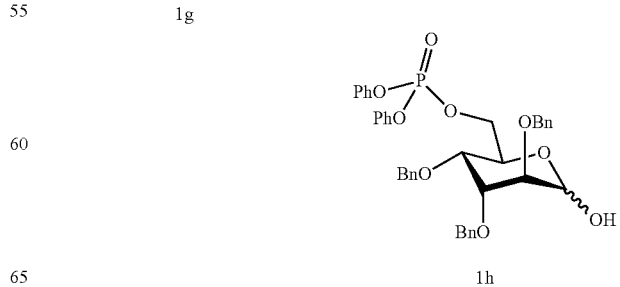

To a solution of the phenyl thioglycoside (331 mg, 0.43 mmol) in acetone/water (36 mL, 5:1) at −11° C., N-bromosuccinimide (NBS, 5 equiv, 2 mmol, 380 mg) was added in absence of light. After 10 min at −11 to 0° C., whereupon complete conversion was observed by TLC, the reaction mixture was diluted with dichloromethane (40 mL), washed with a saturated aqueous solution of hydrogenocarbonate (10 mL), and then with a saturated aqueous solution of sodium thiosulfate (10 mL). The combined aqueous phases were extracted with dichloromethane. The combined organic layers were dried with magnesium sulfate and filtered. After concentration under vacuum, the residue was purified by column chromatography on silica gel (EtOAc/hexane, 1:2) to yield the title compound as colorless oil (284 mg, 98%).

$^1$H NMR (CDCl$_3$, 300 MHz) δ: 7.39-7.06 (m, Ph), 5.06 (br.s, H-1α), 5.04 (d, H-1β, $J_{1,2(\beta)}$=1.8 Hz), 4.71 (d, part A of AB system, H-a, Bn, J=11.7 Hz), 4.65-4.23 (m, CH$_2$-6α, CH$_2$-6β, H-5α, CH$_2$Ph-α, CH$_2$Ph-β), 4.11 (ddd, H-5β), 3.95-3.87 (m, H-3α, H-4α, $J_{3,4\,(\alpha)}$=2.8 Hz, $J_{4,5\,(\alpha)}$=10.7 Hz), 3.78-3.71 (m, H-3H-4 $J_{3,4\,(\beta)}$=2.8 Hz, $J_{4,5\,(\beta)}$=10.7 Hz), 3.60 (br. d, 1H, H-2α, $J_{2,3\,(\alpha)}$=3.6 Hz), 3.48 (dd, 1H, H-2β, $J_{2,3\,(\beta)}$=3.5 Hz).

$^{13}$C NMR (CDCl$_3$, 75 MHz) δ: 150.8, 150.7, 138.0, 137.8, 137.7, 137.6, 137.0 (Cq, Ph), 129.8, 129.8, 128.8, 128.8, 128.7, 128.6, 128.6, 128.5, 128.4, 128.2, 128.2, 128.1, 128.1, 128.1, 128.0, 125.3, 125.3, 120.5, 120.4, 120.4, 120.3 (CH, Ph), 93.1 (C-1α), 92.0 (C-1β), 76.9 (C-2β, 74.9 (C-2α), 74.3, 74.3, 73.6, 73.3, 72.3, 72.2, 72.2, 72.0, 71.9 (CH$_2$Ph, C-3, C-4, α, β, 71.3 (C-5β, $J_{C-5,P}$=8.2 Hz), 68.5 (C-6β, $J_{C-6,P}$=6.2 Hz), 68.4 (C-6α, $J_{C-6,P}$=5.9 Hz), 66.1 (C-5α, $J_{C5,P}$=8.2 Hz).

$^{31}$P NMR (CDCl$_3$, 121.5 MHz) δ: −11.87, −12.02.

HRMS (ESI$^+$): calcd for C$_{39}$H$_{39}$O$_9$P [M+NH$_4$]$^+$ 700.267. found 700.2668.

Step 9: 2,3,4-Tri-O-benzyl-6-O-[bis(phenoxy)phosphoryl]-D-altrono-δ-lactone (1i)

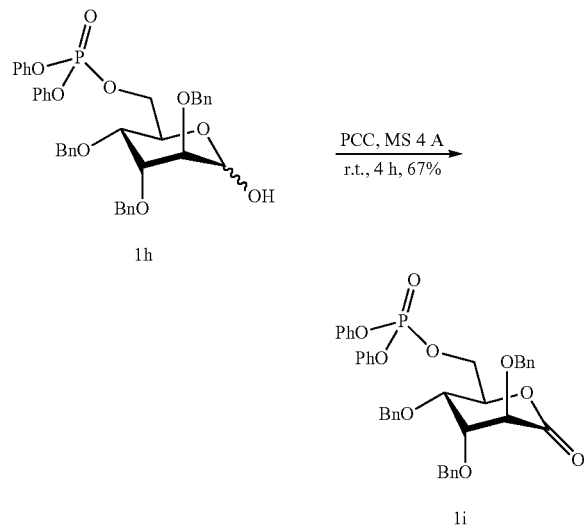

To a solution of lactol (280 mg, 0.04 mmol) in anhydrous dichloromethane (30 mL) under argon, 4 Å molecular sieves (330 mg, previously activated at 200° C. overnight and then cooled to room temperature under high vacuum) were added and the mixture was stirred at room temperature for 20 min. Then pyridinium chlorochromate (9 equiv., 798 mg, 3.7 mmol) was added and the whole mixture was stirred at room temperature. After 3 h more pyridinium chlorochromate (1.9 equiv., 170 mg) was added to drive the reaction to completion (2 h). The solvent was concentrated; the residue was triturated with diethyl ether and filtered over a Florisil pad. The eluent was concentrated in vacuum to give the aldonolactone (188 mg, 67%) as colorless oil.

$[α]_D^{22}$=−4.0 (c=0.5, in CHCl$_3$).

$^1$H NMR (CDCl$_3$, 300 MHz) δ: 7.38-7.10 (m, 23H, Ph), 6.95-6.87 (m, 2H, Ph), 4.81-4.70 (m, 2H, H-5, H-a, Bn, J=11.8 Hz), 4.57-4.48 (m, H-b, Bn, CH$_2$-6, CH$_2$Ph), 4.35 (2 d, AB system, 2H, CH$_2$Ph, J=11.4 Hz), 4.13 (dd, 1H, H-4, $J_{3,4}$=2.4 Hz, $J_{4,5}$=8.9 Hz), 4.06 (d, 1H, H-2, $J_{2,3}$=4.2 Hz), 3.87 (dd, 1H, H-3).

$^{31}$P NMR (CDCl$_3$, 121.5 MHz) δ: −12.18.

$^{13}$C NMR (CDCl$_3$, 75 MHz) δ: 167.2 (CO), 150.6, 150.4, 137.4, 137.2 (Cq, Ph), 130.0, 130.0, 130.0, 129.8, 128.3, 128.3, 128.2, 128.0, 125.7, 125.7, 125.6, 120.8, 120.4, 120.3, 120.3, 120.3 (CH, Ph), 76.4 (C-5, $J_{C-5,P}$=8.4 Hz), 74.9 (C-2), 73.3 (C-3), 73.2 (CH$_2$Ph), 72.9, 72.6 (2×CH$_2$Ph), 70.6 (C-2), 67.0 (C-6, $J_{C-5,P}$=5.4 Hz).

HRMS (ESI$^+$): calcd for C$_{39}$H$_{37}$O$_9$P [M+H]$^+$ 681.2248. found 681.2266. calcd for [M+NH$_4$]$^+$ 698.2513. found 698.253.

Step 10: D-altrono-δ-lactone 6-(dihydrogen phosphate) (1j)

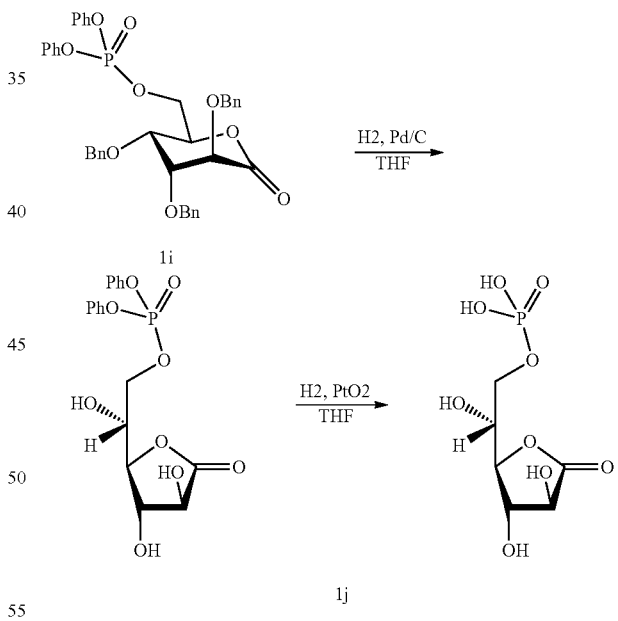

To a solution of aldonolactone 1i (93 mg, 0.14 mmol) in anhydrous THF (6 mL) was added 10% Pd/C (catalytic amount). The mixture was placed under hydrogen atmosphere and stirred overnight at room temperature, whereupon TLC showed complete conversion (EtOAc). The catalyst was then filtered off; the eluent was concentrated under vacuum and lyophilized from water. The resulting crude compound (52 mg) was dissolved in THF (4 mL), and PtO2 (catalytic amount) was added. The mixture was stirred under hydrogen atmosphere overnight, whereupon TLC (EtOAc/MeOH/H$_2$O, 5:4.5:0.5) showed complete conversion. The catalyst was filtered off and the eluent was concentrated in vacuum. The residue was dissolved in water and washed with diethyl ether. The aqueous phase was lyophilized to give a white hygroscopic solid which was then dissolved in water (HPLC grade) and subjected to gel filtration using a PD-10 Sephadex G 25 column (water as eluent). The eluent was lyophilized to afford the title compound (32.6 mg, 90%).

$^1$H NMR (D$_2$O, 600 MHz, lactone) δ: 4.58 (d, 1H, H-2, J$_{2,3=8.6}$ Hz), 4.41 (t, 1H, H-3), 4.36 (dd, 1H, H-4, J$_{3,4}$=8.1 Hz, J$_{2,3}$=3.9 Hz), 4.20 (ddd, 1H, H-5), 4.08-4.01 (m, H-6a), 3.99-3.94 (ddd, H-6 b).

$^{13}$C NMR (D$_2$O, 150 MHz, lactone) δ: 176.7 (C-1), 80.7 (C-4), 77.8 (C-2), 73.6 (C-3), 69.9 (d, C-5, J$_{C-5,P}$=7.7 Hz), 66.2 (d, C-6, J$_{C-6,P}$=4.9 Hz).

$^{31}$P NMR (CDCl$_3$, 242.9 MHz) δ: 0.27.

LCMS: [M+H]$^+$ 259; [M+Na]$^+$ 281; [M−H]$^+$ 257.

Acid: [M−H]$^+$ 275

Step 11: D-altronohydroxamic acid 6-(dihydrogen phosphate) (1k)

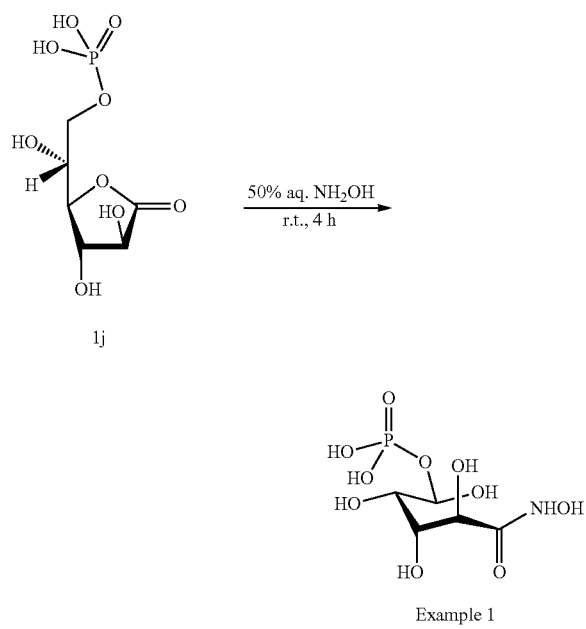

To a solution of D-altrono-6-lactone 6-(dihydrogen phosphate) (10 mg, 39 μmol) in water (1.5 mL) was added a 50% aqueous hydroxylamine (0.4 mmol, 24 μL). The reaction was stirred at room temperature for 4 h. The solution was concentrated under vacuum and then lyophilized. The residue was subjected to gel filtration chromatography (Bio-gel P-2) to afford the target compound (10 mg, 88%).

$^1$H NMR (D$_2$O, 600 MHz) δ: 4.49 (d, 1H, H-2, J$_{2,3}$=1.7 Hz), 4.06-3.91 (m, H-3, H-5, CH$_2$-6, J$_{3,4}$=8.6 Hz), 3.81 (dd, H-4, J$_{4,5}$=4.9 Hz).

$^{31}$P NMR (D$_2$O, 242.9 MHz) δ: 2.67.

LCMS: [M+H]$^+$ 292; [M−H]$^−$ 290.

Example 2: N-hydroxy-N-formylamino-1-deoxy-D-ribitol-5-phosphate (monosodium salt)

Step 1: Triisopropyl-((2R,3R,4R)-2,3,4-tris-benzyloxy-5,5-bis-ethylsulfanyl-pentyloxy)-silane (2a)

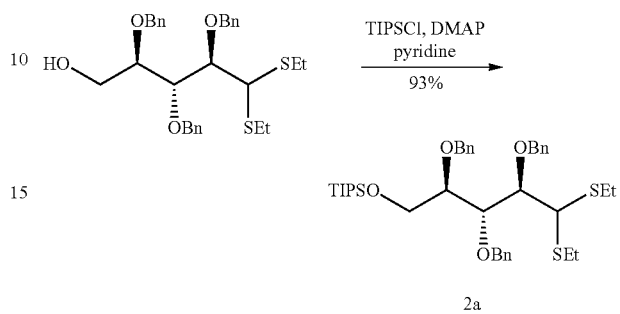

Compound (2R,3R,4R)-2,3,4-Tris-benzyloxy-5,5-bis-ethylsulfanyl-pentan-1-ol prepared as in *J. Org. Chem.* 1987, 52, 1946 (300 mg, 0.57 mmol) was dissolved in dry pyridine (2 mL). DMAP (70 mg, 0.57 mmol) and TIPSCl (183 μl, 0.85 mmol) were added to the solution and the reaction mixture was stirred at room temperature for 5 h. More DMAP (70 mg, 0.57 mmol) and TIPSCl (183 μL, 0.85 mmol) were added and stirring was continued for 9 h. Methanol (70 μL, 1.73 mmol) was added and stirring was continued for 30 minutes. The reaction mixture was diluted with toluene and evaporated, then diluted with diethylether (15 mL) and washed with a saturated aqueous solution of sodium hydrogenocarbonate (5 mL). The organic phase was dried over magnesium sulfate, concentrated and purified via column chromatography on silica gel (15 g, toluene:hexane 2:1→5:1) to give the title compound as colorless oil (356 mg, 0.53 mmol, 93%).

[α]$_D^{20}$ +20.7 (c 1.0, CHCl$_3$).

$^1$H NMR (300 MHz, CDCl$_3$): δ 7.36-7.22 (15H, 3×Ph), 4.98-4.57 (m, 6H, 3×OCH$_2$Ph), 4.26 (d, 1H, J$_{1,2}$=3.3 Hz, H-1), 4.13 (dd, 1H, J$_{3,2}$=7.5 Hz, J$_{3,4}$=1.9 Hz, H-3), 4.05 (dd, 1H, J$_{2,1}$=3.3 Hz, J$_{2,3}$=7.5 Hz, H-2), 3.99-3.91 (m, 2H, H-4, H-5a), 3.89-3.79 (m, 1H, H-5b), 2.70-2.55 (m, 4H, 2×SCH$_2$CH$_3$), 1.24-1.13 (m, 6H, 2×SCH$_2$CH$_3$), 1.05-0.95 [m, 21H, Si(CHMe$_2$)$_3$].

$^{13}$C NMR (150 MHz, CDCl$_3$): δ 139.00, 138.62, 138.51 (3×arom. C), 128.25, 128.15, 128.11, 127.82, 127.68, 127.47, 127.80, 127.28, 127.26 (arom C), 82.78 (C-2), 81.04 (C-4), 78.81 (C-3), 74.75, 73.15, 72.93 (3×OCH$_2$Ph), 64.10 (C-5), 54.14 (C-1), 26.21, 24.95 (2×SCH$_2$CH$_3$), 18.02 [Si (CHMe$_2$)$_3$], 14.46, 14.44 [2×Si(CH(CH$_3$)$_2$]$_3$, 11.91 [Si(CH (CH$_3$)$_2$)$_3$].

HRMS ESI+ C$_{39}$H$_{58}$O$_4$S$_2$Si [M+Na]+: calculated: 705.3438. found: 705.3437.

Step 2: (2R,3R,4R)-2,3,4-Tris-benzyloxy-5-triisopropylsilanyloxy-pentanal (2b)

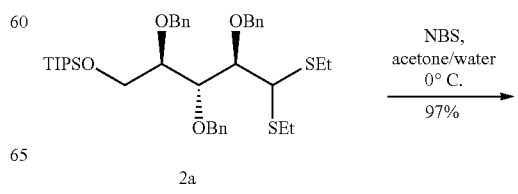

-continued

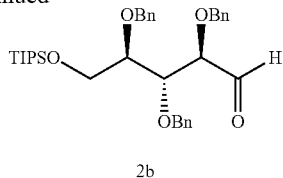

2b

NBS (464 mg, 2.60 mmol) was added to a solution of triisopropyl-((2R,3R,4R)-2,3,4-tris-benzyloxy-5,5-bis ethylsulfanyl-pentyloxy)-silane (356 mg, 0.52 mmol) in a mixture of 5:1 acetone:water (12 mL) and the reaction mixture was stirred for 30 min at 0° C. A saturated aqueous solution of sodium hydrogenocarbonate (5 mL) was added, then a saturated aqueous solution of sodium thiosulfate (5 mL) was added and the mixture was stirred for 15 min. The organic solvent was evaporated off and the remaining aqueous phase was extracted with diethyl ether (2×10 mL). The combined organic phases were dried over magnesium sulfate, evaporated and directly purified by silica gel chromatography (2 g, toluene:hexane 1:1→1:0) to give the title compound as colorless oil (292 mg, 0.50 mmol, 97%).

$[\alpha]_D^{20}$ +12.2 (c 1.5, CHCl$_3$).

$^1$H NMR (300 MHz, CDCl$_3$): δ 9.44 (d, 1H, J=0.9 Hz, CHO), 7.36-7.24 (m, 15H, 3×Ph), 4.85-4.47 (m, 6H, 3×OCH$_2$Ph), 4.10 (dd, 1H, J$_{2,3}$=2.1 Hz, H-2), 4.03-3.91 (m, 2H, H-3, H-5a), 3.84-3.76 (m, 2H, H-4, H-5b), 1.13-0.96 [m, 21H, Si(CHMe$_2$)$_3$].

$^{13}$C NMR (75 MHz, CDCl$_3$): δ 201.41 (CHO q), 138.27, 137.77, 137.59 (3×arom C), 128.46, 128.39, 128.21, 127.94, 127.89, 127.85, 127.80, 127.44 (arom CH), 82.60 (C-2), 80.87 (C-3), 78.63 (C-4), 73.17, 73.11, 72.74 (3×OCH$_2$Ph), 63.53 (C-5), 18.04, 18.03 [Si(CH(CH$_3$)$_2$)$_3$], 11.95 8 [Si(CH (CH$_3$)$_2$)$_3$].

LCMS: [M+H]$^+$ 577.45.

Step 3: O-Benzyl-N-((2S,3S,4R)-2,3,4-tris-benzyloxy-5-triisopropylsilanyloxy-pentyl)-hydroxylamine (2c)

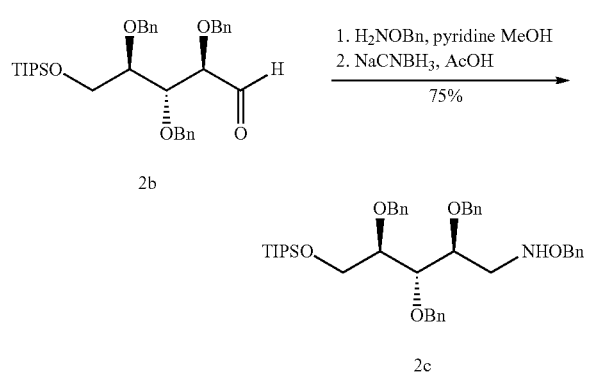

(2R,3R,4R)-2,3,4-Tris-benzyloxy-5-triisopropylsilanyloxy-pentanal (285 mg, 0.49 mmol) and O-benzylhydroxylamine (86 µL, 0.74 mmol) were stirred at 60° C. in 1:6.5 pyridine:MeOH (6 mL) overnight. After 12 h hydroxylamine (20 µL) was added and stirring was continued for further 12 h. The reaction mixture was concentrated and the crude product was purified by chromatography (2 g, hexane:EtOAc 10:1) to give the oxime as colorless oil (317 mg, 0.46 mmol) that was directly used without further purification. The oxime (150 mg, 0.22 mmol) was dissolved in acetic acid (1.5 mL), Sodium cyanoborohydride (124 mg, 1.98 mmol) was added in portions until the starting material was consumed. After 20 minutes the reaction mixture was diluted with water and extracted with dichloromethane (2×5 mL), the organic phases were washed with a saturated aqueous solution of sodium hydrogenocarbonate (5 mL), dried over magnesium sulfate and concentrated. The crude oil was further purified by chromatography (2 g, hexane:EtOAc 15:1) to give the title compound as colorless oil (123 mg, 0.18 mmol, 75% over two steps).

$[\alpha]_D^{20}$ −25.8 (c 1.1, CHCl$_3$).

$^1$H NMR (300 MHz, CDCl$_3$): δ 7.33-7.21 (20H, 4×Ph), 5.92 (bs, H, NH), 4.80-4.48 (m, 8H, 4×OCH$_2$Ph), 4.12 (dt, 1H, J$_{1b,2}$=8.0 Hz, J$_{1a,2}$=3.3 Hz, H-2), 4.00 (dd, 1H, J$_{5a,5b}$=10.7 Hz, J$_{5a,4}$=3.7 Hz, H-5a), 3.88 (dd, 1H, J$_{3,2}$=3.4 Hz, J$_{3,4}$=6.1 Hz, H-3), 3.83 (dd, 1H, J$_{5b,4}$=6.0 Hz, H-5b), 3.62 (dt, 1H, H-4), 3.27 (dd, 1H, J$_{1a,1b}$=13.7 Hz, J$_{1a,2}$=3.3 Hz, H-1a), 3.11 (dd, 1H, J$_{1b,2}$=8.1 Hz, H-1b), 1.14-0.96 [m, 21H, Si(CHMe$_2$)$_3$].

$^{13}$C NMR (75 MHz CDCl$_3$): δ 138.67, 138.56, 138.51, 138.21 (4×arom C), 128.34, 128.28, 128.26, 128.23, 127.92, 127.89, 127.84, 127.61, 127.53, 127.51, 127.41 (arom CH), 80.25 (C-4), 78.67 (C-3), 76.28 (C-2), 75.62 (NOCH$_2$Ph), 73.55, 73.19, 72.20 (3×OCH$_2$Ph), 64.16 (C-5), 52.30 (C-1), 18.06 [Si(CH(CH$_3$)$_2$)$_3$], 11.95 (Si(CH(CH$_3$)$_2$)$_3$).

HRMS ESI$^+$: C$_{42}$H$_{57}$NO$_5$Si [M+H]$^+$ calculated 684.4079. found 684.4078.

Step 4: N-Benzyloxy-N-((2S,3S,4R)-2,3,4-tris-benzyloxy-5-triisopropylsilanyloxy-pentyl)-formamide (2d)

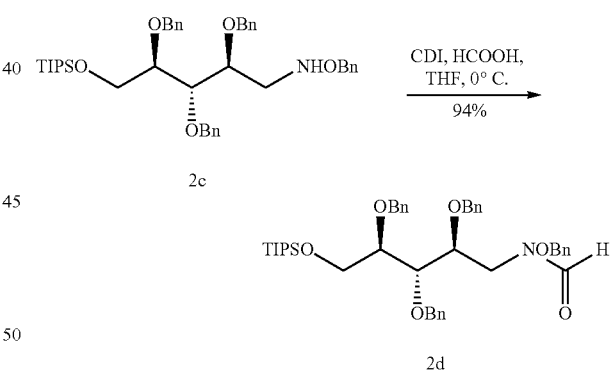

To a solution of carbonyl diimidazole (CDI) (175 mg, 1.08 mmol) in THF (2 mL) at 0° C. was added formic acid (41 µL, 1.08 mmol) and the solution was stirred at 0° C. for 30 minutes. Then a solution of O-benzyl-N-((2S,3S,4R)-2,3,4-tris-benzyloxy-5-triisopropylsilanyloxy-pentyl-hydroxylamine (148 mg, 216 µmol) in THF (1 mL) was added slowly and the solution was stirred at room temperature for 60 minutes until TLC indicated complete conversion. The reaction mixture was concentrated and purified by chromatography (2 g, hexane:EtOAc 3:1) to give the title compound (146 mg, 205 µmol, 94%) as a colorless oil. $[\alpha]_D^{20}$ −5.4 (c 0.9, CHCl$_3$).

$^1$H NMR (600 MHz, toluene, 80° C.): δ 8.07 (bs, 1H, NCHO), 7.33-7.02 (20H, 4×Ph), 4.79-4.55 (m, 8H, 4×OCH$_2$Ph), 4.23-4.19 (m, 1H, H-2), 4.03 (dd, 1H, $J_{5a,5b}$=10.6 Hz, $J_{5a,4}$=3.7 Hz, H-5a), 3.93-3.88 (m, 2H, H-3, H-5b), 3.82-3.71 (m, 3H, H-4, CH$_2$N), 1.08-1.03 [m, 21H, Si(CHMe$_2$)$_3$]. $^{13}$C NMR (150 MHz, toluene-d8, 80° C., HSQC data*): δ 139.54, 139.33, 139.12 (3×arom C, overlapping with toluene signals), 129.56, 129.27, 128.74, 128.70, 128.60, 128.55, 128.36, 128.32, 127.84, 127.80 (arom CH), 81.30 (C-4), 80.10 (C-3), 77.23 (C-2), 77.33 (NOCH$_2$Ph), 73.98, 73.83, 72.29 (3×OCH$_2$Ph), 64.87 (C-5), 48.94* (C-1), 18.42 [Si(CH(Me$_2$)$_3$], 12.76 [Si(CHMe$_2$)$_3$].

HRMS ESI+: C$_{43}$H$_{57}$NO$_6$Si [M+H]+ calculated 712.4028. found 712.4037.

Step 5: N-Benzyloxy-N-((2S,3S,4R)-2,3,4-tris-benzyloxy-5-hydroxy-pentyl)-formamide (2e)

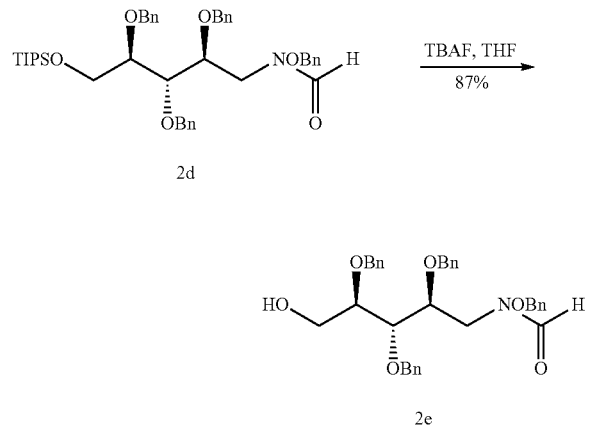

Compound N-benzyloxy-N-((2S,3S,4R)-2,3,4-tris-benzyloxy-5-triisopropylsilanyloxy-pentyl)-formamide (146 mg, 0.20 mmol) was dissolved in dry THF (1 mL) and TBAF (308 μL of a 1 M solution in THF) was added. The mixture was stirred at room temperature for 30 minutes when TLC showed complete conversion. The reaction mixture was concentrated and filtered through a short plug of silica gel (2 g) and was further purified by HPLC (20×250 SIL 06, fraction size 20 mL, flow rate 10 mL, hexane:EtOAc 2:1→1:1) to give the title compound as colorless oil (100 mg, 0.18 mmol, 87%).

[α]$_D^{20}$+44 (c 0.5, CHCl$_3$).

$^1$H NMR (600 MHz, toluene, 80° C.): δ 8.06 (bs, 1H, NCHO), 7.25-7.02 (20H, 4×Ph), 4.65-4.40 (m, 8H, 4×OCH$_2$Ph), 4.12-4.08 (m, 1H, H-2), 3.81 (dd, 1H, J=6.5 Hz, J=2.5 Hz, H-3), 3.75-3.62 (m, 4H, H—H-5a, H-5b, NH$_2$), 3.60-3.56 (m, 1H, H-4).

$^{13}$C NMR (150 MHz, toluene, 80° C.): δ 129.19, 128.91, 128.39, 128.36, 128.34, 128.26, 128.10, 128.00, 127.96 (arom CH), 79.92 (C-4), 79.84 (C-3), 77.11 (NOCH$_2$Ph), 76.94 (C-2*), 73.96, 72.91, 72.56 (3×OCH$_2$Ph), 61.52 (C-5), 48.66* (C-1). *determined by HSQC.

HRMS ESI+: C$_{34}$H$_{37}$NO$_6$ [M+H]+ calculated 556.2694. found 556.2702.

Step 6: Phosphoric acid dibenzyl ester (2R,3S,4S)-2,3,4-tris-benzyloxy-5-(benzyloxy-formyl-amino)-pentyl ester (2f)

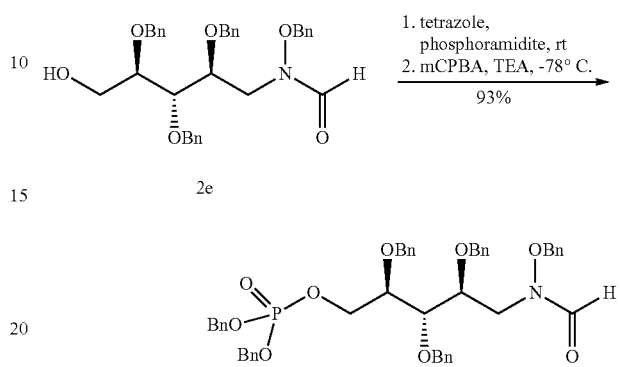

N-Benzyloxy-N-((2S,3S,4R)-2,3,4-tris-benzyloxy-5-hydroxy-pentyl)-formamide (100 mg, 0.18 mmol) was evaporated with toluene two times, dried at high vacuum for 12 h and taken up in anhydrous dichloromethane (1.5 mL, 1.1 ppm). Dibenzyl diisopropylphosphoramidite reagent (91 μL, 0.27 mmol) was added followed by slow addition of 1H-tetrazole (0.45 M in acetonitrile, 600 μL, 0.27 mmol) and the solution was stirred at room temperature for 40 minutes until TLC indicated complete conversion of the starting material. The reaction mixture was then cooled to −78° C., meta-chloroperoxybenzoic acid (70%, 71 mg, 0.28 mmol) was taken up in dichloromethane (1 mL) and added slowly to the reaction mixture which was stirred for 20 minutes at the given temperature. TEA (40 μL, 0.28 mmol) was added and the reaction mixture was allowed to warm to room temperature. The reaction mixture was diluted with dichloromethane (10 mL), washed with a saturated aqueous solution of sodium hydrogenocarbonate (2×, 5 mL), dried over magnesium sulfate and reduced to dryness. The crude was flashed over a short plug of silica gel (2 g, hexane:EtOAc 1:2) and was then purified by HPLC (YMC SIL 06 20×250, hexane: EtOAc 2:1→1:1, flow rate 10 mL) to give the title compound as colorless oil (137 mg, 93%) [α]$_D^{20}$ −44 (c 0.5, CHCl$_3$).

$^1$H NMR (600 MHz, toluene, 80° C.): δ 8.04 (bs, 1H, NCHO), 7.33-6.99 (30H, 6×Ph), 4.95-4.87 (m, 2H, P(O) CH$_2$Ph), 4.66-4.41 (m, 9H, 4×OCH$_2$Ph, H-5a), 4.25-4.20 (m, 1H, H-5b), 4.12-4.09 (m, 1H, H-2), 3.84-3.79 (m, 2H, H-3, H-4), 3.75-3.58 (m, 2H, CH$_2$N).

$^{13}$C NMR (150 MHz, toluene, 80° C.): δ 129.59, 129.28, 128.77, 128.68, 128.65, 128.63, 128.53, 128.50, 128.36 (OCH$_2$Ph CH), 79.56 (C-3), 78.86 ($J_P$=6.2 Hz, C-4), 77.45 (NOCH$_2$Ph), 77.17 (C-2), 74.17, 73.33, 73.19 (3×OCH$_2$Ph), 69.48 (2×POCH$_2$Ph), 67.05 ($J_P$=5.44, C-5), 49.63* (C-1).*determined by HSQC.

HRMS ESI+: C$_{48}$H$_{50}$NO$_9$P [M+Na]+ calcd 838.3115. found 838.3116.

Step 7: N-hydroxy-N-formylamino-1-deoxy-D-ribitol-5-phosphate (monosodium salt)

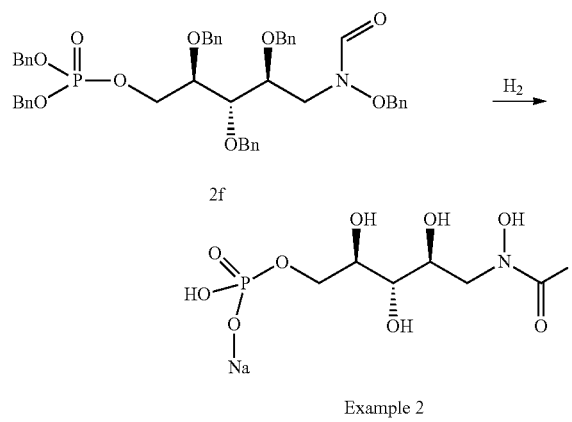

Example 2

Pd/C (10%, 2 mg) was added to a solution of phosphoric acid dibenzyl ester (2R,3S,4S)-2,3,4-tris-benzyloxy-5-(benzyloxy-formyl-amino)-pentyl ester (15 mg, 18 μmol) and sodium hydrogenocarbonate (3.4 mg, 40 μmol) in EtOAc:EtOH:H$_2$O (0.5:1:1) and stirred under hydrogen atmosphere at room temperature and atmospheric pressure for 48 h. The reaction mixture was filtered through a syringe filter, the syringe filter was washed with 6:1 H$_2$O:EtOH (10 mL) and the combined filtrates were lyophilized. Purification on Bio-Gel P2 gave the title compound (2.6 mg, 47%).

$^1$H NMR (600 MHz, D$_2$O for major isomer): δ 7.90 (s, 1H, CHO), 4.14 (ddd, 1H, J$_{2,1a}$=2.8, J$_2$, 1b=8.8, J$_{2,3}$=5.1 Hz, H-2), 3.96 (ddd, 1H, J$_{5b,5a}$=11.3, J$_{5a,4}$=3.2, J$_{P,5a}$=6.5 Hz, H-5a), 3.92 (ddd, 1H, J$_{5b,4}$=5.1, J$_{P,5b}$=7.1 Hz, H-5a), 3.82 (ddd, 1H, J$_{4,3}$=8.2 Hz, H-4), 3.78 (dd, 1H, H-3), 3.72 (dd, 1H, J$_{1a,1b}$=14.9 Hz, H-1a), 3.67 (dd, 1H, H-1b).

$^{13}$C NMR (150 MHz, D$_2$O): δ 160.2 (NCHO), 73.64 (C-3), 72.41 (J$_{C,P}$=6.5 Hz, C-4), 68.66 (C-2), 66.74 (J$_{C,P}$=4.4 Hz, C-5), 54.27 (C-1).

$^{31}$P NMR (242 MHz, D$_2$O): δ 2.97, 2.92.

LCMS [M−H]$^-$: 273.90.

Example 3: [6-(Formyl-hydroxy-amino)-(3R,4R,5S)-3,4,5-trihydroxy-hexyl]-phosphonic acid (monosodium salt)

Synthesis Method I

Step 1: 2,3,4-Tri-O-benzyl-1-(N-benzyloxy-N-formylamino)-1-deoxy-5-oxo-D-ribitol (3a)

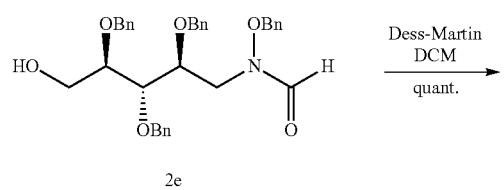

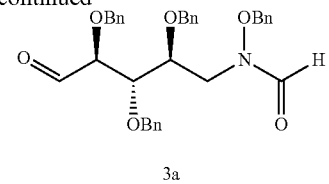

To a solution of 2e (170 mg, 0.31 mmol, obtained as in Example 2, step 5) in DCM (4 mL), Dess-Martin reagent (200 mg, 0.46 mmol) was added. Reaction was stirred at RT for 1 h (TLC; EtOAc/Hex 1:3). After completion, the crude was diluted with DCM, washed with satd. aq. sol of NaHCO$_2$ and Na$_2$S$_2$O$_2$. The organic phase was finally washed with brine, dried and concentrated to give the crude product, which was stored under Ar atmosphere at −78° C. Yield: 168 mg, (quant.) of aldehyde 3a as a colorless syrup. [α]$_D^{20}$ +4.9 (c 0.61, CHCl$_3$);

$^1$H NMR (300 MHz, CDCl$_3$): δ 9.47 (s, 1H, CHO), 8.28-7.26 (m, 21H, H—Ar, H-formyl), 5.30 (s, 0.4H), 5.06-4.40 (br. m, 8H, CH$_2$Ar), 4.31-3.20 (br. m, 5H, H-2, H-3, H-4, H-1a, H-1b). HR-MS: calculated for C$_{34}$H$_{35}$NO$_6$ [M+Na]+: 576.2357. found 576.2365.

Step 2: Dibenzyl [2,3,4-tri-O-benzyl-1-(N-benzyloxy-N-formylamino)-1-deoxy-D-ribo-5(E)-hexenitol] 6-phosphonate (3b)

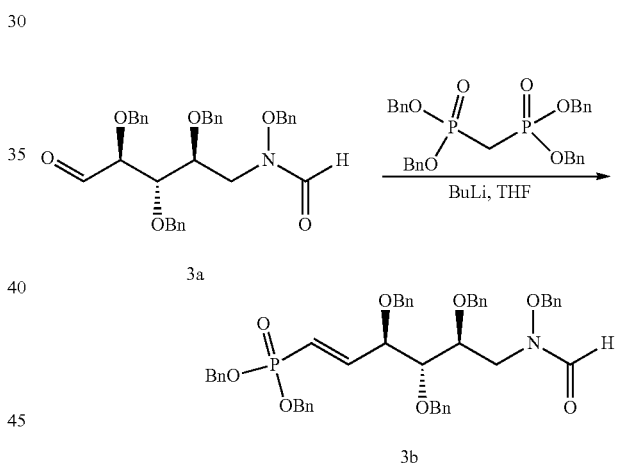

The (Bis-benzyloxy-phosphorylmethyl)-phosphonic acid dibenzyl ester (450 mg, 0.84 mmol, obtained as described in *Bioorg. Med. Chem. Lett.*, 2008, 18, 4789) was dissolved in THF (2 mL) and cooled to −78° C. Then BuLi (0.35 mL, 0.8 mmol) was added dropwise and the reaction mixture was stirred at the same temperature for 30 min. Then aldehyde 121 (235 mg, 0.042 mmol) was added in one portion and the reaction was stirred for 90 min and checked by TLC (EtOAc/Hex 1:2). After stirring overnight at room temperature the solution was quenched by adding an aq NH$_4$Cl. The suspension was extracted into EtOAc, washed with brine, dried and concentrated. Purification by column chromatography EtOAc/Hex 1:2 gave compound 38. Yield: 225 mg, (76%); [α]$_D^{20}$+3.3 (c=0.72, CHCl$_3$). $^1$H NMR (toluene-d6. 70°): δ 8.04 (s, 1H, HC=O), 7.28-6.91 (m, 31H, 30×H—Ar, H-5), 6.08 (m, 1H, H-6), 4.95-4.89 (m, 4H, 2×CH$_2$—Ar), 4.60-4.50 (m, 4H, 2×CH$_2$—Ar), 4.44 (AB, 2H, CH$_2$—Ar), 4.29 (AB, 2H, CH$_2$—Ar), 4.13 (bt, 1H, H-4), 3.98 (bt, 1H, H-2), 3.67 (m, 3H, H-3, H-1a, H-1b), $^{13}$C NMR (toluene-d$_8$, 70°): δ 149.4 (C-formyl), 137.1 (6×C-pAr), 129.0-124.3 (24×CAr), 121.5 (C-5), 120.3 (C-6), 81.6 (C-3), 79.6 (C-4), 77.2 (C-2), 76.7 (CH$_2$—Ar), 73.6, 72.6, 71.9 (3×CH$_2$—Ar), 66.9 (CH$_2$—Ar), 47.3 (C-1). HR-MS: C$_{56}$H$_{47}$N$_2$O$_4$P [M+H]$^+$ calc: 812.3609. found: 812.3623.

Step 3: [6-(Formyl-hydroxy-amino)-(3R,4R,5S)-3,4,5-trihydroxy-hexyl]-phosphonic acid (Example 3)

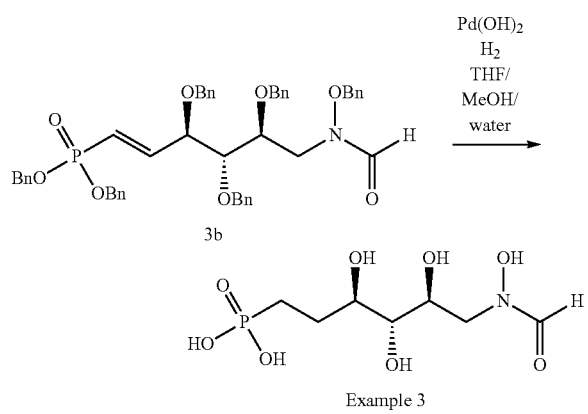

Compound 3b (35 mg, 0.04 mmol) was dissolved in 1 mL of a mixture THF/MeOH/water (1:1:2) and catalyst Pd(OH)$_2$—C(7 mg, 20% w/w) was added. The reaction was stirred under hydrogen atmosphere over the weekend at room temperature. Then TLC (EtOAc/MeOH 3:1 and Chloroform/MeOH/water 10:10:3) showed several spots. Every 24 h a new portion of catalyst (always 7 mg) was added. After 72 h most of the product had been formed according to LC-MS. The suspension was filtered and the filtrate was concentrated. The residue was treated with 2.1 eq. of aq. sodium bicarbonate and filtered. The filtrate was concentrated and finally lyophilised. Purification on HILIC column (2×) gave 1 mg of final compound 39 (B1) [α]$_D^{20}$ −34.7 (c 0.21, water); $^1$H NMR (600 MHz, D$_2$O, ratio of rotamers 5.5:1): δ 8.42 (s, H-formyl minor rotamer), 7.97 (s, H-formyl major rotamer), 4.15 (ddd, 1H, J=2.5, J=5.9 Hz, H-2), 3.79 (dd, 1H, J=2.5, J=14.9 Hz, H-1a), 3.76 (ddd, 1H, J=2.6, J=6.3, J=9.1 Hz, H-4), 3.72 (dd, 1H, J=9.2, J=15.0 Hz, H-1b), 3.69 (dd, 1H, H-3), 1.96 (dddd, 1H, J=2.8, J=4.6, J=11.9 Hz, H-5a), 1.83 (ddd, 1H, J=4.5, J=11.9 Hz, H-6a), 1.69 (dddd, 1H, J=4.6, J=9.1 Hz, H-5b), 1.61 (ddd, 1H, J=4.6, J=11.5 Hz, H-6b). $^{31}$P NMR: δ 25.47. $^{13}$C NMR (150 MHz, D$_2$O): δ 160.9 (CHO), 76.0 (C-3), 72.8 (d, C-4), 68.2 (C-2), 54.0 (C-1), 27.2 (C-5), 25.3 (C-6). HR-MS: C$_7$H$_{16}$NO$_8$P [M]$^-$ calc: 272.0541. found: 272.0552.

Synthesis Method II

Step 1: Methyl(1R,2R,3R,4R)-2,3-O-isopropylidene-5-O-trifluoromethanesulfonyl-beta-D-ribofuranoside (3-II-a)

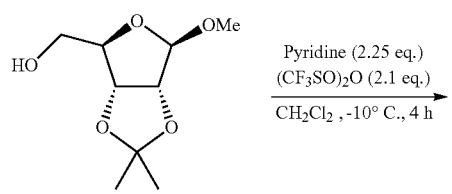

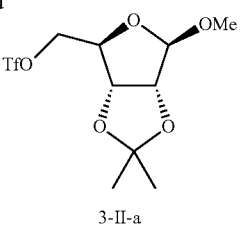

A solution of Pyridine (4.4 mL, 54 mmol) in anhydrous CH$_2$Cl$_2$ (200 mL) under nitrogen atmosphere was cooled to −10° C. A solution of trifluoromethanesulfonic anhydride (8.6 mL, 50.3 mmol) in CH$_2$Cl$_2$ (30 mL) was added via a syringe pump in 30 min. During addition, a white suspension appeared. Then, a solution of Methyl 2,3-O-isopropylidene-beta-D-ribofuranoside (5 g, 23.99 mmol) in CH$_2$Cl$_2$ (32 mL) was added via a syringe pump in 30 min. The resulting solution was stirred further 3 hours at −10° C. until TLC (cyclohexane:EtOAc 80:20) indicated complete conversion. The reaction mixture was quenched with cold H$_2$O (250 mL) and the layers were separated. The organic layer was washed with saturated aqueous NaHCO$_3$ (100 mL), then with H$_2$O (2×100 mL). The organic layer was dried over Na$_2$SO$_4$, filtered and concentrated under reduced pressure to give the title compound 3-II-a (7.75 g, 20.7 mmol, 86% isolated yield) as a slightly pink oil (assay=90%, estimated by $^1$H NMR).

$^1$H NMR (250 MHz, CDCl$_3$): δ 5.0 (s, 1H, O—C$\underline{H}$—OCH$_3$), 4.68 (d, 1H, J=6 Hz), 4.62 (d, 1H, J=6 Hz), 4.47 (br s, 3H), 3.36 (s, 3H, OC$\underline{H}_3$), 1.49 (s, 3H, C—C$\underline{H}_3$), 1.32 (s, 3H, C—C$\underline{H}_3$)

$^{19}$F NMR (235 MHz, CDCl$_3$): δ −74.5 (C$\underline{F}_3$)

Step 2: [2-(3R,4R,5R,6R)-(6-Methoxy-2,2-dimethyl-tetrahydro-furo[3,4-d][1,3]dioxol-4-yl)-ethyl]-phosphonic acid dimethyl ester (3-II-b)

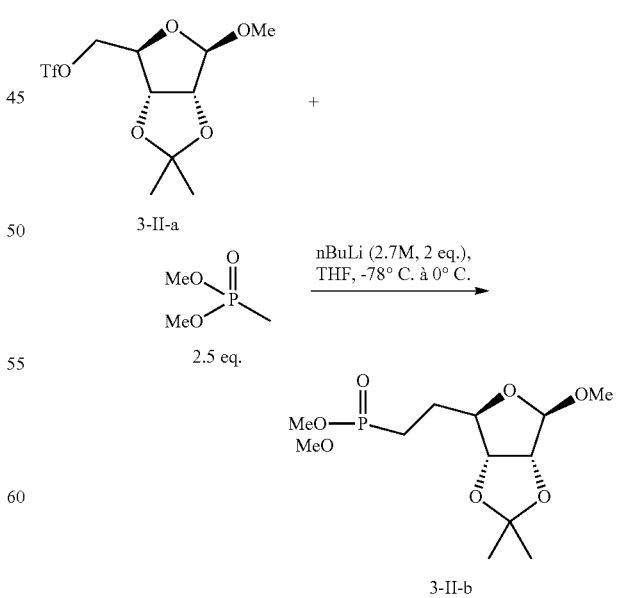

A stirred solution of Dimethyl methylphosphonate (3.42 g, 26.8 mmol) in anhydrous THF (26 mL) under nitrogen atmosphere was cooled to −78° C. nBuLi (2.7M in hexane, 7.93 mL, 21.42 mmol) was added via syringe pump over 10 min. During addition, reaction mixture turned to yellow. At −78° C., a solution of (3-II-a) (4.0 g, 10.71 mmol) in THF (11 mL) was added over 10 min via syringe pump and the reaction mixture was stirred further for 1 hour at −78° C. The reaction mixture was quenched with NH$_4$Cl (50 mL) and the layers were separated. The aqueous layer was extracted three times with EtOAc (3×50 mL). The organic layers were combined, dried over Na$_2$SO$_4$, filtered and concentrated under reduced pressure. The residue was purified by chromatography (SiO$_2$ column 160 g, cyclohexane:EtOAc 10:90 to 80:20) to give the title compound (2.61 g, 8.0 mmol, 75% isolated yield) as a colorless oil (assay=95%, estimated by $^1$H NMR).

$^1$H NMR (250 MHz, CDCl$_3$): δ 4.95 (s, 1H, O—C$\underline{H}$—OCH$_3$), 4.61 (d, 1H, J=5 Hz), 4.54 (br d, 1H, J=5 Hz), 4.17-4.10 (m, 1H), 3.76 (s, 3H, POC$\underline{H_3}$), 3.73 (s, 3H, POC$\underline{H_3}$), 3.34 (s, 3H, OC$\underline{H_3}$), 1.99-1.77 (m, 4H, C$\underline{H_2}$—C$\underline{H_2}$), 1.47 (s, 3H, C—C$\underline{H_3}$), 1.31 (s, 3H, C—C$\underline{H_3}$)

Step 3: [(2R,3R,4R)-2-(3,4,5-Trihydroxy-tetrahydro-furan-2-yl)-ethyl]-phosphonic acid dimethyl ester (3-II-c)

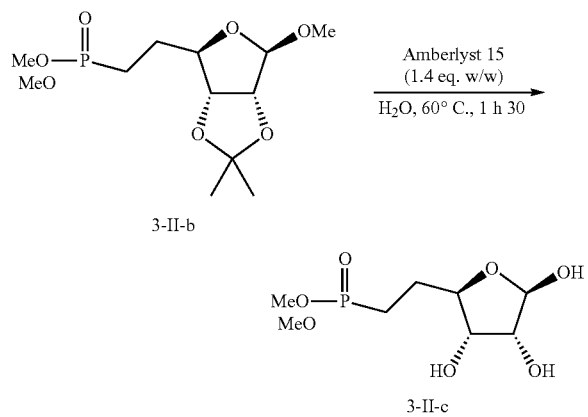

To a stirred solution of compound 3-II-b (2.04 g, 5.91 mmol) in H$_2$O (10 mL) at 22° C. was added Amberlyst 15 (2.9 g, previously washed with H$_2$O, 1.4 eq. w/w). The resulting suspension was stirred at 60° C. for 1.5 hour until TLC (EtOAc:MeOH 80:20) and LC-MS (APCI$^+$) indicated complete conversion. The reaction mixture was filtered and the resin was washed with H$_2$O. pH was adjusted to pH=6.9 by adding 0.1M NaOH aq. solution. The solution was concentrated to approximately 3 mL to give the title compound (5.91 mmol theoretical) in solution in H$_2$O which was used without further purification in the next step. The compound was obtained as a mixture of diastereomers in a ratio 3:1.

$^1$H NMR (250 MHz, D$_2$O): δ 5.37 (br s, 0.25H, O—C$\underline{H}$—OH, minor diastereomer), 5.22 (br s, 0.75H, O—C$\underline{H}$—OH, major diastereomer), 4.12-3.93 (m, 3H), 3.79 (br s, 3H, OC$\underline{H_3}$), 3.76 (br s, 3H, OC$\underline{H_3}$), 2.12-1.75 (m, 4H, C$\underline{H_2}$—C$\underline{H_2}$)

LC-MS APCI$^+$: C$_8$H$_{18}$O$_7$P [M+H]$^+$ calculated 257.1. found 257.1.

Step 4: (6-Benzyloxyimino-(3R,4R,5R)-3,4,5-trihydroxy-hexyl)-phosphonic acid dimethyl ester (3-II-d)

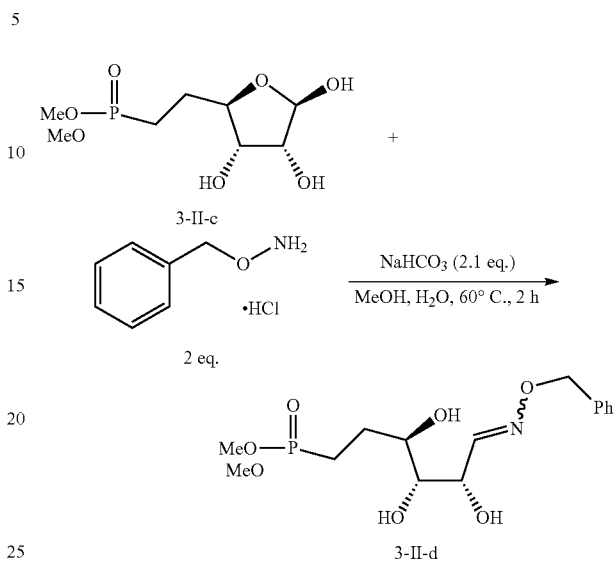

To a stirred solution of compound 3-II-c (5.9 mmol) in H$_2$O (3 mL) obtained from previous step, was added MeOH (8 mL). Benzylhydroxylamine*HCl (1.92 g, 11.8 mmol) and then NaHCO$_3$ (1.05 g, 12.4 mmol) were added and the solution was heated to 60° C. and stirred for 2 h until TLC (CH$_2$Cl$_2$:MeOH 90:10) indicated complete conversion. The reaction mixture was concentrated under reduced pressure. CH$_3$CN (30 mL) was added to the residue and the suspension was filtered. The filtrate was concentrated under reduced pressure and the residue was purified by chromatography (SiO$_2$ column 40 g, EtOAc:MeOH 99:1 to 97:3) to give the title compound (1.23 g, 3.06 mmol, 52% isolated yield over two steps) as a colorless oil (assay=90%, estimated by $^1$H NMR). The compound was obtained as a mixture of Oxime E and Z: 4:1.

$^1$H NMR (300 MHz, D$_2$O): δ 7.63 (d, 0.8H, J=4.5 Hz, $\underline{H}$C=NOBn, E), 7.40-7.26 (m, 5H, Ph), 6.92 (d, 0.2H, J=6 Hz, $\underline{H}$C=NOBn, Z), 5.12 (br s, 0.4H, CH$_2$-Ph, Z), 5.08 (br s, 1.6H, CH$_2$-Ph, E), 4.40 (t app., 1H, J=5.5 Hz), 4.01-3.56 (m, 5H), 3.75 (br s, 3H, OC$\underline{H_2}$), 3.70 (br s, 3H, OC$\underline{H_2}$), 2.07-1.73 (m, 4H, C$\underline{H_2}$—C$\underline{H_2}$)

LC-MS APCI$^+$: C$_{15}$H$_{25}$NO$_7$P [M+H]$^+$ calculated 362.1 found 362.3.

Step 5: (6-Benzyloxyamino-(3R,4R,5S)-3,4,5-trihydroxy-hexyl)-phosphonic acid dimethyl ester (3-II-e)

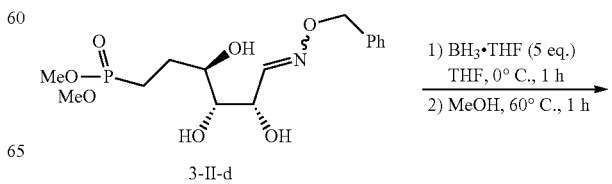

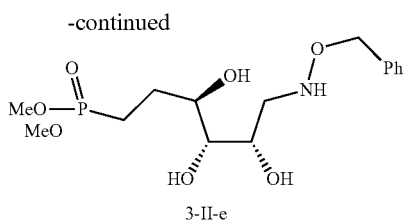

3-II-e

To a stirred solution of oxime 3-II-d (910 mg, 2.27 mmol) in THF (11 mL) at 0° C. under nitrogen atmosphere was added dropwise BH$_3$*THF (1M, 11.3 mL, 11.3 mmol) over 10 min. The solution was stirred further at 0° C. for 2 hours until TLC (EtOAc:MeOH 95:5) and LC-MS indicated complete conversion. The reaction mixture was quenched carefully with MeOH (10 mL) at 0° C. (H$_2$ emission) and then heated at 60° C. for 1 hour. After cooling, the reaction mixture was concentrated under reduced pressure and the residue was purified by chromatography (SiO$_2$ column 40 g, EtOAc:MeOH 97:3 to 90:10) to give the title compound (615 mg, 1.61 mmol, 71% isolated yield) as a colorless oil (assay=95%, estimated by $^1$H NMR).

$^1$H NMR (250 MHz, D$_2$O): δ 7.39 (br s, 5H, Ph), 4.73 (s, 2H, OCH$_2$Ph), 3.95-3.88 (m, 1H), 3.75 (s, 3H, OMe), 3.70 (s, 3H, OMe), 3.66-3.59 (m, 1H), 3.51 (dd, 1H, J=6.0, 6.1 Hz), 3.21 (dd, 1H, J=13.8, 2.5 Hz), 2.81 (dd, 1H, J=13.8, 9.2 Hz), 2.18-1.80 (m, 3H), 1.70-1.50 (m, 1H)

LC-MS APCI$^+$: C$_{15}$H$_{27}$NO$_7$P [M+H]$^+$ calculated 364.15. found 364.02.

Step 6: [6-(Benzyloxy-formyl-amino)-(3R,4R,5S)-3,4,5-trihydroxy-hexyl]-phosphonic acid dimethyl ester (3-II-f)

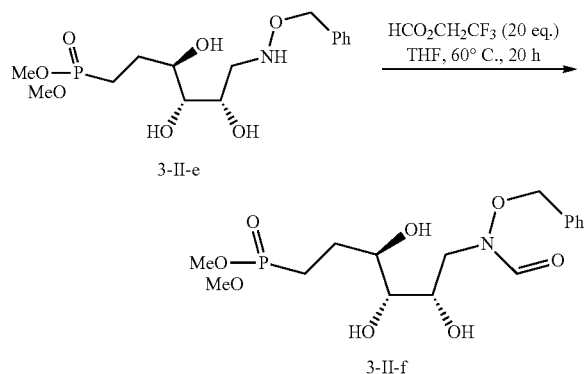

To a stirred solution of Hydroxylamine 3-II-e (580 mg, 1.52 mmol) in THF (3 mL) at 23° C. under nitrogen atmosphere was added trifluoroethyl formate (3.1 mL, 30.3 mmol). The solution was heated at 60° C. and stirred for 20 hours until TLC (CH$_2$Cl$_2$:MeOH 95:5) and LC-MS indicated complete conversion. After cooling at 23° C., the reaction mixture was concentrated under reduced pressure and the residue was purified by chromatography (SiO$_2$ column 40 g, CH$_2$Cl$_2$: MeOH 97:3 to 95:5) to give the title compound (460 mg, 1.12 mmol, 74% isolated yield) as a slightly yellow oil (assay=95%, estimated by $^1$H NMR).

$^1$H NMR (250 MHz, D$_2$O): δ 8.10 (s, 0.26H, NC(=O)H, minor rotamer), 7.88 (s, 0.7H, NC(=O)H, major rotamer), 7.50-7.40 (m, 5H, Ph), 4.95 (s, 2H, OCH$_2$Ph), 4.02-3.80 (m, 1.7H), 3.75 (s, 3H, OMe), 3.70 (s, 3H, OMe), 3.68-3.59 (m, 2H), 3.57-3.45 (m, 1.3H), 2.18-1.80 (m, 3H), 1.70-1.57 (m, 1H)

LC-MS APCI$^+$: C$_{16}$H$_{26}$NO$_8$P [M+H]$^+$ calculated 392.15. found 391.9.

Step 7: [6-(Formyl-hydroxy-amino)-(3R,4R,5S)-3,4,5-trihydroxy-hexyl]-phosphonic acid dimethyl ester (3-II-g)

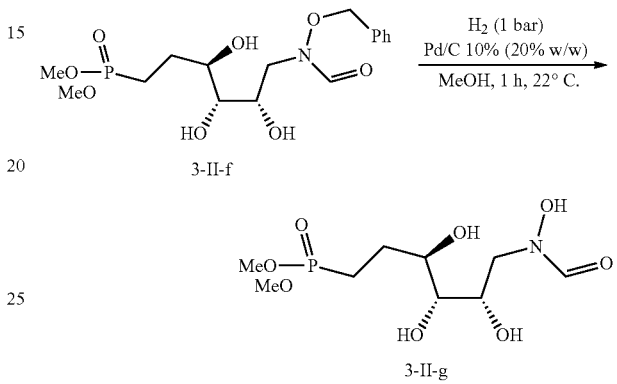

In an autoclave, compound 3-II-f (93 mg, 0.23 mmol) was dissolved in MeOH (0.9 mL). Pd/C 10% Degussa type E101 (19 mg, 20% w/w) was added. The autoclave was purged three times with nitrogen (2 bar) and then three times with H$_2$ (2 bar). The pressure was set to 1 bar of H$_2$ and the reaction mixture was stirred at 22° C. for 1 hour. The autoclave was depressurized and purged with nitrogen. The reaction mixture was filtered over Celite® pad and the residue concentrated under reduced pressure to give the title compound (72 mg, 0.22 mmol, 95% isolated yield) as a slightly yellow oil (assay=95%, estimated by $^1$H NMR) which was used without further purification.

$^1$H NMR (250 MHz, D$_2$O): δ 8.33 (s, 0.16H, NC(=O)H, minor rotamer), 7.88 (s, 0.8H, NC(=O)H, major rotamer), 4.06-3.99 (m, 1H), 3.76 (s, 3H, OMe), 3.71 (s, 3H, OMe), 3.73-3.66 (m, 2H), 3.63-3.57 (m, 2H), 2.16-1.83 (m, 3H), 1.74-1.55 (m, 1H)

$^{15}$N NMR (50 MHz, D$_2$O): δ 172 ppm (d, $^2$J=25 Hz)

LC-MS ESI$^+$: C$_9$H$_{20}$NNaO$_8$P [M+Na]$^+$ calculated 324.1. found 323.8.

Step 8: [6-(Formyl-hydroxy-amino)-(3R,4R,5S)-3,4,5-trihydroxy-hexyl]-phosphonic acid (monosodium salt)

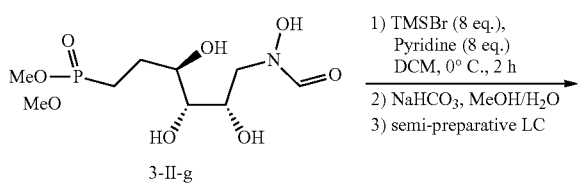

3-II-g

1) TMSBr (8 eq.), Pyridine (8 eq.) DCM, 0° C., 2 h
2) NaHCO$_3$, MeOH/H$_2$O
3) semi-preparative LC -continued

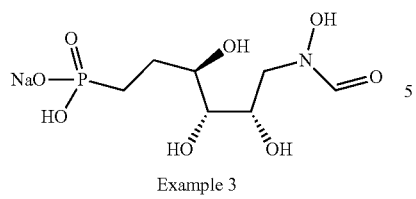

Example 3

-continued

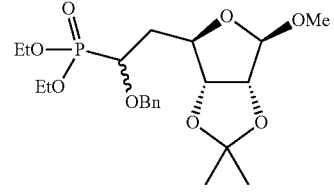

4a

To a stirred suspension of 3-II-g (80 mg, 0.25 mmol) in anhydrous CH$_2$Cl$_2$ (5 mL) at 0° C. under nitrogen atmosphere was added Pyridine (173 μL, 2.1 mmol). TMSBr (290 μL, 2.1 mmol) was added dropwise over 5 min and the reaction mixture was stirred at 0° C. for 2 hours until LC-MS (ESI$^-$) indicated complete conversion. The reaction mixture was concentrated under reduced pressure at 0° C. Water (2 mL) and MeOH (2 mL) were added to the residue at 0° C. and the mixture was neutralized with an aqueous solution of NaHCO$_3$ up to pH=7.5. The solution was stirred at 20° C. until complete desilylation as determined by LC-MS (ESI$^-$). The reaction mixture was then lyophilized and the resulting powder was purified by semi-preparative liquid chromatography (Column: Modulocart QS Strategy 10RP 21.2×250 mm, InterChim, gradient H$_2$O:CH$_3$CN 3:97 to 40:60 over 15 min, flow rate 12 mL/min, fraction size 5 mL, Detector: MS-ESI$^-$) to give the title compound (51 mg, 0.16 mmol, 64%) as a yellow solid (assay=95%, estimated by $^1$H NMR; Area %=94%, TIC Mode in LC-MS).

$^1$H NMR (250 MHz, D$_2$O): δ 8.33 (s, 0.15H, NC(=O)H, minor rotamer), 7.89 (s, 0.8H, NC(=O)H, major rotamer), 4.08-4.02 (m, 1H), 3.74-3.54 (m, 4H), 1.95-1.73 (m, 2H, CH$_2$—CH$_2$), 1.69-1.44 (m, 2H CH$_2$—CH$_2$)

$^{31}$P NMR (101 MHz, D$_2$O): δ 25.8 ppm

LC-MS ESI$^-$: C$_7$H$_{15}$NO$_8$P [M-H]$^-$ calculated 272.0. found 272.1.

Example 4: [[6-(Formyl-hydroxy-amino)-(3R,4R,5S)-1,3,4,5-tetra-hydroxy-hexyl]-phosphonic acid (monosodium salt)

Step 1: [1-Benzyloxy-2-(3R,4R,5R,6R)-(6-methoxy-2,2-dimethyl-tetrahydro-furo[3,4-d][1,3]dioxol-4-yl)-ethyl]-phosphonic acid diethyl ester (4a)

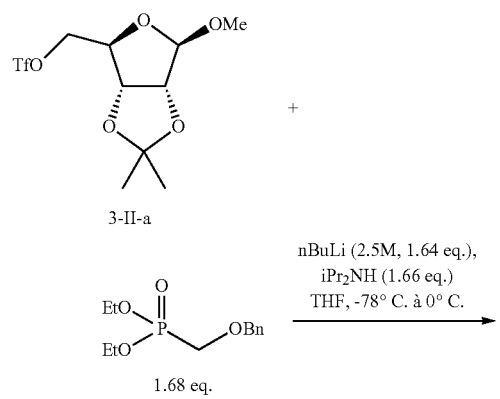

A stirred solution of diisopropylamine (1.71 g, 16.9 mmol) in anhydrous THF (12 mL) under nitrogen atmosphere was cooled to −78° C. nBuLi (2.5M in hexane, 6.7 mL, 16.7 mmol) was added dropwise over 15 min via syringe pump and the reaction mixture was warmed to −10° C. in 30 min and stirred at this temperature for further 30 min. The solution was cooled to −78° C. and a solution of (phenylmethoxy)-methyl-phosphonic acid diethyl ester (4.9 g, 17.1 mmol) in THF (11 mL) was added over 15 min via syringe pump. A white suspension appeared during the addition. After five minutes a solution of methyl(1R,2R,3R,4R)-2,3-O-isopropylidene-5-O-trifluoromethanesulfonyl-beta-D-ribofuranoside 3-II-a (3.8 g, 10.2 mmol, obtained as in Example 3, synthesis method II, Step 1) in THF (17 mL) was added to the suspension at −78° C. over ten minutes via syringe pump and then the solution was warmed over 1 h at 0° C. The reaction mixture was quenched with NH$_4$Cl (50 mL) and the layers were separated. The aqueous layer was extracted three times with EtOAc (3×50 mL). The organic layers were combined, dried over Na$_2$SO$_4$, filtered and concentrated under reduced pressure. The residue was purified by chromatography (SiO$_2$ column 200 g, cyclohexane:EtOAc 50:50) to give the title compound (2.9 g, 6.2 mmol, 61% isolated yield) as a colorless oil (assay=95%, estimated by $^1$H NMR). The compound was obtained as a mixture of diastereomers in a ratio 2:1.

$^1$H NMR (250 MHz, CDCl$_3$): δ 7.40-7.28 (m, 5H, Ph), 5.0 (br dd, 0.6H, J=1.0, 10.5 Hz, major diastereomer), 4.94 (br s, 0.6H, major diastereomer), 4.93 (br s, 0.4H, minor diastereomer), 4.90 (br d, 0.4H, J=11.0 Hz, minor diastereomer), 4.64-4.56 (m, 3H), 4.45-4.39 (m, 1H), 4.22-4.13 (m, 4H, 2×OCH$_2$CH$_3$), 3.97 (ddd, 0.6H, J=2.5, 3.8, 10.8 Hz, major diastereomer), 3.85-3.77 (m, 0.4H, minor diastereomer), 3.33 (s, 1.8H, OCH$_3$, major diastereomer), 3.28 (s, 1.2H, OCH$_3$, minor diastereomer), 2.12-1.86 (m, 2H, CH—CH$_2$), 1.48 (s, 1.8H, major diastereomer), 1.47 (s, 1.2H, minor diastereomer), 1.38-1.30 (m, 9H)

LC-MS EST$^+$: C$_{21}$H$_{34}$O$_8$P [M+H]$^+$ calculated 445.2. found 444.8. [M+NH$_4$]$^+$ found 461.8.

Step 2: [1-Hydroxy-2-(3R,4R,5R,6R)-(6-methoxy-2,2-dimethyl-tetrahydro-furo[3,4-d][1,3]dioxol-4-yl)-ethyl]-phosphonic acid diethyl ester (4b)

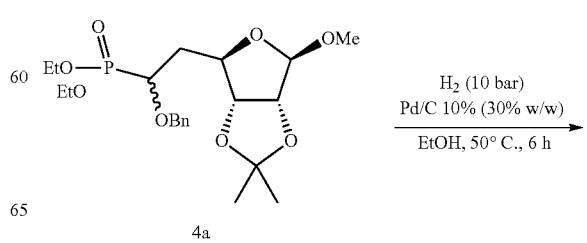

4a

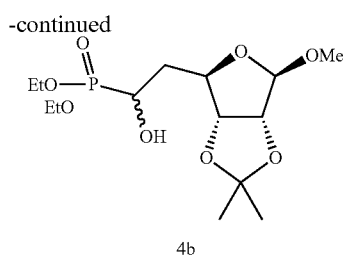

In an autoclave, compound 4a (1.2 g, 2.56 mmol) was dissolved in EtOH (6 mL). Pd/C 10% Degussa type E101 (360 mg, 30% w/w) was added. The autoclave was purged three times with nitrogen (5 bar) and then three times with H$_2$ (5 bar). The pressure was set to 10 bar of H$_2$ and the reaction mixture was stirred at 50° C. for 6 hours. The autoclave was depressurized and purged with nitrogen. The reaction mixture was filtered over Celite® pad and the residue concentrated under reduced pressure to give the title compound (953 mg, 2.42 mmol, 95% isolated yield) as a colorless oil (assay=95%, estimated by $^1$H NMR) which was used without further purification. The compound was obtained as a mixture of diastereomers in a ratio 3:1.

$^1$H NMR (250 MHz, D$_2$O): δ 5.0 (s, 1H), 4.77-4.74 (m, 1H), 4.45-4.40 (m, 1H), 4.24-4.04 (m, 6H, 2×OCH$_2$CH$_3$+2H), 3.35 (s, 3H, OCH$_3$), 2.06-1.83 (m, 2H, CH—CH$_2$), 1.45 (s, 3H, CH$_3$), 1.32-1.27 (m, 9H, CH$_3$+2×OCH$_2$CH$_3$)

LC-MS ESI$^+$: C$_{14}$H$_{28}$O$_8$P [M+H]$^+$ calculated 355.1. found 355.0.

Step 3: [1-Hydroxy-(3R,4R,5R)-2-(3,4,5-trihydroxy-tetrahydro-furan-2-yl)-ethyl]-phosphonic acid diethyl ester (4c)

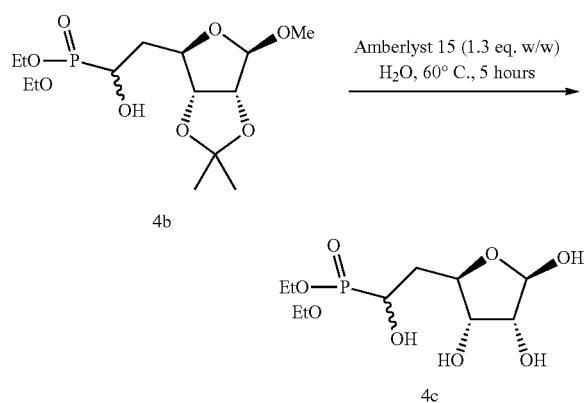

To a stirred solution of compound 4b (606 mg, 1.54 mmol) in H$_2$O (3 mL) at 22° C. was added Amberlyst 15 (788 mg, previously washed with H$_2$O, 1.3 eq. w/w). The resulting suspension was stirred at 60° C. for 5 hours until TLC (AcOEt:MeOH 90:10) and LC-MS (ESI$^+$) indicated complete conversion. The reaction mixture was filtered and the resin was washed with H$_2$O. pH was adjusted to pH=6.5 by adding 0.1M NaOH aq. solution. The solution was concentrated to approximately 3 mL to give the title compound (1.54 mmol theoretical) in solution in H$_2$O which was used without further purification. The compound was obtained as a mixture of diastereomers in a ratio 3:1.

$^1$H NMR (250 MHz, D$_2$O): δ 5.34-5.20 (m, 1H), 4.95-4.94 (m, 1H), 4.23-4.06 (m, 6H, 2×OCH$_2$CH$_3$+2H), 4.01-3.93 (m, 1H), 2.12-1.77 (m, 2H, CH—CH$_2$), 1.30 (t, 6H, J=7 Hz, 2×OCH$_2$CH$_3$)

LC-MS ESI$^+$: C$_{10}$H$_{22}$O$_8$P [M+H]$^+$ calculated 301.1. found 300.9, [M+Na]$^+$ calculated 323.1. found 322.9.

Step 4: (6-Benzyloxyimino-(3R,4R,5R)-1,3,4,5-tetrahydroxy-hexyl)-phosphonic acid diethyl ester (4d)

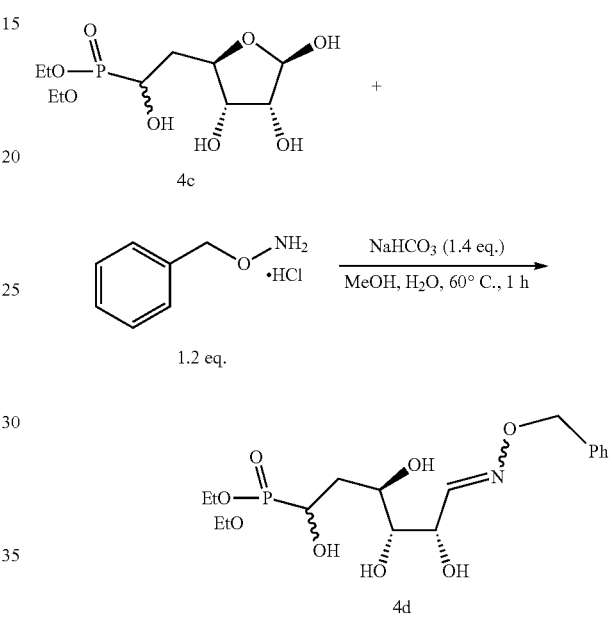

To a stirred solution of compound 4c (1.53 mmol) in H$_2$O (3 mL) obtained from previous step, was added EtOH (3 mL). Benzylhydroxylamine.HCl (296 mg, 1.84 mmol) and then NaHCO$_3$ (182 mg, 2.14 mmol) were added and the solution was heated to 60° C. and stirred for 1 h until TLC (CH$_2$Cl$_2$:MeOH 95:5) indicated complete conversion. The reaction mixture was concentrated under reduced pressure and the residue was purified by chromatography (SiO$_2$ column 15 g, CH$_2$Cl$_2$:MeOH 95:5) to give the title compound (384 mg, 0.85 mmol, 56% isolated yield over two steps) as a colorless oil (assay=90%, estimated by $^1$H NMR). The compound was obtained as a mixture of diastereomers in a ratio 3:1 and a mixture of oxime E and Z: 9:1.

$^1$H NMR (250 MHz, D$_2$O): δ 7.56 (d, 0.7H, J=6.5 Hz, HC═NOBn, major diastereomer, E), 7.54 (d, 0.3H, J=6.5 Hz, HC═NOBn, minor diastereomer, E), 7.47-7.31 (m, 5H, Ph), 6.88 (d, 0.08H, J=6 Hz, HC═NOBn, major diastereomer, Z), 6.86 (d, 0.04H, J=6 Hz, HC═NOBn, minor diastereomer, Z), 5.1 (s, 2H, OCH$_2$Ph), 4.33 (dd, 0.9H, J=5.2, 6.5 Hz, E), 4.23-4.07 (m, 5.1H, 2×OCH$_2$CH$_2$+H), 3.88-3.75 (m, 1H), 3.73-3.65 (m, 1H), 3.35 (d, 0.1H, J=4.2 Hz, Z), 2.20-1.66 (m, 2H), 1.30 (t, 6H, J=7.0 Hz, 2×OCH$_2$CH$_3$)

LC-MS APCI$^+$: C$_{22}$H$_{29}$NO$_8$P [M+H]$^+$ calculated 406.2. found 406.2.

Step 5: (6-Benzyloxyamino-(3R,4R,5S)-1,3,4,5-tetrahydroxy-hexyl)-phosphonic acid diethyl ester (4e)

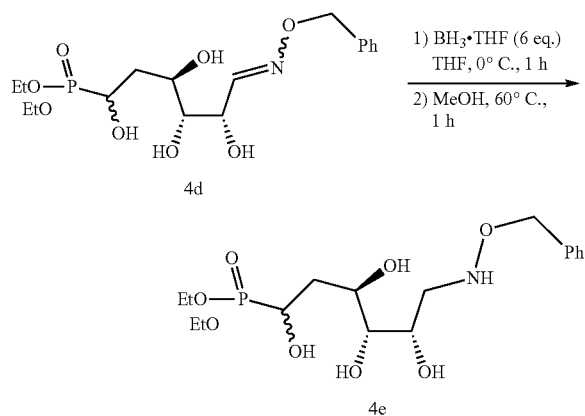

To a stirred solution of oxime 4d (384 mg, 0.85 mmol) in THF (5 mL) at 0° C. under nitrogen atmosphere was added dropwise BH₃.THF (1M, 5.1 mL, 5.1 mmol) via syringe pump over 10 min. The solution was stirred further at 0° C. for 1 hour until TLC (CH₂Cl₂:MeOH 90:10) and LC-MS (APCI⁺) indicated complete conversion. The reaction mixture was quenched carefully with MeOH (10 mL) at 0° C. (H₂ emission) and then heated at 60° C. for 1 hour. After cooling, the reaction mixture was concentrated under reduced pressure and the residue was purified by chromatography (SiO₂ column 15 g, CH₂Cl₂:MeOH 94:6) to give the title compound (285 mg, 0.66 mmol, 78% isolated yield) as a colorless oil (assay=95%, estimated by ¹H NMR). The compound was obtained as a mixture of diastereomers in a ratio 3:1.

¹H NMR (250 MHz, D₂O): δ 7.39 (br s, 5H, Ph), 4.73 (br s, 2H, OC$\underline{H}_2$Ph), 4.27-4.10 (m, 5H, 2×OC$\underline{H}_2$CH₃+H), 3.95-3.86 (m, 2H), 3.59-3.54 (m, 1H), 3.24 (br dd, 1H, J=2.5, 13.5 Hz), 2.81 (br dd, 1H, J=9.0, 13.5 Hz), 1.98-1.68 (m, 2H, C$\underline{H}_2$), 1.29 (t, 6H, J=7.0 Hz, 2×OCH₂C$\underline{H}_3$)

³¹P NMR (101 MHz, D₂O): δ 27.3 (major diastereomer), 26.2 (minor diastereomer)

LC-MS APCI⁺: C₂₂H₃₁NO₈P [M+H]⁺ calculated 408.2. found 408.0.

Step 7: [6-(Benzyloxy-formyl-amino)-(3R,4R,5S)-1,3,4,5-tetrahydroxy-hexyl]-phosphonic acid diethyl ester (4f)

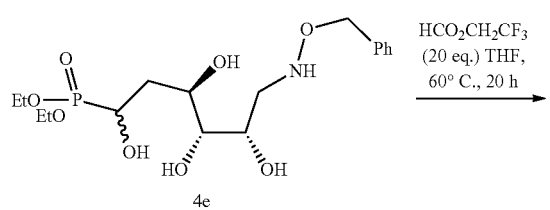

To a stirred solution of hydroxylamine 4e (272 mg, 0.63 mmol) in THF (1.5 mL) at 23° C. under nitrogen atmosphere was added trifluoroethyl formate (1.3 mL, 12.7 mmol). The solution was heated at 60° C. and stirred for 16 hours until TLC (CH₂Cl₂:MeOH 90:10) and LC-MS(APCI⁺) indicated complete conversion. After cooling at 23° C., the reaction mixture was concentrated under reduced pressure and the residue was purified by chromatography (SiO₂ column 15 g, CH₂Cl₂:MeOH 94:6) to give the title compound (187 mg, 0.41 mmol, 65% isolated yield) as a white solid (assay=95%, estimated by ¹H NMR). The compound was obtained as a mixture of diastereomers in a ratio 3:1.

¹H NMR (250 MHz, D₂O): δ 8.11 (s, 0.25H, NC(=O)H, minor rotamer), 7.89 (s, 0.7H, NC(=O)H, major rotamer), 7.51-7.40 (m, 5H, Ph), 4.96 (br s, 2H, OC$\underline{H}_2$Ph), 4.26-4.11 (m, 5H, 2×OC$\underline{H}_2$CH₃+H), 4.0-3.86 (m, 2H), 3.75-3.47 (m, 3H), 2.17-2.03 (m, 0.3H), 1.96-1.69 (m, 1.7H), 1.30 (t, 6H, J=7.0 Hz, 2×OCH₂C$\underline{H}_3$)

³¹P NMR (101 MHz, D₂O): δ 27.2 (major diastereomer), 26.1 (minor diastereomer)

LC-MS APCI⁺: C₂₈H₃₁NO₉P [M+H]⁺ calculated 436.2. found 435.7.

Step 8: [6-(Formyl-hydroxy-amino)-(3R,4R,5S)-1,3,4,5-tetrahydroxy-hexyl]-phosphonic acid diethyl ester (4g)

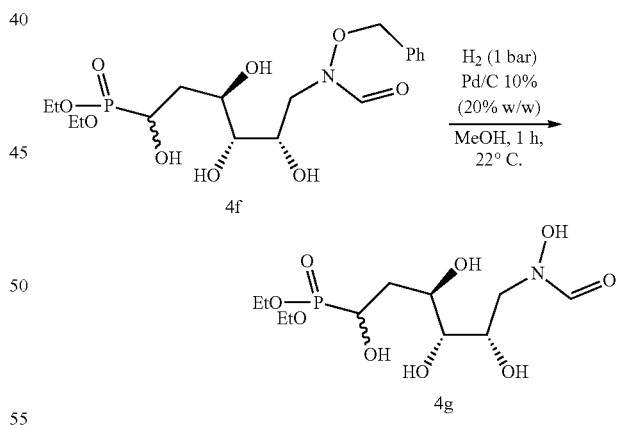

In an autoclave, compound 4f (185 mg, 0.40 mmol) was dissolved in MeOH (4.5 mL). Pd/C 10% Degussa type E101 (37 mg, 20% w/w) was added. The autoclave was purged three times with nitrogen (2 bar) and then three times with H₂ (2 bar). The pressure was set to 1 bar of H₂ and the reaction mixture was stirred at 22° C. for 1 hour. The autoclave was depressurized and purged with nitrogen. The reaction mixture was filtered over Celite® pad and the residue concentrated under reduced pressure to give the title compound (142 mg, 0.39 mmol, 97% isolated yield) as a white solid (assay=95%, estimated by ¹H NMR) which was used without further purification. The compound was obtained as a mixture of diastereomers in a ratio 3:1.

$^1$H NMR (250 MHz, D$_2$O): δ 8.33 (s, 0.14H, NC(=O)H, minor rotamer), 7.88 (s, 0.8H, NC(=O)H, major rotamer), 4.25-4.11 (m, 5H, 2×OCH$_2$CH$_2$+H), 4.02-3.92 (m, 2H), 3.76-3.57 (m, 3H), 2.22-2.07 (m, 0.3H), 1.99-1.70 (m, 1.7H), 1.30 (t, 6H, J=7.0 Hz, 2×OCH$_2$CH$_2$)

$^{31}$P NMR (101 MHz, D$_2$O): δ 27.3 (major diastereomer), 26.2 (minor diastereomer)

LC-MS APCI$^+$: C$_{22}$H$_{25}$NO$_9$P [M+H]$^+$ calculated 346.1. found 345.9.

Step 9: [6-(Formyl-hydroxy-amino)-(3R,4R,5S)-1,3,4,5-tetrahydroxy-hexyl]-phosphonic acid, monosodium salt (Example 4)

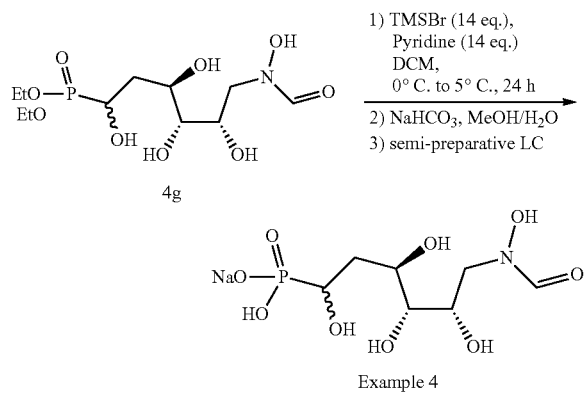

Example 4

To a stirred suspension of 4 g (80 mg, 0.22 mmol) in anhydrous CH$_2$Cl$_2$ (4 mL) at 0° C. under nitrogen atmosphere was added Pyridine (143 μL, 1.76 mmol). TMSBr (240 μL, 1.76 mmol) was added dropwise over 5 min and the reaction mixture was stirred at 0° C. for 2 hours and then 15 hours at 5° C. At this time, starting material was still detected LC-MS (ESI$^-$). At 5° C., Pyridine (107 μL, 1.32 mmol) and then TMSBr (180 μL, 1.32 mmol) were added. The reaction mixture was stirred at 5° C. during 7 hours until LC-MS indicated complete conversion. The reaction mixture was concentrated under reduced pressure at 0° C. Water (2 mL) and MeOH (2 mL) were added to the residue at 0° C. and the mixture was neutralized with an aqueous solution of NaHCO$_2$ up to pH=7.5. The solution was stirred at 20° C. until complete desilylation as determined by LC-MS (ESI$^-$). The reaction mixture was then lyophilized and the resulting powder was purified by semi-preparative liquid chromatography (Column: Modulocart QS Strategy 10RP 21.2×250 mm, InterChim, gradient H$_2$O:CH$_3$CN 3:97 to 40:60 over 15 min, flow rate 12 mL/min, fraction size 5 mL, Detector: MS-ESI$^-$) to give the title compound (33 mg, 0.1 mmol, 45% isolated yield) as a yellow solid (assay=95%, estimated by $^1$H NMR; Area %=96%, TIC Mode in LC-MS). The compound was obtained as a mixture of diastereomers in a ratio 3:1.

$^1$H NMR (250 MHz, D$_2$O): δ 8.26 (s, 0.12H, NC(=O)H, minor rotamer), 7.80 (s, 0.8H, NC(=O)H, major rotamer), 4.09-3.86 (m, 2H), 3.77-3.54 (m, 4H), 2.17-2.02 (m, 0.3H), 1.92-1.68 (m, 1.7H)

$^{31}$P NMR (101 MHz, D$_2$O): δ 17.8 (major diastereomer), 16.9 (minor diastereomer)

LC-MS ESI$^-$: C$_7$H$_{15}$NO$_9$P [M−H]$^-$ calculated 288.1. found 288.1.

Example 5: [(2S,3S,4S)-5-(Formyl-hydroxy-amino)-2,3,4-trihydroxy-pentyl]-phosphonic acid sodium salt (Sodium 1-(N-benzyloxy-N-formylamino)-1,5-dideoxy-D-ribitol] 5-phosphonate)

Step 1: 2,3,4-Tri-O-benzyl-1-(N-benzyloxy-N-formylamino)-1,5-dideoxy-5-iodo-D-ribitol

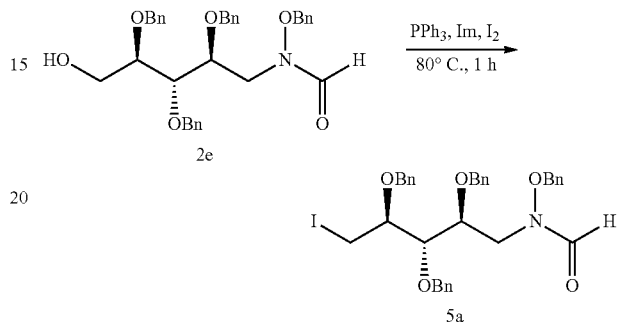

A solution of imidazole (44 mg, 0.65 mmol), triphenylphosphine (142 mg, 0.54 mmol), I2 (137 mg, 0.54 mmol) and compound 2e (250 mg, 0.45 mmol, obtained as in Example 2, step 5) in anhydrous toluene (5 mL) was stirred under argon atmosphere at 80° C. for 1 h when TLC indicated complete consumption of the starting material. The dark yellow reaction mixture was cooled to RT and concentrated. The residue was taken up in DCM (10 mL), filtered through cotton, washed with Na$_2$S$_2$O$_2$ (5%, 2×5 ml) and NaHCO$_2$ (5 mL). The aqueous phases were reextracted with DCM (10 mL) and the combined organic phases were dried (MgSO$_4$) and filtered. Silica gel (3 g) was added to the filtrate and the solvent was removed. The remaining silica gel was directly applied onto a prepacked silica gel column. Elution with hexane/EtOAc 2:1 afforded the target compound 5a (240 mg, 66%) as colorless oil; R$_f$ 0.6 (Hex:EtOAc 2:1); [α]$_D^{20}$ −12 (0.5, CHCl$_3$). $^1$H NMR (600 MHz, toluene d8, 85° C.) δ: 8.03 (s, 1H, CH$_2$NC(O) H), 7.28-6.92 (m, 20H, 4×OCH$_2$Ph), 4.67-4.27 (m, 8H, 4×OCH$_2$Ph), 4.09 (m, 1H, H-2), 3.76 (m, 1H, H-3), 3.72-3.55 (2×bs, 2H, CH$_2$N(O)H), 3.37 (dd, 1H, J$_{5a,5b}$ 10.7, J$_{5a,4}$ 4.0, H-5a), 3.28 (m, 1H, H-4), 3.21 (dd, 1H, J$_{5b,5a}$ 10.6, J$_{5b,4}$ 3.7, H-5b). $^{13}$C NMR (150 MHz, toluene-d$_8$, 85° C.) δ 138.95, 138.87, 138.50 (Cq, 3×OCH$_2$Ph), 136.01 (Cq, NOCH$_2$Ph), 129.57-128.00 (CH 4×OCH$_2$Ph), 81.78 (C-3), 78.06 (C-4), 77.52 (OCH$_2$Ph), 77.12 (C-2), 74.52, 73.36, 72.72 (3×OCH$_2$Ph), 8.25 (C-5). HR ESI$^+$ MS: C$_{34}$H$_{36}$INO$_5$ [M+H]$^+$ calcd. 666.1711. found 666.1716.

Step 2: Diethyl [2,3,4-tri-O-benzyl-1-(N-benzyloxy-N-formylamino)-1,5-dideoxy-D-ribitol] 5-phosphonate (5b)

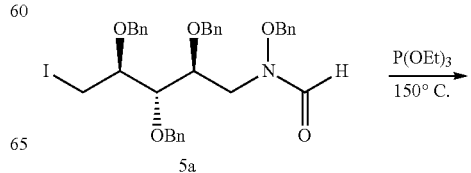

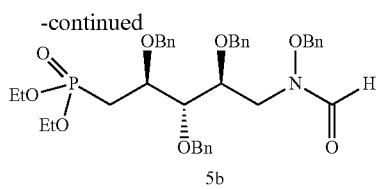

5b

A solution of compound 5a (222 mg, 0.33 mol) and P(OEt)$_3$ (300 µL) was heated to 150° C. for 3 h. The reaction mixture was cooled to RT, the residual P(OEt)$_3$ was removed in vacuo. The residual oil was flashed over a short plug of silica gel (2 g, Hex/EtOAc 2:1). The product containing fractions were pooled, concentrated, and purified by HPLC column chromatography (YMC Si 10×250, Hex/EtOAc 2:1, fraction size mL, flow rate 5 mL) to give the target compound 5b as colorless oil (100 mg, 44%); R$_f$ 0.26 (Hex/EtOAc 2:1); [α]$_D^{20}$+0.5 (0.9, CHCl$_3$); $^1$H NMR (DMSO, 600 MHz, 90° C.) δ 8.14 (bs, 1H, C(=O)H), 7.0-7.24 (m, 20H, 4×OCH$_2$Ph), 4.92-4.89 (m, 2H, NOCH$_2$Ph), 4.74-4.56 (m, 6H, 2×OCH$_2$Ph), 4.14-4.08 (m, 1H, H-4), 4.03-3.95 (m, 6H, H-2, H-3, 2×OCH$_2$CH$_3$), 3.88-3.80 (m, 2H, H-1a, H-1b), 2.23 (ddd, 1H, J$_{5a,5b}$ 15.8, J$_{5a,4}$ 4.4, J$_{5a,P}$ 18.4 Hz, H-5a), 2.15 (ddd, 1H, J$_{5b,5a}$ 15.8, J$_{5b,4}$ 7.4, J$_{5b,P}$ 17.6 Hz, H-5b), 1.24-1.20 (m, 6H, 2×OCH$_2$CH$_3$). $^{31}$P NMR (DMSO, 242 MHz, 90° C.) δ 28.78 (P(O)(OCH$_2$CH$_3$)$_2$). $^{13}$C NMR (DMSO, 150 MHz, 90° C.): δ 137.64, 137.52, 137.37 (Cq, 3×C—Ar), 134.38 (Cq, NOCH$_2$Bn), 128.92, 128.88, 128.26, 127.67, 127.51, 127.39, 127.31, 127.26, 126.85, 126.83, 126.79, 126.64, 126.61, 126.54 (C—Ar), 79.88 (d, J$_{C4,P}$ 10.3 Hz, C-3), 75.37 (OCH$_2$Ph), 74.72 (C-2), 74.15 (C-4), 71.94, 71.10, 71.05 (OCH$_2$Ph), 60.25 (d, J$_{P,OCH2CH3}$ 6 Hz, POCH$_2$CH$_3$), 60.15 (d, J$_{P,OCH2CH3}$ 6 Hz, POCH$_2$CH$_3$), 46.82* (*det by HSQC, NCH$_2$), 27.02 (d, J$_{P,C-5}$ 139 Hz, C-5), 15.31, 15.27, 15.24 (2×OCH$_2$CH$_3$); HR ESI-MS: C$_{38}$H$_{46}$NO$_8$P [M+Na]$^+$ calcd. 698.2853. found 698.2582.

Step 3: Sodium 1-(N-benzyloxy-N-formylamino)-1, 5-dideoxy-D-ribitol] 5-phosphonate (Example 5)

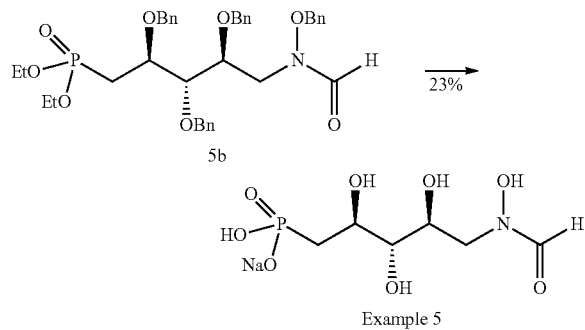

Example 5

5b (44.5 mg, 64 µmol) was dissolved in anhydrous DCM, pyridine (21 µL, 0.26 mmol) and TMSBr (34 µl, 0.26 mmol) were added under argon atmosphere, and the reaction was stirred at room temperature 29 h. The reaction was monitored by HPLC MS (C-4, gradient MeCN/H$_2$O 5 to 100% MeCN), which showed complete conversion to the product. The reaction mixture was concentrated to dryness, taken up in DCM (10 mL) and washed with citric acid (0.25 M). The aqueous phase was reextracted with DCM. The organic phase was dried (MgSO$_4$) and concentrated to give a white solid (36 mg) that was taken up in THF/H$_2$O 5:1 containing 1% AcOH (2 mL). Pd(OH)$_2$—C(6.2 mg) was added and the reaction mixture was stirred under hydrogen atmosphere (1 bar) at room temperature for 7 h when fresh catalyst (6.2 mg) was added and stirring was continued for further 15 h for completion (R$_f$ of product 13.5 minutes). The reaction was monitored by HPLC-MS (Sequant ZIC HILIC 4.6×150 mm, Gradient MeCN/H$_2$O 85 to 40% MeCN). The reaction mixture was filtered through a syringe filter and the filter was successively washed with MeOH/H$_2$O 1:1 (15 mL). The filtrate was concentrated, and the residue was taken up in H$_2$O and neutralized with NaHCO$_3$ (10 mg, 0.12 mmol) and concentrated. The residue was flashed (MeCN/H$_2$O 1:1) through a short plug of ZIC-HILIC silica gel (500 mg). Product containing fractions were concentrated, taken up in MeCN/H$_2$O 3:1 (200 µL) and purified by repeated ZIC-HILIC chromatography (Column: Sequant ZIC HILIC 10×250 mm, Merck, gradient MeCN/H$_2$O 85 to 40%, flow rate 3 ml, fraction size 2 mL). Staining fractions were evaporated and pooled according to $^1$H NMR analysis to give the target compound 33 (B-5) (4 mg, 23%) as white solid. [α]$_D^{20}$ −6.7 (0.4, H$_2$O); $^1$H NMR (600 MHz, D$_2$O): δ 8.33 (s, 0.2H, NC(=O)H, minor rotamer), 7.89 (s, 0.8H, NC(=O)H, major rotamer), 4.07-4.02 (m, 1H, H-4), 4.02-3.98 (dt, 1H, H-3), 3.75 (dd, 1H, J$_{1b,1b}$ 14.9, J$_{1a,2}$ 2.2 Hz, H-1a), 3.67-3.61 (m, 2H, H-2, H-1b), 1.83 (ddd, 1H, J$_{5a,5b}$ 14.9, J$_{5a,4}$ 3.7, J$_{5a,P}$ 17.8 Hz, H-5a), 1.61 (ddd, 1H, J$_{5b,5a}$ 15.0, J$_{5b,4}$ 9.4, J$_{5b,P}$ 15.1 Hz, H-5b). $^{31}$P NMR (D$_2$O, 242 MHz) δ 20.54 (P(O)(OH)$_2$). $^{13}$C NMR (D$_2$O, 150 MHz): δ 161.08 (CHO), 76.72 (d, J 11.9 Hz, C-3), 69.19 (d, J 3.3 Hz, C-4), 68.44 (C-2, minor rotamer), 67.76 (C-2, major rotamer), 54.12 (C-1, major rotamer), 50.07 (C-1, minor rotamer), 31.53 (d, J 128.39, C-5); HR ESI-MS: C$_6$H$_{14}$NO$_8$P [M–H]$^-$ calcd. 258.0384. found 258.0383.

Example 6: Sodium 1-(N-benzyloxy-N-formylamino)-1-deoxy-5,6-dihydroxy-D-ribo-hexitol)] 6-phosphonate Step 1: Dibenzyl [2,3,4-tri-O-benzyl-1-(N-benzyloxy-N-formylamino)-1-deoxy-5,6-dihydroxy-D-ribo-hexitol)] 6-phosphonate (6a)

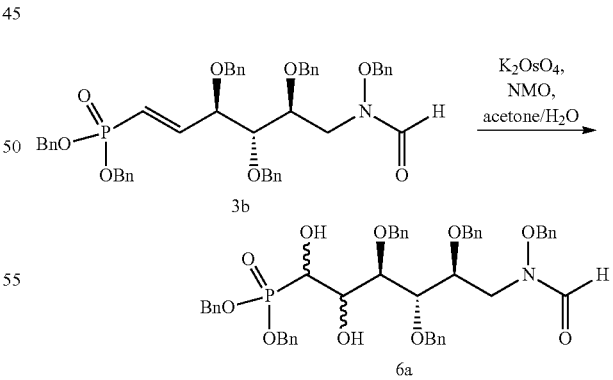

Hexenitol 3b (50 mg, 0.06 mmol, obtained as described in Example 3, Step 2) was dissolved in 2:1 acetone/water (0.75 mL) and NMO (10 mg, 0.1 mmol) was added. Then potassium osmate (2.25 mg, 6.2 µmol) was added and the reaction was stirred overnight at laboratory temperature. Since TLC (EtOAc/Hex 1:2) showed only minor conversion, another 0.1 eq. of potassium osmate and 1.6 eq. of NMO were added.

This was repeated 3 times until an acceptable conversion was reached (after 5 days). The reaction was quenched by adding satd. aq. Na$_2$SO$_3$ and extraction into EtOAc. The organic phase was washed with aq. 4% HCl, satd. aq. NaHCO$_3$, and brine. The organic layer was dried (MgSO$_4$) and concentrated and the product was isolated by column chromatography (EtOAc/Hex: 1:2) to give 6a as syrup. Yield: 41 mg (79%). [α]$_D^{20}$+11.9 (c 0.56, CHCl$_3$); $^1$H NMR (600 MHz, toluene-d$_8$ 80° C.): δ 8.09 (s, 1H, H-formyl), 7.30-6.96 (m, 30H, H—Ar), 5.02 (d, 2H, CH$_2$—Ar), 4.87 (d, 2H, CH$_2$—Ar) 4.70-4.62 (m, 6H, 3×CH$_2$—Ar), 4.54 (s, 2H, CH$_2$—Ar), 4.44 (t, 1H, J=6.9 Hz, H-5), 4.41 (d, 1H, J=9.7 Hz, H-6), 4.19 (dd, 1H, J=4.2 Hz, J=2.5 Hz, H-3), 4.08 (m, 2H, H-3, H-2), 3.80 (bs, 2H, H-1a, H-1b); $^{13}$C NMR (150 MHz): δ 138.5-124.5 (30×C—Ar), 80.4 (C-4), 79.4 (C-2), 76.8 (C-3), 76.4 (CH$_2$—Ar), 74.5 (CH$_2$—Ar), 73.5, 72.7 (2×CH$_2$—Ar), 70.6 (C-5), 68.8 (CH$_2$—Ar), 68.5 (C-6), 67.5 (CH$_2$—Ar), 48.9 (C-1). HR-MS: C$_2$H$_{16}$NO$_8$P [M+H]$^+$ calc: 846.3402. found: 846.3401.

Step 2: Sodium 1-(N-benzyloxy-N-formylamino)-1-deoxy-5,6-dihydroxy-D-ribo-hexitol)] 6-phosphonate (Example 6)

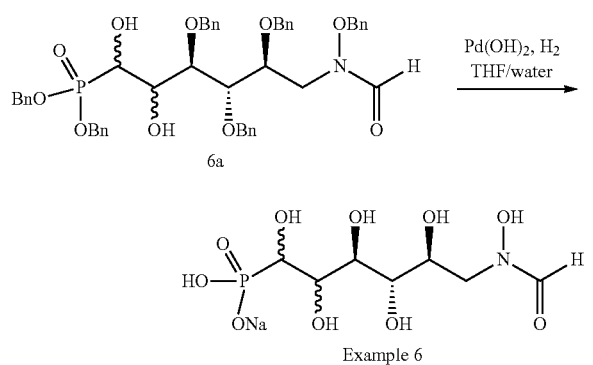

Compound 6a (24 mg, 0.03 mmol) was dissolved in 1:2 THF/water mixture and Pd(OH)$_2$ catalyst (4 mg, 20% w/w) was added. The reaction was stirred overnight under hydrogen atmosphere (1 bar) and checked by TLC (Chloroform/Metanol/Water 10:10:3). After completeness, solid sodium bicarbonate (4 mg, 0.09 mmol) was added, and all volatiles were removed. Then the crude was purified by repeated ZIC-HILIC chromatography (Column: Sequant ZIC HILIC 10×250 mm, Merck, Gradient MeCN/H$_2$O 85 to 40%, flow rate 3 mL, fraction size 2 mL). Purity of fractions was checked by $^1$H NMR and product containing fractions were pooled and lyophilized to give title compound (0.9 mg, 2.5 μmol, 9%) as white solid. [α]$_D^{20}$ −20.5 (c 0.24, water). $^1$H NMR (D$_2$O, 600 MHz, pH=7): δ 8.29 (s, 0.2H, NC(O)H, minor rotamer), 7.84 (s, 0.8H, NC(O)H, major rotamer), 4.22 (m, 1H, J=5 Hz, H-2), 4.01 (dt, 1H, H-5), 3.88 (m, 2H, H-3, H-4), 3.83 (dd, 1H, J$_{6,5}$=2.5 Hz, (J$_{6,P}$=10 Hz, H-6), 3.72 (dd, 1H, J$_{1a,2}$=2 Hz, J$_{1b,1a}$=15 Hz, H-1a), 3.65 (dd, 1H, J$_{1b,2}$=9 Hz, H-1b). $^{13}$C NMR (150 MHz): δ 159.7 (CH=O), 74.65 (C-3), 72.85 (C-5), 72.1 (C-4), 69.3 (C-6), 68.4 (C-2) and 54.4 (C-1). LC-MS (HILIC) calculated for C$_7$H$_{16}$NO$_{10}$P (305.0512). found: 305.9 (M+H)+, 303.8 (M−H)$^−$.

Example 7: [(3R,4R,5S)-6-(Formyl-hydroxy-amino)-3,4,5,7-tetrahydroxy-heptyl]-phosphonic acid (Diastereoisomer 1)

Step 1: Triisopropyl-((2R,3S,4S)-2,3,4-tris-benzyloxy-hex-5-enyloxy)-silane (7a)

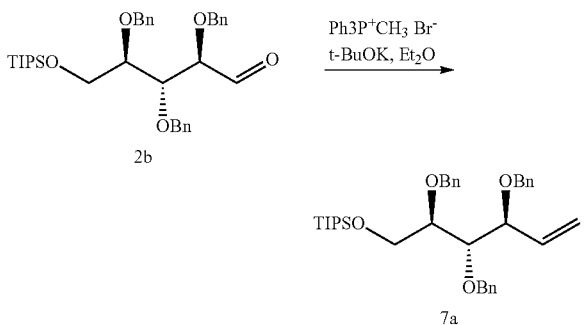

Under argon a solution of methyltriphenylphosphonium bromide (37.3 g, 104 mmol, 2.64 eq.) and t-BuOK (12.7 g, 113 mmol, 2.86 eq.) in diethyl ether (400 mL) was refluxed for 1 hour. Then after cooling to RT a solution of the compound 2b (22.8 g, 39.6 mmol, 1 eq., obtained as described in Example 2, step 2) in ether (200 mL) was added. The reaction mixture was stirred at RT for 20 h then NH$_4$Cl saturated aqueous solution was added. The mixture was extracted with AcOEt, combined organic phases were washed with brine, dried over Na$_2$SO$_4$ and concentrated under reduced pressure. Obtained oily residue was purified by chromatography on silica gel (eluent cyclohexane/ethyl acetate 98/2) to give compound 7a (20.5 g; 90%) as yellow oil.

$^1$H NMR (400 MHz, CDCl$_3$): δ 7.36-7.28 (m, 15H, 3×Ph), 5.95 (m, 1H, H-2), 5.35 (d, 1H, J$_{1a,2}$=8 Hz, H-1a), 5.21 (d, 1H, J$_{1b,2}$=18 Hz, H-1b), 4.88-4.39 (m, 6H, 3×OCH$_2$Ph), 4.21-4.19 (m, 1H, H-3), 4.07 (m, 1H, H-6a), 3.91-3.83 (m, 2H, H-6b, H-4), 3.66-3.63 (m, 1H, H-5), 1.09-1.06 [m, 21H, Si(CHMe$_2$)$_3$].

Step 2: (3S,4R,5R)-3,4,5-Tris-benzyloxy-6-triisopropylsilanyloxy-hexane-1,2-diol (7b)

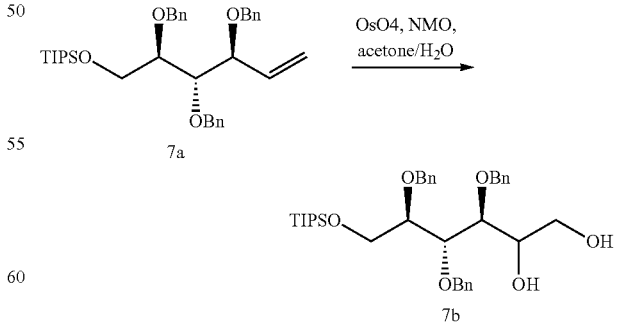

To a solution of compound 7a (20.1 g, 35.0 mmol, 1 eq.) in the mixture of acetone/H$_2$O/tert-Butyl alcohol (470 mL/280 mL/95 mL) at 0° C. were added N-methyl-morpholine oxide (8.2 g, 70 mmol, 2 eq.) and osmium tetraoxide (4% in water, 1 mL, cat.). Reaction mixture was stirred at 0° C. for 1 h, then at RT for 7-10 days. After addition of the brine reaction mixture was extracted with AcOEt, combined organic phases were washed with brine, dried over $Na_2SO_4$ and concentrated under reduced pressure. Obtained oily residue was purified by chromatography on silica gel (eluent cyclohexane/EtOAc 1/0 to 7/3) to afford compound 7b (20.2 g, 94%) as brown oil.

$^1$H NMR (400 MHz, $CDCl_3$): δ 7.35-7.28 (m, 15H, 3×Ph), 4.83-4.58 (m, 6H, 3×$OCH_2$Ph), 4.02-3.69 (m, 8H, H-1 to H-6), 3.52 (d, 1H, $J_{2,OH}$=4 Hz, OH), 2.21 (t, 1H, $J_{1,OH}$=4 Hz, OH), 1.09-1.06 [m, 21H, Si$(CHMe_2)_3$].

Step 3: (3S,4R,5R)-3,4,5-Trisbenzyloxy-6-triisopropylsilanyloxy-1-trityloxyhexan-2-ol (7c)

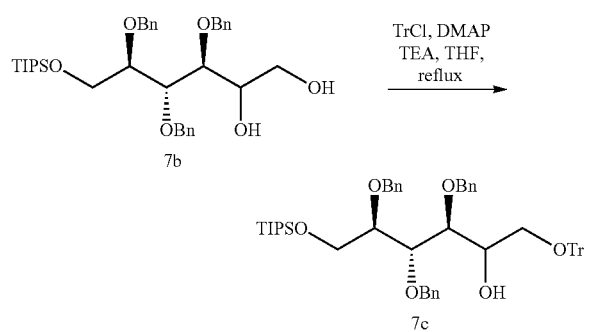

To a solution of compound 7b (20.2 g, 33.2 mmol, 1 eq.) in THF (290 mL) under argon were added trityle chloride (13.1 g, 82.9 mmol, 2.5 eq.), DMAP (1.62 g, 13.2 mmol, 0.4 eq.) and triethylamine (47 g, 332 mmol, 10 eq.) and the mixture was stirred at reflux for 20 h. After addition of the brine reaction mixture was extracted with AcOEt, combined organic phases were washed with brine, dried over $Na_2SO_4$ and concentrated under reduced pressure. Obtained oily residue was purified by chromatography on silica gel (eluent cyclohexane/EtOAc 95/5) to afford compound 7c (21.1 g, 75%) as yellow oil.

$^1$H NMR (400 MHz, $CDCl_3$): δ 7.45-7.09 (m, 30H, 6×Ph), 4.83-4.55 (m, 6H, 3×$OCH_2$Ph), 4.12-3.85 (m, 6H, H-2 to H-6), 3.39-3.26 (m, 2H, H-1), 3.15 (d, 1H, $J_{2,OH}$=4 Hz, OH), 1.09-1.05 [m, 21H, Si$(CHMe_2)_3$].

Step 4: (3R,4R,5R)-3,4,5-Tris-benzyloxy-6-triisopropylsilanyloxy-1-trityloxy-hexan-2-one (7d)

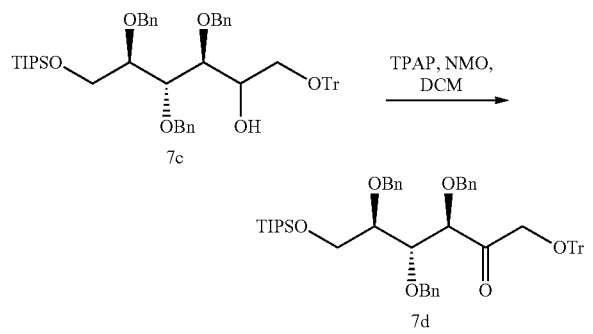

To a solution of compound 7c (15.3 g, 18.7 mmol, 1 eq.) in dichloromethane (200 mL) were added N-methyl-morpholine oxide (4.38 g, 37.4 mmol, 2 eq.) and tetrapropylammonium perruthenate (659 mg, 1.87 mmol, 0.1 eq.) and the mixture was stirred at RT for 20 h, filtered through celite pad and concentrated under reduced pressure. Obtained oily residue was purified by chromatography on silica gel (eluent cyclohexane/EtOAc 98/2) to afford compound 7d (14.1 g, 88%) as yellow oil.

$^1$H NMR (400 MHz, $CDCl_3$): δ 7.42-7.13 (m, 30H, 6×Ph), 4.68-4.43 (m, 6H, 3×$OCH_2$Ph), 4.31 (d, 1H, $J_{2,3}$=5 Hz, H-3), 4.07-3.94 (m, 4H, H-4 to H-6), 3.78-3.71 (m, 2H, H-1), 1.09-1.03 [m, 21H, Si$(CHMe_2)_3$].

Step 5: O-Benzyl-N-((2S,3S,4R)-2,3,4-tris-benzyloxy-5-triisopropylsilanyloxy-1-trityloxymethylpentyl)-hydroxylamine (7e)

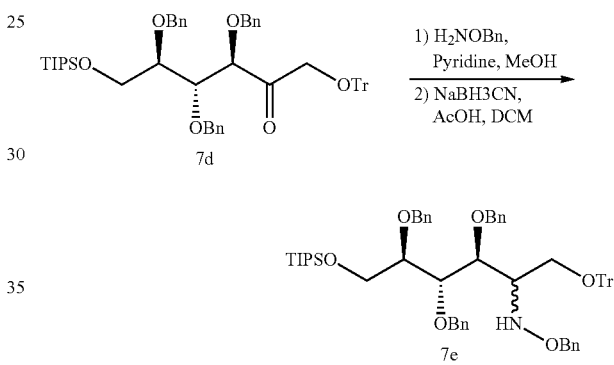

To a solution of compound 7d (39.0 g, 45.9 mmol, 1 eq.), methanol (530 mL) under argon were added O-benzylhydroxylamine hydrochloride (14.7 g, 91.9 mmol, 2 eq.) and pyridine (14.8 mL, 184 mmol, 4 eq.) and the mixture was stirred at reflux for 20 h, then concentrated under reduced pressure. The residue was diluted with the mixture water/EtOAc, extracted with AcOEt, combined organic phases were washed with brine, dried over $Na_2SO_4$ and concentrated under reduced pressure. Obtained oily residue was purified by chromatography on silica gel (eluent cyclohexane/EtOAc 98/2) to afford intermediate oxime (35.5 g, 81%). To a solution of the oxime (4.8 g, 5.03 mmol, 1 eq.) in DCM (160 mL) under argon sodium cyanoborohydride (6.3 g, 100.6 mmol, 20 eq.) and acetic acid (17.4 mL, 301 mmol, 60 eq.) were added. Reaction mixture was stirred at 0° C. for 1 h30, then basified by addition of $NaHCO_3$ saturated aqueous solution. Phases where separated and aqueous phase was extracted with DCM. Combined organic phases were washed with brine, dried over $Na_2SO_4$ and concentrated under reduced pressure to afford crude compound 7e, used without purification in the next step.

$^1$H NMR (400 MHz, $CDCl_3$): δ 7.44-7.14 (m, 35H, 7×Ph), 5.15-5.14 (m, 2H, $OCH_2$Ph), 4.71-3.82 (m, 13H, 3×$OCH_2$Ph et H-1 á H-6), 1.06-1.01 [m, 21H, Si$(CHMe_2)_3$].

Step 6: N-Benzyloxy-N-((2S,3S,4R)-2,3,4-tris-benzyloxy-5-triisopropylsilanyloxy-1-trityloxymethyl-pentyl)-formamide (7f)

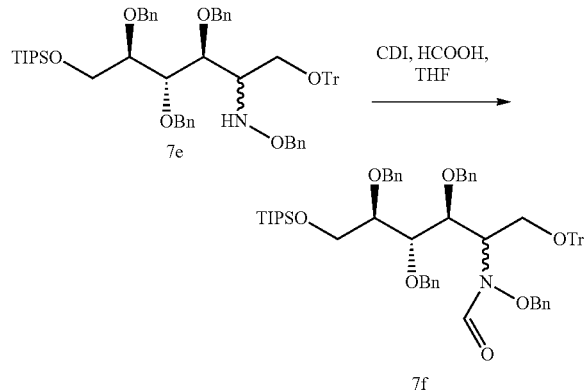

To a solution of formic acid (1.90 mL, 50.3 mmol, 1 eq.) in THF (80 mL) under argon at 0° C. was added carbonyldiimidazole (8.16 g, 50.3 mmol, 10 eq.) by portions. The mixture was stirred at 0° C. for 1 h, then a solution of compound 7e (5.03 mmol, 1 eq.) in THF (80 mL) was added dropwise. The mixture was stirred for 20 h at RT (TLC control showed not total conversion), then another portion of the solution of CDI/formic acid (10 eq.) was added and the mixture was stirred for another 20 h at RT. The reaction mixture was concentrated under reduced pressure, obtained oily residue was purified by chromatography on silica gel (eluent cyclohexane/EtOAc 95/5) to afford compound 7f (3.36 g, 68%) as yellow oil.

$^1$H NMR (400 MHz, CDCl$_3$): δ 8.54, 8.48, 7.90, 7.81 (s, 1H, NCHO, rotamers+diastereoisomers), 7.36-6.93 (m, 35H, 7×Ph), 5.22, 5.07 (2 d, 1H, J=8 Hz), 4.78-3.20 (m, 15H, 4×OCH$_2$Ph and 7H), 1.06-1.02 [m, 21H, Si(CHMe$_2$)$_3$].

Step 7: N-Benzyloxy-N-((2S,3S,4R)-2,3,4-tris-benzyloxy-5-hydroxy-1-trityloxymethyl-pentyl)-formamide (7h, Diastereoisomers 1 and 2)

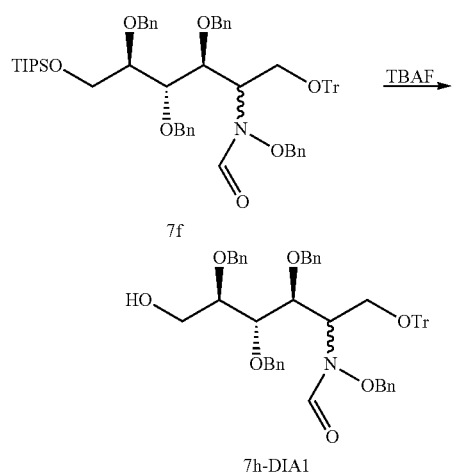

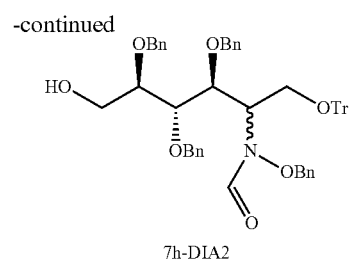

To a solution of the compound 7f (3.36 g, 3.41 mmol, 1 eq.) in THF (120 mL) at 0° C. was added TBAF.3H$_2$O (2.15 g, 6.82 mmol, 2 eq.) and the mixture was stirred at 0° C. for 2 h, then concentrated under reduced pressure. Obtained oily residue was purified by chromatography on silica gel (eluent cyclohexane/EtOAc 80/20) to afford compounds 7h-DIA1 (1.40 g, 49%) and 7h-DIA2 (1.07 g, 38%) as white foams. Two separated diastereoisomers of the molecule possess different stereoconfiguration at position 1 chiral center of the molecule, but no additional analytical studies were performed to attribute the stereochemistry of each diastereoisomer. Stereoconfiguration of each diastereoisomer at position 1 of the molecule was attributed in random/aleatory manner and parallel series were coded DIA-1 and DIA-2.

7h-DIA1: $^1$H NMR (400 MHz, CDCl$_3$): δ 8.49 (s, 0.3H, NCHO, minor rotamer), 7.91 (s, 0.7H, NCHO, major rotamer), 7.40-7.02 (m, 35H, 7×Ph), 5.11 (d, 1H, J=12 Hz), 4.73-4.43 (m, 7H), 4.18-4.02 (m, 2H), 3.79-3.67 (m, 5H), 3.44-3.28 (m, 2H).

7h-DIA2: $^1$H NMR (400 MHz, CDCl$_3$): δ 8.27 (s, 0.21H, NCHO, minor rotamer), 7.73 (s, 0.79H, NCHO, major rotamer), 7.28-6.86 (m, 35H, 7×Ph), 5.15 (d, 1H, J=12 Hz), 4.52-4.01 (m, 10H), 3.74-3.55 (m, 6H), 3.10 (t, 1H, J$_{6,OH}$=4 Hz, OH), 3.44-3.28 (m, 2H).

Step 8: N-Benzyloxy-N-((2S,3S,4S)-2,3,4-tris-benzyloxy-5-oxo-1-trityloxymethyl-pentyl)-formamide (7i-DIA1)

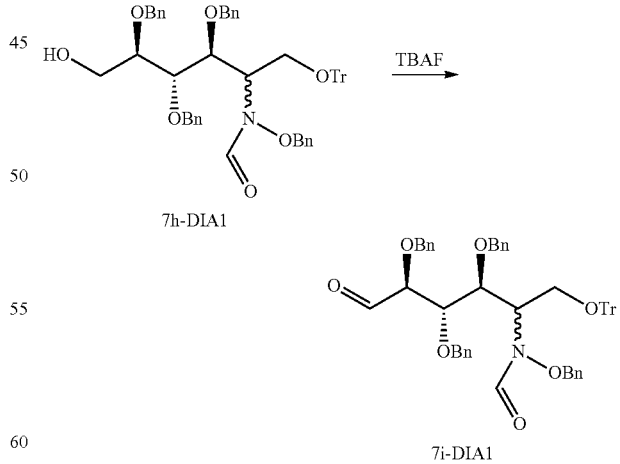

To a solution of the compound 7h-DIA1 (1.35 g, 1.63 mmol, 1 eq.) in DCM (38 mL) were added were added N-methylmorpholine oxide (381 mg, 3.26 mmol, 2 eq.) and tetrapropylammonium peruthenate (57 mg, 0.163 mmol, 0.1 eq.) and the mixture was stirred at RT for 20 h, filtered through celite pad and concentrated under reduced pressure. Obtained oily residue was purified by chromatography on silica gel (eluent cyclohexane/EtOAc 90/10) to afford compound 7i-DIA1 (1.00 g, 74%) as white foam.

$^1$H NMR (400 MHz, CDCl$_3$): δ 9.45, 9.43 (2 s, 1H, CHO, rotamers), 8.56 (s, 0.47H, NCHO, minor rotamer), 7.88 (s, 0.53H, NCHO, major rotamer), 7.41-7.20 (m, 35H, 7×Ph), 5.14-4.95 (m, 2H), 4.82-4.50 (m, 5H), 4.35-4.15 (m, 3H), 4.02-3.93 (m, 3H), 3.75-3.38 (m, 2H).

Step 9: [(E)-(3R,4R,5S)-3,4,5-Tris-benzyloxy-6-(benzyloxy-formyl-amino)-7-trityloxy-hept-1-enyl]-phosphonic acid dibenzyl ester (7j-DIA1)

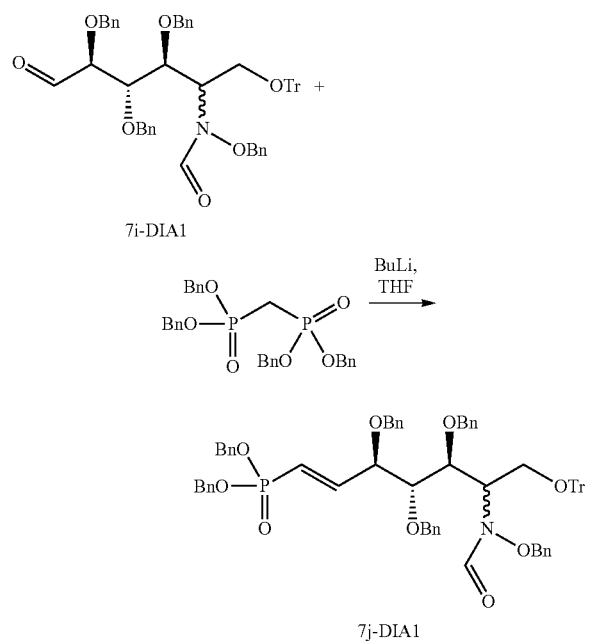

Under argon at −78° C. to a solution of bis-benzyloxy-phosphorylmethyl)-phosphonic acid dibenzyl ester (2.49 g, 4.65 mmol, 1.75 eq., obtained as described in J. Org. Chem. 2001, vol. 66, p. 3704-3708) in THF (48 mL) was added a solution of n-butyllithium (1.2M in hexane, 3.87 mL, 4.65 mmol, 1.75 eq.). The reaction mixture was stirred at −78° C. for 30 min, then a solution of the compound 7i-DIA1 (2.20 g, 2.65 mmol, 1 eq.) in THF (48 mL) was added dropwise. After stirring for 1 h at RT the reaction mixture was quenched with NH$_4$Cl saturated aqueous solution, and then extracted with EtOAc. Combined organic phases were washed with brine, dried over Na$_2$SO$_4$ and concentrated under reduced pressure. Obtained oily residue was purified by chromatography on silica gel (eluent cyclohexane/EtOAc 80/20 to 70/30) to afford compound 7j-DIA1 (2.64 g, 92%) as white foam.

$^1$H NMR (400 MHz, CDCl$_3$): δ 8.48 (s, 0.3H, NCHO, minor rotamer), 7.83 (s, 0.7H, NCHO, major rotamer), 7.33-6.74 (m, 45H, 9×Ph), 6.00-5.91 (m, 1H), 5.05-4.95 (m, 5H), 4.71-4.68 (m, 1H), 4.65-4.08 (m, 8H), 3.85-3.64 (m, 2H), 3.58-3.28 (m, 3H).

Step 10: [(E)-(3R,4R,5S,6R)-3,4,5-Tris-benzyloxy-6-(benzyloxy-formyl-amino)-7-hydroxy-hept-1-enyl]-phosphonic acid dibenzyl ester (7k-DIA1)

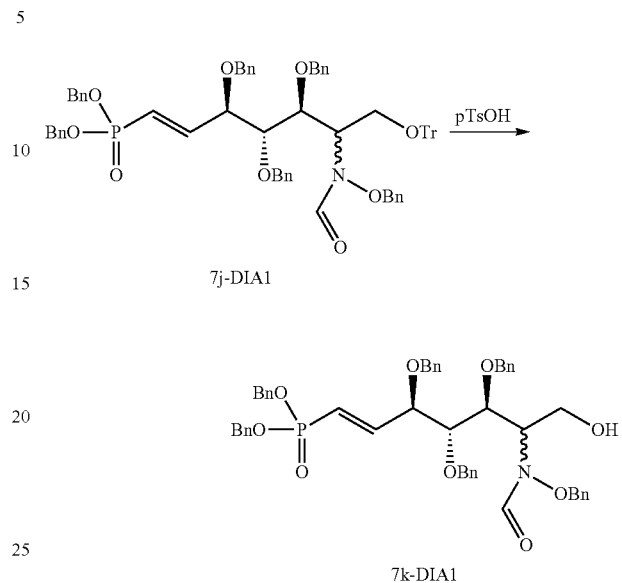

To a solution of 7j-DIA1 (2.45 g, 2.25 mmol, 1 eq.) in the mixture of EtOAc (52 mL) and tert-Butyl alcohol (11.5 mL) was added p-toluenesulfonic acid (645 mg, 3.39 mmol, 1.5 eq.). The reaction mixture was stirred at 55° C. for 3 h then quenched with NaHCO$_3$ saturated aqueous solution, and then extracted with EtOAc. Phases where separated and the aqueous phase was extracted with EtOAc. Combined organic phases were washed with brine, dried over Na$_2$SO$_4$ and concentrated under reduced pressure. Obtained oily residue was purified by chromatography on silica gel (eluent cyclohexane/EtOAc 50/50 to 20/80) to afford compound 7k-DIA1 (680 mg, 36%) as colorless oil.

$^1$H NMR (400 MHz, CDCl$_3$): δ 8.19 (s, 0.55H, NCHO, major rotamer), 7.76 (s, 0.45H, NCHO, minor rotamer), 7.32-6.87 (m, 30H, 6×Ph), 6.10-6.02 (m, 1H), 5.05-4.95 (m, 5H), 4.79-4.44 (m, 8H), 4.41-4.12 (m, 2H), 3.83-3.64 (m, 4H), 3.37-3.34 (m, 1H).

$^{31}$P NMR (161 MHz, CDCl$_3$): δ 18.65.

LCMS [[M+H]$^+$-BnOH]$^+$: 734.2.

Step 11: [(3R,4R,5S)-6-(Formyl-hydroxy-amino)-3,4,5,7-tetrahydroxy-heptyl]-phosphonic acid (7l-DIA1, Diastereoisomer 1, Example 7)

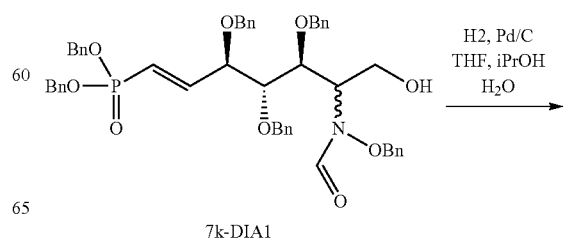

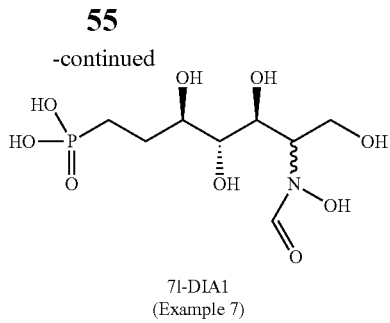

7l-DIA1
(Example 7)

To a solution of the compound 7k-DIA1 (200 mg, 0.24 mmol, 1 eq.) in the mixture of THF (15 mL) and i-PrOH (15 mL) were added water (0.22 mL) and Pd/C 10% (20 mg). The reaction mixture was stirred under hydrogen atmosphere (1 atm) for 20 h and controlled by LC-MS. Another portion of Pd/C 10% (20 mg) was added and reaction mixture was stirred under hydrogen atmosphere (1 atm) for another 20 h, then filtered through Millipore filter and concentrated under reduced pressure. The crude residue was purified via semi-preparative HPLC using HILIC-type column (XBridge PrepAmide 5 μm, OBD 19×50 mm) (sample dissolved in 4 mL of the mixture $H_2O$/acetonitrile 1/2; gradient $H_2O$/acetonitrile 15/85 to 60/40 in 12 minutes then 60/40). The fractions containing the product were lyophilized and purified again in the same chromatography conditions to afford compound 7l-DIA1 (Example 7) (15 mg, 20%) as white foam.

$^1$H NMR (400 MHz, $D_2O$): δ 8.38 (s, 0.17H, NCHO, minor rotamer), 7.89 (s, 0.83H, NCHO, major rotamer), 3.96-3.86 (m, 2H), 3.79-3.72 (m, 3H), 3.53 (dd, 1H, $J_1$=8 Hz, $J_2$=4 Hz), 1.78-1.69 (m, 2H), 1.58-1.49 (m, 2H).

$^{31}$P NMR (161 MHz, $D_2O$): δ 26.72.

MS ESI$^-$: 302.

Example 8: [(3R,4R,5S)-6-(Formyl-hydroxy-amino)-3,4,5,7-tetrahydroxy-heptyl]-phosphonic acid (8l-DIA1, Diastereoisomer 2)

Step 1: N-Benzyloxy-N-((2S,3S,4S)-2,3,4-tris-benzyloxy-5-oxo-1-trityloxymethyl-pentyl)-formamide (8i-DIA2)

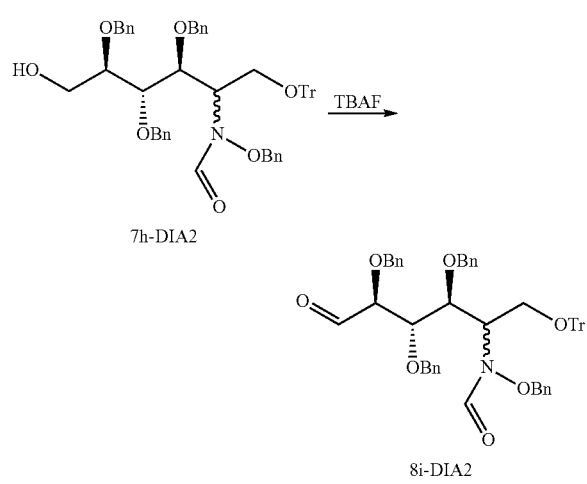

Compound 8i-DIA2 was prepared according to procedure analogous to that described in Example 7, Step 8 using solution of 7h-DIA2 (2.85 g, 3.44 mmol, 1 eq.) in DCM (80 mL), N-methyl-morpholine oxide (805 mg, 6.88 mmol; 2 eq.) and tetrapropylammonium peruthenate (121 mg; 0.344 mmol, 0.1 eq.). Purification of the crude oily product by chromatography on silica gel (eluent cyclohexane/EtOAc 80/20) afforded compound 8i-DIA2 (1.85 g, 65%) as white solid.

$^1$H NMR (400 MHz, $CDCl_3$): δ 9.39, 9.38 (2 s, 1H, CHO, rotamers), 8.42 (s, 0.2H, NCHO, minor rotamer), 7.88 (s, 0.8H, NCHO, major rotamer), 7.35-7.11 (m, 35H, 7×Ph), 5.32 (m, 1H), 4.63-4.29 (m, 8H), 3.98-3.88 (m, 4H), 3.81-3.46 (m, 2H).

Step 2: [(E)-(3R,4R,5S)-3,4,5-Tris-benzyloxy-6-(benzyloxy-formyl-amino)-7-trityloxy-hept-1-enyl]-phosphonic acid dibenzyl ester (8j-DIA2)

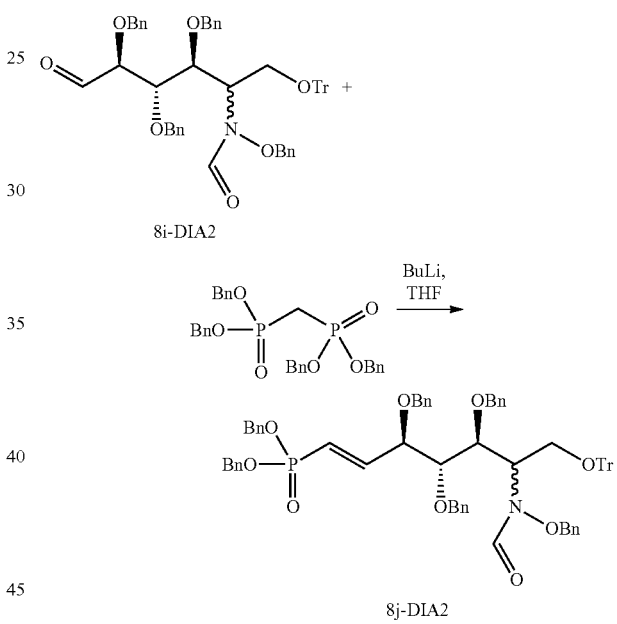

Compound 8j-DIA2 was prepared according to procedure analogous to that described in Example 7, Step 9 using a solution of bis-benzyloxy-phosphorylmethyl)-phosphonic acid dibenzyl ester (1.52 g, 2.85 mmol, 1.75 eq., obtained as described in J. Org. Chem. 2001, vol. 66, p. 3704-3708) in THF (30 mL), solution of n-butyllithium (1.2M in hexane, 2.38 mL, 2.85 mmol, 1.75 eq.) and a solution of the compound 8i-DIA2 (1.35 g, 1.63 mmol, 1 eq.) in THF (30 mL). Purification of the crude oily product by chromatography on silica gel (eluent cyclohexane/EtOAc 80/20 to 70/30) afforded compound 8j-DIA2 (1.57 g, 89%) as yellow foam.

$^1$H NMR (400 MHz, $CDCl_3$): δ 8.20 (s, 0.1H, NCHO, minor rotamer), 7.70 (s, 0.9H, NCHO, major rotamer), 7.26-6.93 (m, 45H, 9×Ph), 5.97-5.87 (m, 1H), 5.15 (d, 1H), 4.89-4.86 (m, 4H), 4.41-3.99 (m, 10H), 3.68-3.62 (m, 2H), 3.62-3.59 (m, 1H), 3.08 (t, 1H).

Step 3: [(E)-(3R,4R,5S,6R)-3,4,5-Tris-benzyloxy-6-(benzyloxy-formyl-amino)-7-hydroxy-hept-1-enyl]-phosphonic acid dibenzyl ester (8k-DIA2)

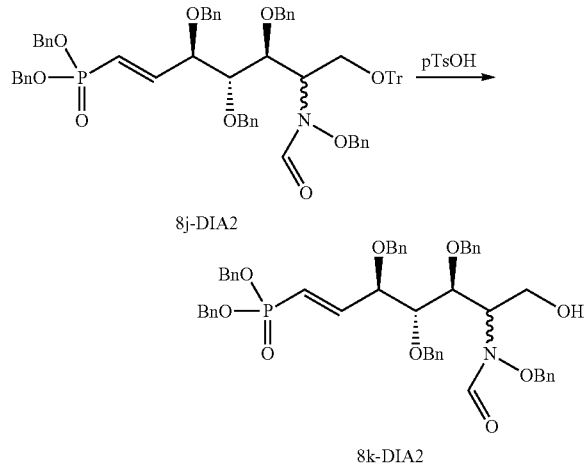

Compound 8k-DIA2 was prepared according to procedure analogous to that described in Example 7, Step 10 using a solution of 8j-DIA2 (1.57 g, 1.45 mmol, 1 eq.) in the mixture of EtOAc (33 mL) and tert-Butyl alcohol (13 mL) and p-toluenesulfonic acid (413 mg, 2.17 mmol, 1.5 eq.). Purification of the crude oily product by chromatography on silica gel (eluent cyclohexane/EtOAc 50/50 to 20/80) afforded title compound 8k-DIA2 (390 mg, 32%) as yellowish foam.

$^1$H NMR (400 MHz, CDCl$_3$): δ 8.16, 7.89, 7.81 (3 s, 1H, NCHO, 3 rotamers), 7.35-6.83 (m, 30H, 6×Ph), 6.07-5.94 (m, 1H), 5.02-4.99 (m, 5H), 4.60-4.26 (m, 10H), 3.49-3.97 (m, 5H).
$^{31}$P NMR (161 MHz, CDCl$_3$): δ 18.72.
LCMS [[M+H]$^+$-BnOH]$^+$: 734.2.

Step 4: [(3R,4R,5S)-6-(Formyl-hydroxy-amino)-3,4,5,7-tetrahydroxy-heptyl]-phosphonic acid (81-DIA2, Diastereoisomer 2, Example 8)

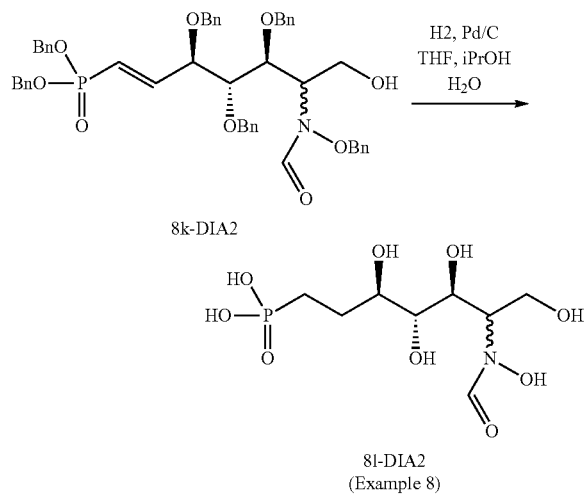

Compound 81-DIA2 was prepared according to procedure analogous to that described in Example 7, Step 11 using a solution of the compound 8k-DIA2 (200 mg, 0.24 mmol, 1 eq.) in the mixture of THF (15 mL) and i-PrOH (15 mL), water (0.22 mL) and two portions of Pd/C 10% (20 mg). Purification (twice) of the crude oily product by chromatography on silica gel by semi-preparative HPLC using HILIC-type column (XBridge PrepAmide 5 μm, OBD 19×50 mm) (sample dissolved in 4 mL of the mixture H$_2$O/acetonitrile 1/2; gradient H$_2$O/acetonitrile 15/85 to 60/40 in 12 minutes then 60/40) afforded compound 81-DIA2 (Example 8) (8 mg; 11%) as white foam.

$^1$H NMR (400 MHz, D$_2$O): δ 8.31 (s, 0.13H, NCHO, minor rotamer), 7.90 (s, 0.87H, NCHO, major rotamer), 3.96-3.81 (m, 4H), 3.67-3.62 (m, 1H), 3.57 (dd, 1H, J$_1$=8 Hz, J$_2$=8 Hz), 1.79-1.68 (m, 2H), 1.54-1.45 (m, 2H).
$^{31}$P NMR (161 MHz, D$_2$O): δ 25.95.
MS ESI$^-$: 302.

Example 9: [1-Fluoro-6-(formyl-hydroxy-amino)-(3R,4R,5S)-3,4,5-trihydroxy-hexyl]-phosphonic acid, monosodium salt

Step 1: Trifluoro-methanesulfonic acid 1-(diethoxy-phosphoryl)-(3R,4R,5R,6R)-2-(6-methoxy-2-methyl-tetrahydro-furo[3,4-d][1,3]dioxol-4-yl)-ethyl ester (9a)

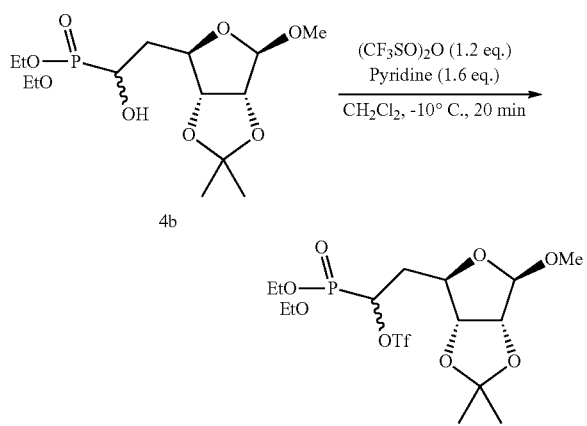

To a stirred solution of alcohol 4b (2.1 g, 5.59 mmol, obtained as described in Example 4, Step 2) in anhydrous CH$_2$Cl$_2$ (11 mL) under nitrogen atmosphere was added pyridine (0.73 mL, 8.94 mmol). The solution was cooled to −10° C. and a solution of trifluoromethanesulfonic anhydride (1.14 mL, 6.7 mmol) in CH$_2$Cl$_2$ (4 mL) was added via syringe pump over 15 min. The solution was stirred further for five minutes and H$_2$O (30 mL) was added and the layers were separated. The aqueous layer was extracted three times with CH$_2$Cl$_2$ (3×50 mL). The organic layers were combined, washed with HCl 0.5M (30 mL), dried over Na$_2$SO$_4$, filtered and concentrated under reduced pressure to give the title compound (2.86 g, 5.59 mmol, quantitative isolated yield) as a yellow oil (assay=95%, estimated by $^1$H NMR) which was used without further purification. The compound was obtained as a mixture of diastereomers in a ratio 1.5:1.

$^1$H NMR (250 MHz, CDCl$_3$): δ 5.28-5.13 (m, 1H), 5.0 (s, 0.6H, major diastereomer), 4.98 (s, 0.4H, minor diastereomer), 4.64-4.49 (m, 2.6H), 4.29-4.19 (m, 5.4H, 2×OCH$_2$CH$_3$+1H+0.4H), 3.38 (s, 1.2H, OCH$_3$, minor diastereomer), 3.36 (s, 1.8H, OCH$_3$, major diastereomer), 2.36-2.15 (m, 2H, CH—CH$_2$—), 1.47 (s, 1.8H, C—CH$_3$, major diastereomer), 1.46 (s, 1.2H, C—CH$_3$, minor diastereomer), 1.38 (t, 2.4H, J=7.0 Hz, 2×OCH$_2$CH$_3$, minor diastereomer), 1.37 (t, 3.6H, J=7.0 Hz, 2×OCH$_2$CH$_3$, major dia-stereomer), 1.31 (br s, 3H, C—CH$_3$, two diastereomers)

LC-MS APCI$^+$: C$_{15}$H$_{27}$F$_3$O$_{10}$PS [M+H]$^+$ calculated 487.1. found 486.6.

Step 2: [1-Fluoro-(3R,4R,5R,6R)-2-(6-methoxy-2,2-dimethyl-tetrahydro-furo[3,4-d][1,3]dioxol-4-yl)-ethyl]-phosphonic acid diethyl ester (9b)

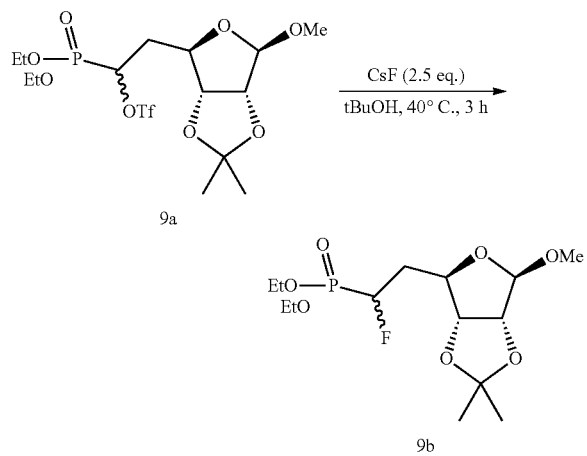

To a stirred solution of triflate 9a (2.86 g, 5.59 mmol) in tert-Butyl alcohol (10 mL) under nitrogen atmosphere was added cesium fluoride (2.15 g, 14.2 mmol). The solution was heated to 40° C. and stirred for three hours until TLC (cyclohexane:EtOAc 40:60) indicated complete conversion. Aqueous saturated NaHCO$_3$ solution (30 mL) was added and the aqueous layer was extracted three times with EtOAc (3×50 mL). The organic layers were combined, dried over Na$_2$SO$_4$, filtered and concentrated under reduced pressure. The residue was purified by chromatography (SiO$_2$ column 40 g, cyclohexane:EtOAc 50:50) to give the title compound (1.22 g, 3.25 mmol, 58% isolated yield over 2 steps) as a yellow oil (assay=95%, estimated by $^1$H NMR). The compound was obtained as a mixture of diastereomers in a ratio 1.5:1.

$^1$H NMR (250 MHz, CDCl$_3$): δ 5.10-4.74 (m, 1H), 4.98 (br s, 1H), 4.65-4.59 (m, 2H), 4.46-4.38 (m, 1H), 4.28-4.10 (m, 4H, 2×OCH$_2$CH$_3$), 3.53 (s, 1.8H, OCH$_3$, major diastereomer), 3.23 (s, 1.2H, OCH$_3$, minor diastereomer), 2.33-2.04 (m, 2H, CH—CH$_2$—), 1.48 (s, 3H, C—CH$_3$), 1.39-1.34 (m, 6H, 2×OCH$_2$CH$_3$,), 1.32 (br s, 3H, C—CH$_3$)

$^{31}$P NMR (101 MHz, CDCl$_3$): δ 17.8 (d, J$_{31P-19F}$=75 Hz, 0.4P, minor diastereomer), 17.2 (d, J$_{31P-19F}$=75 Hz, 0.6P, major diastereomer)

$^{19}$F NMR (235 MHz, CDCl$_3$): δ −208.45 (d, J$_{31P-19F}$=75 Hz, 0.6F, major diastereomer), −213.0 (d, J$_{31P-19F}$=75 Hz, 0.4F, minor diastereomer)

LC-MS APCI$^+$: C$_{14}$H$_{27}$FO$_7$P [M+H]$^+$ calculated 357.1. found 356.9.

Step 3: [1-Fluoro-(3R,4R,5R)-2-(3,4,5-trihydroxy-tetrahydro-furan-2-yl)-ethyl]-phosphonic acid diethyl ester (9c)

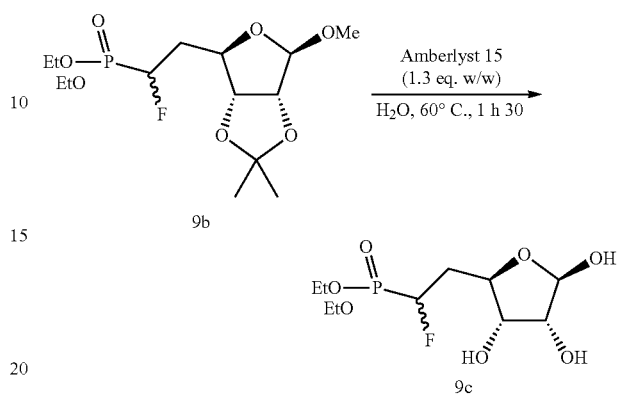

To a stirred solution of compound 9b (519 mg, 1.31 mmol) in H$_2$O (5 mL) at 22° C. was added Amberlyst 15 (675 mg, previously washed with H$_2$O, 1.3 eq. w/w). The resulting suspension was stirred at 60° C. for 1.5 hour until TLC (EtOAc:MeOH 90:10) and LC-MS (APCI$^+$) indicated complete conversion. The reaction mixture was filtered and the resin was washed with H$_2$O. pH was adjusted to pH=6.8 by adding 2.4 mL of 0.1M NaOH aq. solution. The solution was concentrated to approximately 3 mL to give the title compound (1.31 mmol theoretical) in solution in H$_2$O which was used without further purification.

$^1$H NMR (250 MHz, D$_2$O): δ 5.35-5.08 (m, 2H), 4.29-3.94 (m, 7H, 2×OCH$_2$CH$_3$+3H), 2.42-1.94 (m, 2H, CH—CH$_2$), 1.32 (t, 6H, J=7 Hz, 2×OCH$_2$CH$_3$)

LC-MS APCI$^+$: C$_{10}$H$_{21}$FO$_7$P [M+H]$^+$ calculated 303.1. found 302.9.

Step 4: (6-Benzyloxyimino-1-fluoro-(3R,4R,5R)-3,4,5-trihydroxy-hexyl)-phosphonic acid diethyl ester (9d)

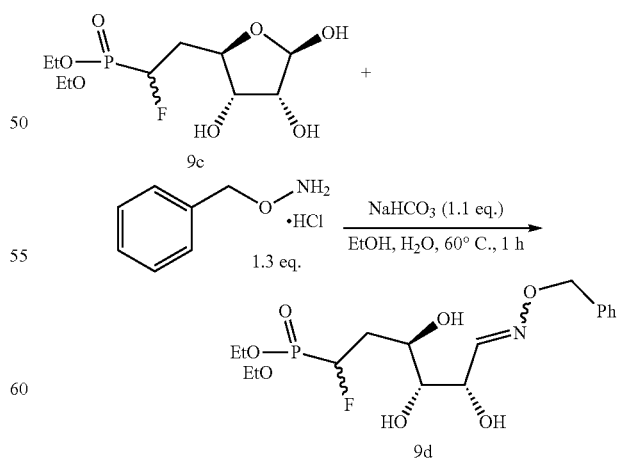

To a stirred solution of compound 9c (390 mg, 1.29 mmol) in H$_2$O (3 mL) obtained from previous step, was added EtOH (8 mL). Benzylhydroxylamine hydrochloride (271 mg, 1.68 mmol) and then NaHCO₂ (120 mg, 1.42 mmol) were added and the solution was heated to 60° C. and stirred for 1 h. The reaction mixture was concentrated under reduced pressure and the residue was purified by chromatography (SiO₂ column 15 g, CH₂Cl₂:EtOAc 20:80) to give the title compound (471 mg, 1.04 mmol, 81% isolated yield over two steps) as a colorless oil (assay=90%, estimated by ¹H NMR). The compound was obtained as a mixture of diastereomers in a ratio 1.5:1 and a mixture of oxime E and Z: 4:1.

¹H NMR (300 MHz, D₂O): δ 7.59 (d, 0.3H, J=6.9 Hz, HC=NOBn, minor diastereomer, E), 7.58 (d, 0.5H, J=6.9 Hz, HC=NOBn, major diastereomer, E), 7.48-7.38 (m, 5H, Ph), 6.91 (d, 0.08H, J=6 Hz, HC=NOBn, minor diastereomer, Z), 6.90 (d, 0.12H, J=6 Hz, HC=NOBn, major diastereomer, Z), 5.28-5.20 (m, 0.4H, —CHF—, minor diastereomer), 5.41 (s, 2H, OCH₂Ph), 5.10-5.02 (m, 0.6H, —CHF—, major diastereomer), 4.42-4.3.38 (m, 0.8H, major diastereomer), 4.31-4.20 (m, 4.2H, 2×OCH₂CH₃+0.2H), 3.89-3.69 (m, 2H), 2.35-2.08 (m, 2H), 1.35 (br t, 6H, J=7.2 Hz, 2×OCH₂CH₃)

LC-MS APCI⁺: C₂₂H₂₈FNO₇P [M+H]⁺ calculated 408.1. found 407.7.

Step 5: (6-Benzyloxyamino-1-fluoro-(3R,4R,5S)-3,4,5-trihydroxy-hexyl)-phosphonic acid diethyl ester (9e)

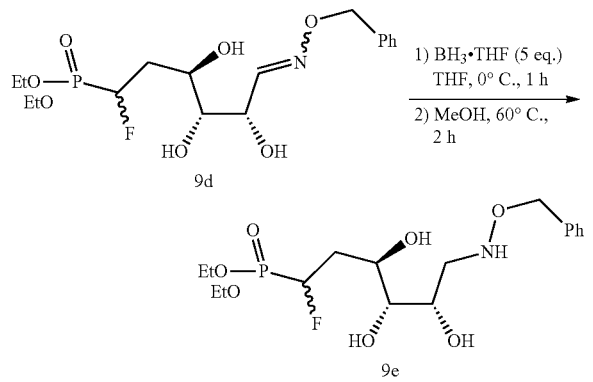

To a stirred solution of oxime 9d (843 mg, 1.86 mmol) in THF (9 mL) at 0° C. under nitrogen atmosphere was added dropwise BH₃.THF (1M, 9.3 mL, 9.3 mmol) via syringe pump over 10 min. The solution was stirred further at 0° C. for 1 hour until TLC (EtOAc:MeOH 90:10) and LC-MS indicated complete conversion. The reaction mixture was quenched carefully with MeOH (15 mL) at 0° C. (H₂ emission) and then heated at 60° C. for 2 hours. After cooling, the reaction mixture was concentrated under reduced pressure and the residue was purified by chromatography (SiO₂ column 15 g, EtOAc:MeOH 100:0 to 98:2) to give the title compound 9e (575 mg, 1.33 mmol, 71% isolated yield) as a colorless oil (assay=95%, estimated by ¹H NMR). The compound was obtained as a mixture of diastereomers in a ratio 1.5:1.

¹H NMR (300 MHz, D₂O): δ 7.47-7.37 (m, 5H, Ph), 5.31-5.10 (m, 1H, —CHF—), 4.76 (s, 2H, OCH₂Ph), 4.32-4.20 (m, 4H, 2×OCH₂CH₃), 3.98-3.97 (m, 2H), 3.64-3.59 (m, 1H), 3.27 (dd, 0.4H, J=2.7, 13.8 Hz, minor diastereomer), 3.26 (dd, 0.6H, J=2.7, 13.8 Hz, major diastereomer), 2.87 (dd, 0.6H, J=9.0, 13.7 Hz, major diastereomer), 2.86 (dd, 0.4H, J=9.0, 13.7 Hz, minor diastereomer), 2.36-1.74 (m, 2H), 1.35 (br t, 6H, J=8.0 Hz, 2×OCH₂CH₃)

LC-MS APCI⁺: C₂₂H₃₀FNO₇P [M+H]⁺ calculated 410.2. found 410.0.

Step 6: [6-(Benzyloxy-formyl-amino)-1-fluoro-(3R,4R,5S)-3,4,5-trihydroxy-hexyl]-phosphonic acid diethyl ester (9f)

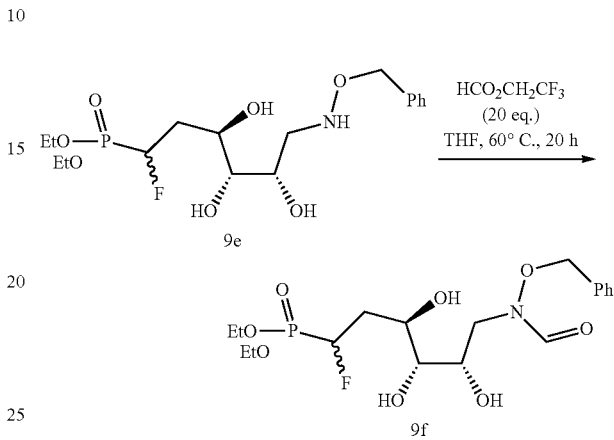

To a stirred solution of hydroxylamine 9e (545 mg, 1.26 mmol) in THF (5 mL) at 23° C. under nitrogen atmosphere was added trifluoroethyl formate (2.5 mL, 25.3 mmol). The solution was heated at 65° C. and stirred for 16 hours until TLC (AcOEt:MeOH 90:10) and LC-MS (APCI⁺) indicated complete conversion. After cooling at 23° C., the reaction mixture was concentrated under reduced pressure and the residue was purified by chromatography (SiO₂ column 15 g, CH₂Cl₂:MeOH 95:5) to give the title compound 9f (365 mg, 0.79 mmol, 63% isolated yield) as a white solid (assay=95%, estimated by ¹H NMR). The compound was obtained as a mixture of diastereomers in a ratio 55:45.

¹H NMR (250 MHz, D₂O): δ 8.13 (s, 0.25H, NC(=O)H, minor rotamer), 7.90 (s, 0.7H, NC(=O)H, major rotamer), 7.52-7.40 (m, 5H, Ph), 5.31-5.24 (m, 0.6H, —CHF—, major rotamer), 5.12-5.06 (m, 0.4H, —CHF—, minor rotamer), 4.97 (s, 2H, OCH₂Ph), 4.31-4.17 (m, 4H, 2×OCH₂CH₃), 4.02-3.84 (m, 2H), 3.73-3.48 (m, 3H), 2.27-2.04 (m, 2H), 1.33 (t, 3.6H, J=7.0 Hz, 2×OCH₂CH₃, major rotamer), 1.32 (t, 2.4H, J=7.0 Hz, 2×OCH₂CH₃, minor rotamer)

¹⁹F NMR (235 MHz, D₂O): δ −207.6 (d, J₃₁P-19F=79 Hz, 0.6F, major diastereomer), −213.2 (d, J₃₁P-19F=76 Hz, 0.4F, minor diastereomer)

LC-MS APCI⁺: C₂₈H₃₀FNO₈P [M+H]⁺ calculated 438.2. found 437.8.

Step 7: [1-Fluoro-6-(formyl-hydroxy-amino)-(3R,4R,5S)-3,4,5-trihydroxy-hexyl]-phosphonic acid diethyl ester (9 g)

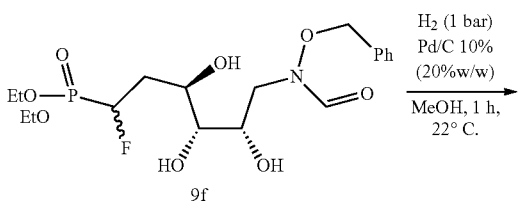

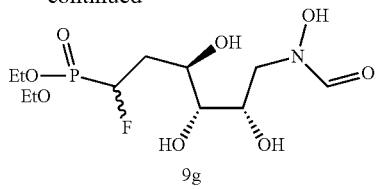

9g

In an autoclave, compound 9f (190 mg, 0.41 mmol) was dissolved in MeOH (1.8 mL). Pd/C 10% Degussa type E101 (38 mg) was added. The autoclave was purged three times with nitrogen (2 bar) and then three times with $H_2$ (2 bar). The pressure was set to 1 bar of $H_2$ and the reaction mixture was stirred at 22° C. for 1 hour. The autoclave was depressurized and purged with nitrogen. The reaction mixture was filtered over Celite® pad and the residue concentrated under reduced pressure to give the title compound (136 mg, 0.37 mmol, 90% isolated yield) as a white solid (assay=95%, estimated by $^1$H NMR) which was used without further purification. The compound was obtained as a mixture of diastereomers in a ratio 55:45.

$^1$H NMR (250 MHz, $D_2O$): δ 8.34 (s, 0.17H, NC(=O)H, minor rotamer), 7.90 (s, 0.8H, NC(=O)H, major rotamer), 5.34-5.26 (m, 0.55H, —CHF—, major rotamer), 5.15-5.07 (m, 0.45H, —CHF—, minor rotamer), 4.31-4.18 (m, 4H, 2×OCH$_2$CH$_3$), 4.06-3.86 (m, 2H), 3.77-3.58 (m, 3H), 2.32-1.73 (m, 2H), 1.33 (t, 6H, J=7.0 Hz, 2×OCH$_2$CH$_3$)

$^{31}$P NMR (101 MHz, $D_2O$): δ 20.5 (d, $J_{31P-19F}$=77 Hz, 0.45P, minor diastereomer), 19.8 (d, $J_{31P-19F}$=79 Hz, 0.55P, major diastereomer)

$^{19}$F NMR (235 MHz, $D_2O$): δ -207.5 (d, $J_{31P-19F}$=79 Hz, 0.55F, major diastereomer), -213.4 (d, $J_{31P-19F}$=76 Hz, 0.45F, minor diastereomer)

LC-MS APCI$^+$: C$_{11}$H$_{24}$FNO$_8$P [M+H]$^+$ calculated 348.1. found 347.9.

Step 8: [1-Fluoro-6-(formyl-hydroxy-amino)-(3R,4R,5S)-3,4,5-trihydroxy-hexyl]-phosphonic acid, monosodium salt (Example 9)

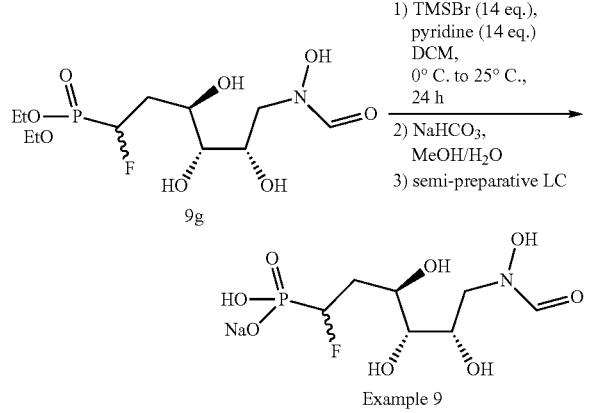

To a stirred suspension of 9g (90 mg, 0.25 mmol) in anhydrous CH$_2$Cl$_2$ (4 mL) at 0° C. under nitrogen atmosphere was added pyridine (160 μL, 1.97 mmol). TMSBr (268 μL, 1.97 mmol) was added dropwise over 5 min and the reaction mixture was stirred at 0° C. for 2 hours and then 15 hours at 5° C. At this time, starting material was still detected LC-MS (ESI$^-$). At 5° C., pyridine (120 μL, 1.47 mmol) and then TMSBr (200 μL, 1.47 mmol) were added. The reaction mixture was gradually warmed and stirred at 25° C. during 3 hours until LC-MS indicated complete conversion. The reaction mixture was concentrated under reduced pressure at 0° C. Water (2 mL) and MeOH (2 mL) were added to the residue at 0° C. and the mixture was neutralized with an aqueous solution of NaHCO$_3$ up to pH=7.5. The solution was stirred at 20° C. until complete desilylation as determined by LC-MS (ESI$^-$). The reaction mixture was then lyophilized and the resulting powder was purified by semi-preparative liquid chromatography (Column: Modulocart QS Strategy 10RP 21.2×250 mm, InterChim, gradient H$_2$O:CH$_3$CN 3:97 to 40:60 over 15 min, flow rate 12 mL/min, fraction size 5 mL, Detector: MS-ESI$^-$) to give the title compound (34 mg, 0.10 mmol, 40% isolated yield) as a white solid (assay=96%, estimated by $^1$H NMR; Area %=94%, TIC Mode in LC-MS). The compound was obtained as a mixture of diastereomers in a ratio 55:45.

$^1$H NMR (250 MHz, $D_2O$): δ 8.17 (s, 0.10H, NC(=O)H, minor rotamer), 7.71 (s, 0.75H, NC(=O)H, major rotamer), 4.70-4.59 (m, 1H, —CHF), 4.11-3.87 (m, 2H), 3.67-3.51 (m, 3H), 2.34-1.66 (m, 2H)

$^{31}$P NMR (101 MHz, $D_2O$): δ 12.3 (d, $J_{31P-19F}$=62 Hz, 0.45P, minor diastereomer), 12.0 (d, $J_{31P-19F}$=64 Hz, 0.55P, major diastereomer)

$^{19}$F NMR (235 MHz, $D_2O$): δ -200.3 (d, $J_{31P-19F}$=64 Hz, 0.55F, major diastereomer), -204.8 (d, $J_{31P-19F}$=62 Hz, 0.45F, minor diastereomer)

LC-MS ESI$^-$: C$_2$H$_{24}$FNO$_8$P [M-H]$^-$ calculated 290.0. found 290.0.

Example 10:
(3R,4S,5R)-3,4,5-trihydroxy-6-(N-hydroxyformamido)hexyl)phosphonic acid Step 1: Synthesis of (2R,3S,4S)-5,5-bis(ethylthio)pentane-1,2,3,4-tetraol (10a)

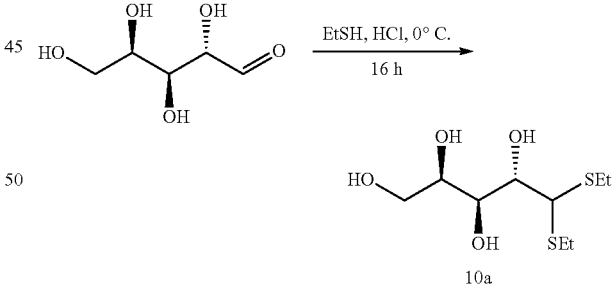

10a

To a cooled solution (0° C.) of D-Lyxose (20 g, 133.33 mmol) in conc. HCl (80 mL) was added ethanethiol (16.56 g, 266.66 mmol) dropwise. The reaction mixture was stirred at 0° C. for 16 h. The reaction mixture was poured into 200 ml methanol and neutralized with lead carbonate. Lead salts were than filtered and filtrate was evaporated under vacuum to obtain title compound 10a (28.8 g, 84.7%) as light brown solid.

ES-MS (M+NH$_4$) 274.

$^1$H NMR (400 MHz, DMSO-d$_6$): δ 4.99 (d, 1H, J=6.0 Hz), 4.47 (t, 1H, J=11.2 Hz), 4.25-4.17 (m, 3H), 3.83 (t, 1H,

J=15.2 Hz), 3.73-3.68 (q, 1H, J=18.8 Hz), 3.54 (t, 1H, J=16.8 Hz), 3.43-3.36 (m, 2H), 2.66-2.61 (m, 4H), 1.21-1.16 (m, 6H).

Step 2: Synthesis of (2S,3S,4R)-1,1-bis(ethylthio)-5-((triisopropylsilyl)oxy)pentane-2,3,4-triol (10b)

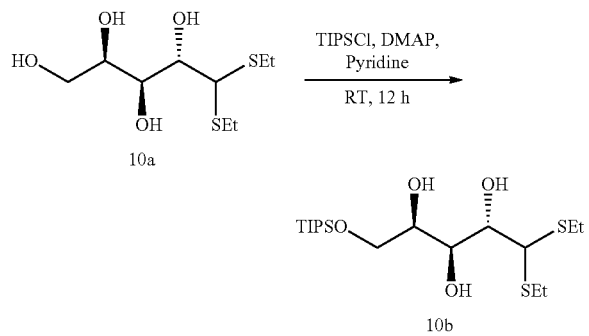

To a stirred solution of 10a (28.5 g, 111.32 mmol) in Pyridine (300 mL) was added 4-dimethylaminopyridine (13.5 g, 111.32 mmol) and triisopropylsilylchloride (21.4 g, 111.32 mmol). The reaction mixture was stirred at RT for 12 h. The reaction mixture was concentrated under reduced pressure. The crude reaction mixture was diluted with water, extracted with ethylacetate, dried over anhydrous sodium sulfate, filter and concentrated under reduced pressure to obtain crude product which was purified by column chromatography on silica gel (100-200 mesh) and 0-50% EtOAc:n-hexane as eluent to afford the title product 10b (36.0 g, 78.0%) as light yellow liquid.

$^1$H NMR (400 MHz, DMSO-$d_6$): δ 4.97 (d, 1H, J=6.0 Hz), 4.28 (d, 1H, J=6.4 Hz), 4.20 (s, 1H), 4.16 (d, 1H, J=8.8 Hz), 3.80-3.59 (m, 5H), 2.64-2.59 (m, 4H), 1.21-1.14 (m, 6H), 1.08-0.98 (m, 21H).

Step 3: Synthesis of triisopropyl(((2R,3S,4S)-2,3,4-tris(benzyloxy)-5,5-bis(ethylthio)pentyl)oxy)silane (10c)

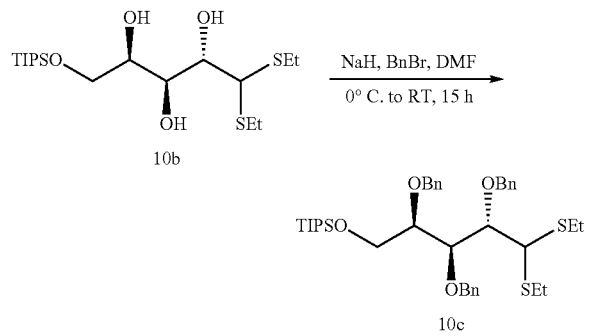

To a cooled solution (0° C.) of 10b (36.0 g, 87.37 mmol) in DMF (200 mL) was added NaH (60% in mineral oil) (9.78 g, 244.66 mmol) in portions over a period of 15 min. The reaction mixture was stirred at 0° C. for 15 min. Benzyl bromide (41.8 g, 244.66 mmol) was added dropwise in to the reaction mixture. The reaction mixture was stirred at RT for 15 h and was poured in ice cold water, extracted with ethyl acetate, dried over anhydrous sodium sulfate, filtered and concentrated under reduced pressure to obtain crude product. The latter was purified by column chromatography on silica gel (100-200 mesh) and 0-10% EtOAc:n-hexane as eluent to afford the title product 10c (38.0 g, 63.7%) as light yellow oil.

$^1$H NMR (400 MHz, DMSO-$d_6$): δ 7.37-7.24 (m, 15H), 4.96 (d, 1H, J=11.2 Hz), 4.71 (s, 2H), 4.63 (d, 1H, J=11.6 Hz), 4.48-4.43 (m, 2H), 4.27 (d, 1H, J=1.2 Hz), 4.07 (d, 2H, J=4.0 Hz), 3.90-3.77 (m, 3H), 2.66-2.59 (m, 4H), 1.18-1.12 (m, 6H), 1.07-0.94 (m, 21H).

Step 4: Synthesis of (2S,3S,4R)-2,3,4-tris(benzyloxy)-5-((triisopropylsilyl)oxy)pentanal (10d)

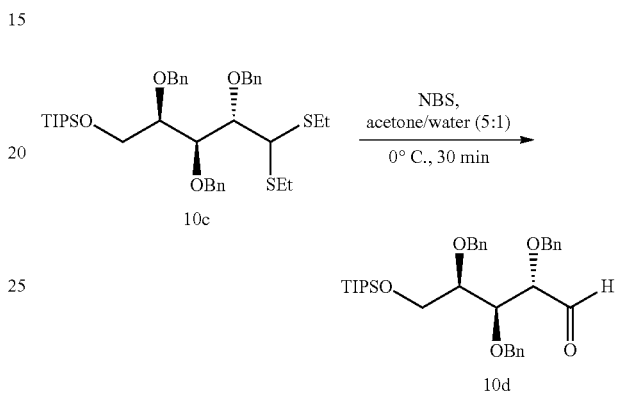

To a cooled solution (0° C.) of 10c (38.0 g, 55.63 mmol) in acetone:water (5:1) (240 mL) was added NBS (49.5 g, 278.1 mmol) in portions over a period of 15 min. The reaction mixture was stirred at 0° C. for 30 min. The reaction mixture was concentrated under reduced pressure. The crude reaction mixture was quenched with saturated NaHCO$_3$ solution and Na$_2$S$_2$O$_3$ solution, extracted with ethyl acetate, dried over anhydrous sodium sulfate, filter and concentrated under reduced pressure to afford the desired product 10d (31.2 g, 97%) which was used as such for next step without further purification. ESMS (M+NH$_4$) 594.

Crude $^1$H NMR (400 MHz, DMSO-$d_6$): δ 9.65 (s, 1H), 7.36-7.25 (m, 15H), 4.70-4.45 (m, 6H), 4.29 (d, 1H, J=2.4 Hz), 4.07 (t, 1H, J=7.6 Hz), 3.89 (d, 1H, J=4.0 Hz), 3.80-3.75 (m, 2H), 1.06-0.93 (m, 21H).

Step 5: Synthesis of O-benzyl-N-((2R,3R,4R)-2,3,4-tris(benzyloxy)-5-((triisopropylsilyl)oxy)pentyl)hydroxylamine (10e)

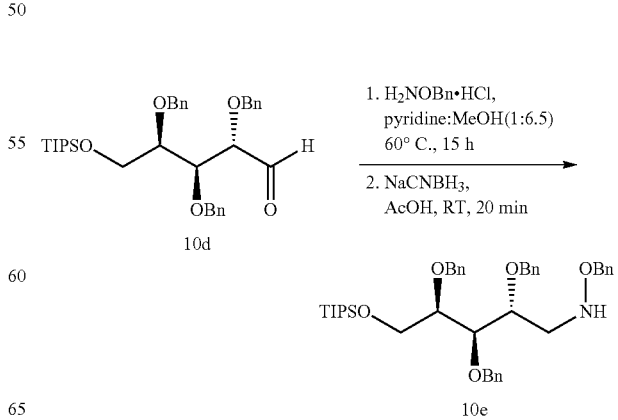

To a stirred solution of 10d (30.0 g, 52.08 mmol) in pyridine:MeOH (1:6.5) (150 mL) was added O-Benzyl hydroxylamine hydrochloride (12.4 g, 78.12 mmol). The reaction mixture was stirred at 60° C. for 15 h. The reaction mixture was concentrated under reduced pressure, the crude product was purified by column chromatography using combiflash silica gel column (100 g) and 0-10% EtOAc:n-hexane as eluent to afford intermediate oxime (25 g) as colourless oil. The intermediate oxime (25 g) was dissolved in acetic acid (130 mL) and sodium cyanoborohydride (12.9 g, 208.33 mmol) was added in portions to the reaction mixture. The reaction mixture was stirred for 20 min at RT. The reaction mixture was diluted with water, extracted with DCM, washed with saturated NaHCO$_3$ solution, dried over anhydrous sodium sulfate, filtered and concentrated under reduced pressure. The crude reaction mixture was purified by column chromatography on silica gel (100-200 mesh) and 0-10% EtOAc:n-hexane as eluent to afford title product 10e (18.0 g, 53%) as colorless oil, ESMS(M+H) 684.47.

$^1$H NMR (400 MHz, CDCl$_3$): δ 7.38-7.26 (m, 20H), 5.92-5.92 (bs, 1H), 4.75-4.50 (m, 8H), 4.00-3.93 (m, 2H), 3.80-3.79 (m, 2H), 3.66-6.63 (m, 1H), 3.32-3.31 (m, 1H), 3.20-3.16 (m, 1H), 1.09-0.98 (m, 21H).

Step 6: Synthesis of N-(benzyloxy)-N-((2R,3R,4R)-2,3,4-tris(benzyloxy)-5-((triisopropylsilyl)oxy)pentyl)formamide (10f)

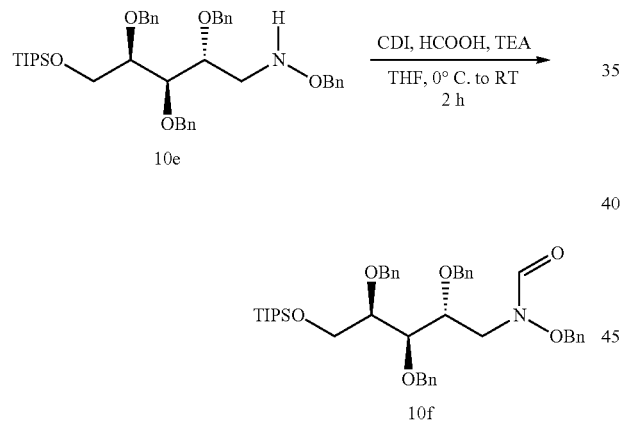

To a cooled solution (0° C.) of Carbonyldiimidazole (15.3 g, 95.02 mmol) in THF (100 mL) was added formic acid (3.36 g, 73.09 mmol) and TEA (2.95 g, 29.23 mmol). The reaction mixture was stirred at 0° C. for 30 min. 10e (10 g, 14.61 mmol) was dissolved in THF (20 mL) and added dropwise to the reaction mixture. The reaction mixture was stirred at RT for 2 h, diluted with water, extracted with ethyl acetate, dried over anhydrous sodium sulfate, filtered and concentrated under reduced pressure. The crude product was purified using combiflash silica gel column (100 g) and 0-20% EtOAc:n-hexane as eluent to afford the title product 10f (6.5 g, 62.5%) as colorless oil. ES-MS (M+H) 712.40.

$^1$H NMR (400 MHz, CDCl$_3$): δ 8.18-7.91 (bs, 1H), 7.32-7.26 (m, 20H), 4.95-4.39 (m, 8H), 4.11-3.67 (m, 5H), 3.49 (bs, 2H), 1.03-0.92 (m, 21H).

Step 7: Synthesis of N-(benzyloxy)-N-((2R,3R,4R)-2,3,4-tris(benzyloxy)-5-hydroxypentyl)formamide (10g)

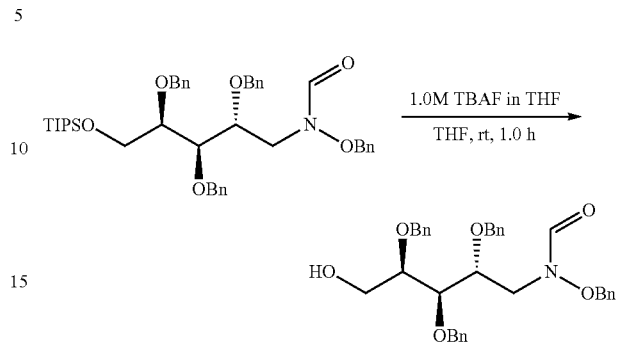

To a stirred solution of 10f (6.5 g, 9.129 mmol) in THF (45 ml) was added TBAF (1.0M in THF) (13.6 ml, 13.69 mmol) dropwise. The reaction mixture was stirred at RT for 30 min, diluted with water, extracted with ethyl acetate, dried over anhydrous sodium sulfate, filtered and concentrated under reduced pressure. The crude reaction mixture was purified by column chromatography on silica gel (100-200 mesh) and 0-30% EtOAc:n-hexane as eluent to afford title product 10g (4.6 g, 90.0%) as colorless oil. ES-MS (M+H) 556.2.

$^1$H NMR (400 MHz, DMSO-d$_6$): δ 8.27-7.97 (bs, 1H), 7.36-7.25 (m, 20H), 4.89-4.82 (m, 3H), 4.70-4.67 (m, 3H), 4.53-4.38 (m, 3H), 3.94-3.90 (m, 2H), 3.70-3.63 (m, 4H), contaminated with ethyl acetate.

Step 8: Synthesis of N-(benzyloxy)-N-((2R,3R,4S)-2,3,4-tris(benzyloxy)-5-oxopentyl)formamide (10h)

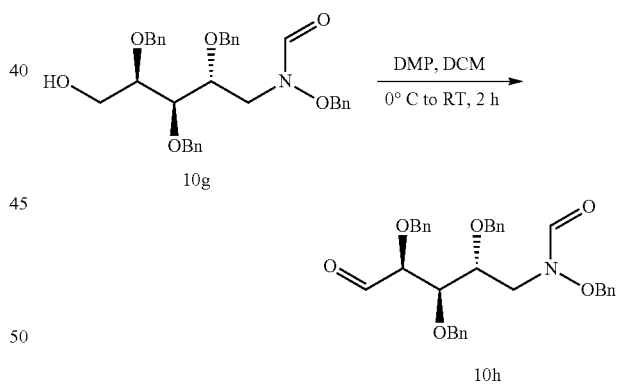

To a stirred solution of 10g (1.5 g, 2.702 mmol) in DCM at 0° C. was added Dess-Martin Periodinane (1.7 g, 4.054 mmol) in portions. The reaction mixture was stirred at RT for 5 h, then quenched with NaHCO$_3$ solution and filtered through celite bed. The reaction mixture was extracted with DCM, dried over anhydrous sodium sulfate, filtered and concentrated under reduced pressure. The crude product was purified using combiflash silica gel column (40 g) and 0-50% EtOAc:n-hexane as eluent to afford the pure product, N-(benzyloxy)-N-((2R,3R,4S)-2,3,4-tris(benzyloxy)-5-oxopentyl)formamide (0.85 g, 60%) as colorless oil. ESMS (M+NH$_4$) 571.27.

$^1$H NMR (400 MHz, CDCl$_3$): δ 9.68-9.67 (bs, 1H, CHO), 8.17-7.88 (bs, 1H, CHO), 7.34-7.24 (m, 20H), 4.95-4.92 (bs,

1H), 4.71-4.68 (d, 2H, J=11.6 Hz), 4.55-4.41 (m, 5H), 4.02-3.94 (m, 4H), 3.61-3.59 (bs, 1H).

Step 9: Synthesis of dimethyl((3R,4S,5R,E)-3,4,5-tris(benzyloxy)-6-(N-(benzyloxy)formamido)hex-1-en-1-yl)phosphonate (10i)

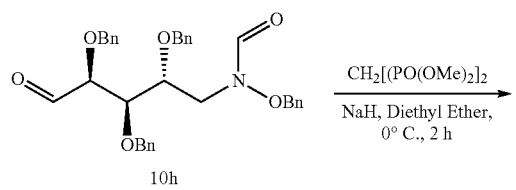

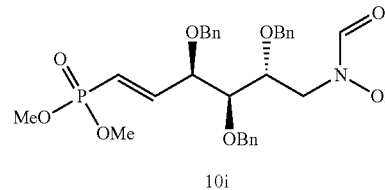

To a cooled solution (0° C.) of tetramethyl methylenediphosphonate (0.534 g, 2.305 mmol) in diethyl ether (8 mL) was added NaH (60% in mineral oil) (0.092 g, 2.305 mmol). The reaction mixture was stirred at 0° C. for 40 min. Compound 10h (0.85 g, 1.537 mmol) was dissolved in diethyl ether (2 mL) and added dropwise to the reaction mixture. The reaction mixture was quenched with water, extracted with ethyl acetate, dried over anhydrous sodium sulfate, filtered and concentrated under reduced pressure. The crude reaction mixture was purified by flash chromatography on silica gel column (40 g) and 0-5% MeOH:DCM as eluent to afford title product 10i (0.75 g, 75%) as colorless oil. ESMS(M+H) 660.11.

$^1$H NMR (400 MHz, DMSO-d$_6$): δ 8.20-7.95 (bs, 1H, NCHO), 7.35-7.23 (m, 20H), 6.73 (bs, 1H), 6.09 (bs, 1H), 4.88-4.64 (m, 2H), 4.61-4.38 (m, 7H), 3.94 (s, 1H), 3.82 (bs, 1H), 3.67-3.64 (m, 2H), 3.60-3.53 (m, 6H).

Step 10: Synthesis of dimethyl((3R,4S,5R)-3,4,5-tris(benzyloxy)-6-(N-(benzyloxy)formamido) hexyl) phosphonate (10j)

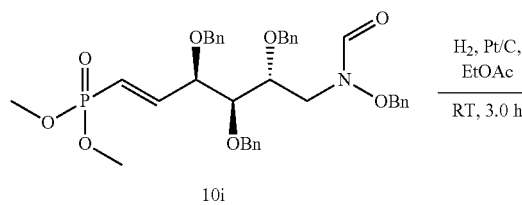

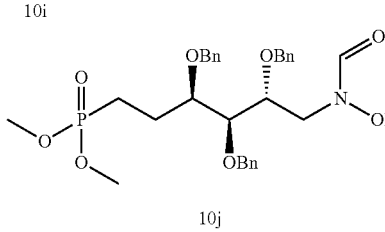

To a stirred solution of 10i (0.74 g, 1.122 mmol) in ethyl acetate (15 ml) was added 10% Pt/C (0.38 g). The reaction mixture was stirred under H$_2$ atmosphere for 3 h, then filtered through celite bed and filtrate was concentrated under reduced pressure to obtain crude product, which was further purified flash chromatography using silica gel column (40 g) and 0-5% MeOH:DCM as eluent to afford title product 10j (0.56 g, 75.6%) as colorless oil. ESMS(M+NH$_4$) 679.21. $^1$H NMR (400 MHz, DMSO-d$_6$): δ 8.27-7.99 (bs, 1H), 7.36-7.27 (m, 20H), 4.87-4.82 (m, 2H), 4.70-4.26 (m, 6H), 4.04-4.00 (m, 1H), 3.40-3.82 (m, 2H), 3.63-3.55 (m, 8H), 1.78-1.56 (m, 4H).

Step 11: Synthesis of ((3R,4S,5R)-3,4,5-tris(benzyloxy)-6-(N-(benzyloxy)formamido)hexyl)phosphonic acid (10k)

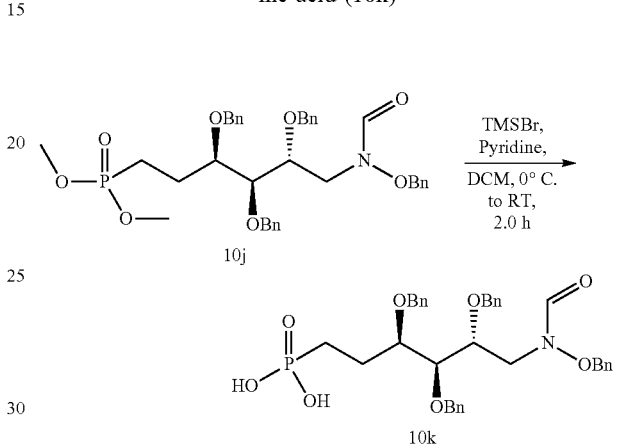

To a cooled (0° C.) solution of 10j (0.55 g, 0.832 mmol) in DCM (10 mL) were added pyridine (0.394 g, 4.99 mmol) and trimethylsilylbromide (0.763 g, 4.99 mmol). The reaction mixture was stirred at 0° C. to RT for 2 h, then quenched by saturated NaHCO$_3$ solution, extracted with DCM, dried over anhydrous sodium sulfate, filtered and concentrated under reduced pressure to afford the pure product 10k (0.45 g, 85.7%) as white solid. ESMS(M–H) 632.41. $^1$H NMR (400 MHz, DMSO-d$_6$): δ 8.20-7.94 (bs, 1H), 7.24-6.86 (m, 20H), 4.84-4.34 (m, 8H), 3.84-3.57 (m, 5H), 1.87-1.76 (m, 2H), 1.39-1.37 (m, 2H).

Step 12: Synthesis of ((3R,4S,5R)-3,4,5-trihydroxy-6-(N-hydroxyformamido) hexyl)phosphonic acid Example 10

To a stirred solution of 10k (0.2 g, 0.315 mmol) in the mixture of THF (10 mL) and 5% acetic acid in water (2 mL) was added palladium hydroxide Pd(OH)$_2$ (0.053 g, 0.379 mmol). The reaction mixture was stirred under hydrogen atmosphere for 14 h. After every 3 h the reaction mixture was filtered and fresh Pd(OH)$_2$ (0.053 g, 0.379 mmol) was added. The reaction progress was monitored by direct mass. The reaction mass was filtered by a micro filter, concentrated and crude compound was further purified by prep HPLC with Zic Hillic (19×250 mm, 5 μm) column with 20:80 5 mM ammonium acetate:ACN, flow rate 25 mL and desired fraction was lyophilized to obtain title compound, ((3R,4S,5R)-3,4,5-trihydroxy-6-(N-hydroxyformamido) hexyl)phosphonic acid (0.024 g, 28%) as off white solid.

$^1$H NMR (400 MHz, D$_2$O): δ 7.83 (s, 1H, NCHO), 3.93-3.89 (m, 1H), 3.75-3.65 (m, 2H), 3.61-3.53 (m, 1H), 3.41-3.40 (m, 1H), 1.69-1.46 (m, 4H). $^{31}$P NMR D$_2$O: δ 23.96 ES-MS (M−H) 272.0.

Example 11: (3R,4R,5R)-3,4,5-trihydroxy-6-(N-hydroxyformamido)hexylphosphonic acid Step 1: (2R,3R,4S)-5,5-bis(ethylthio)pentane-1,2,3,4-tetraol (11a)

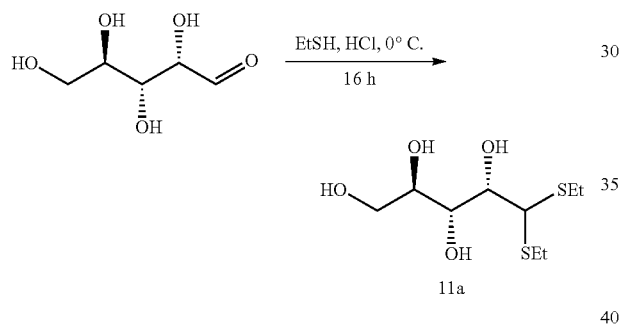

To a cooled solution (0° C.) of (2S,3R,4R)-2,3,4,5-tetrahydroxypentanal (50 g, 333.33 mmol) in conc. HCl (500 mL) was added ethanethiol (41.88 g, 666.66 mmol) dropwise. The reaction mixture was stirred at 0° C. for 16 h, then taken in methanol and neutralized with lead carbonate. Lead salts were filtered and filtrate was concentrated under reduced pressure to obtain title compound 11a (70.01 g, 83.04%) as light brown solid.

$^1$H NMR (400 MHz, DMSO-d$_6$) δ 4.59 (d, 1H, J=7.2 Hz), 4.55 (d, 1H, J=4.4 Hz), 4.50-4.33 (m, 2H), 4.02-4.00 (d, 1H, J=8.8 Hz), 3.73-3.69 (t, 2H, J=8.0 Hz), 3.61-3.44 (m, 1H) 3.44-3.34 (m, 2H), 2.65-2.50 (m, 4H), 1.19-1.16 (t, 6H, J=7.6 Hz).

Step 2: (2S,3R,4R)-1,1-bis(ethylthio)-5-(triisopropylsilyloxy)pentane-2,3,4-triol (11b)

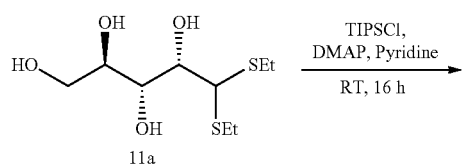

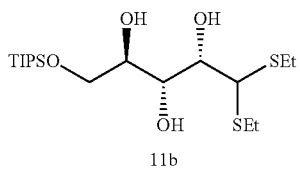

To a stirred solution of 11a (50 g, 292.53 mmol) in pyridine (500 mL) was added 4-dimethylaminopyridine (35.74 g, 0.76 mmol) and triisopropylsilylchloride (37.59 g, 195.02 mmol). The reaction mixture was stirred at RT for 16 h and concentrated under reduced pressure. The crude residue was diluted with water, extracted with ethyl acetate, dried over anhydrous sodium sulfate, filter and concentrated under reduced pressure to obtain crude product which was purified by column chromatography on silica gel (100-200 mesh) and 0-20% ethyl acetate in hexane as eluent to afford the title product 11b (70.0 g, 87.5%) as colorless oil.

ES-MS (m/z) (M−1): 411.17.

$^1$H NMR (400 MHz, DMSO-d$_6$): δ 4.63 (d, 1H, J=7.2 Hz), 4.43 (d, 1H, J=5.6 Hz), 4.31 (d, 1H, J=8.0 Hz), 4.01 (d, 1H, J=8.8 Hz), 3.87 (t, 1H, J=7.2 Hz), 3.78-3.74 (m, 2H), 3.67-3.63 (m, 1H), 3.52-3.47 (m, 1H) 2.65-2.59 (m, 4H), 1.19-1.15 (m, 6H), 1.10-0.99 (m, 21H).

Step 3: Triisopropyl((2R,3R,4S)-2,3,4-tris(benzyloxy)-5,5-bis(ethylthio)pentyloxy)silane (11c)

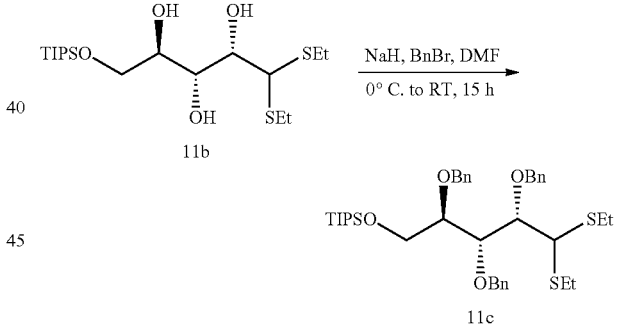

To a cooled solution (0° C.) of 11b (40.0 g, 96.92 mmol) in DMF (500 mL) was added NaH (6.97 g, 290.75 mmol) in portions over a period of 15 min. The reaction mixture was stirred at 0° C. for 15 min. Benzyl bromide (49.8 g, 290.75 mmol) was added dropwise to the reaction mixture and the latter was stirred at RT for 15 h, then poured in ice cold water, extracted with ethyl acetate, dried over anhydrous sodium sulfate, filtered and concentrated under reduced pressure to obtain crude product. Purification by column chromatography on silica gel (100-200 mesh) and 0-5% ethyl acetate in hexane as eluent afforded the title product 11c (34.5 g, 51.12%) as colorless oil.

$^1$H NMR (400 MHz, DMSO-d$_6$): δ 7.35-7.26 (m, 15H), 4.78-4.65 (m, 4H), 4.55-4.46 (m, 2H), 4.18-3.65 (m, 6H), 2.69-2.54 (m, 4H), 1.17-0.98 (m, 27H).

Step 4: (2S,3R,4R)-2,3,4-tris(benzyloxy)-5-(triiso-propylsilyloxy)pentanal (11d)

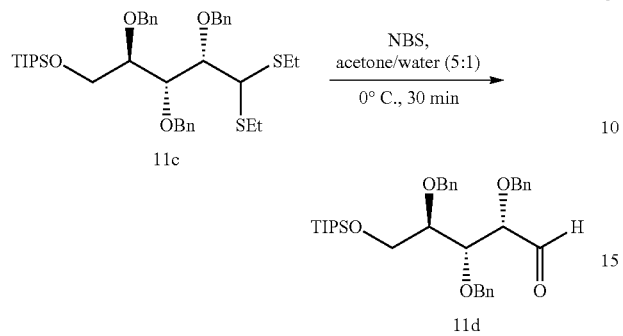

To a cooled solution (0° C.) of 11c (25.0 g, 36.65 mmol) in acetone:water (5:1) (300 mL) was added NBS (36.62 g, 183.26 mmol) in portions over a period of 15 min. The reaction mixture was stirred at 0° C. for 30 min. The reaction mixture was concentrated under reduced pressure. The crude reaction mixture was quenched with saturated NaHCO$_3$ solution and Na$_2$S$_2$O$_3$ solution, extracted with ethyl acetate, dried over anhydrous sodium sulfate, filtered and concentrated under reduced pressure to afford the desired product 11d (17.88 g) which was used as such for next step without further purification.

$^1$H NMR (400 MHz, CDCl$_3$): δ 9.70-9.65 (t, 1H, J=21.6 Hz), 7.44-7.27 (m, 15H), 4.71-4.41 (m, 6H), 4.10-4.05 (m, 2H), 3.77-3.73 (m, 3H), 1.07-1.01 (m, 21H).

Step 5: O-benzyl-N-((2R,3S,4R)-2,3,4-tris(benzyloxy)-5-(triisopropylsilyloxy)pentyl)hydroxylamine (11e)

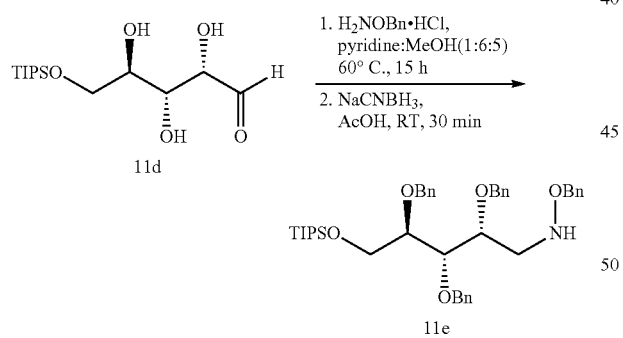

To a stirred solution of crude 11d (17.7 g, 30.68 mmol) in pyridine:MeOH (1:6.5) (200 mL) was added O-Benzyl hydroxylamine hydrochloride (7.32 g, 46.02 mmol). The reaction mixture was stirred at 60° C. for 15 h. The reaction mixture was concentrated under reduced pressure The crude product was purified by column chromatography using combiflash silica gel column (100 g) and 0-10% EtOAc:n-hexane as eluent to afford intermediate oxime (15 g) as colorless oil. The intermediate oxime (14.9 g) obtained was dissolved in acetic acid (150 ml) and sodium cyanoborohydride (7.7 g, 122.5 mmol) was added in portions to the reaction mixture. The reaction mixture was stirred for 30 min at RT, then diluted with water, extracted with DCM, washed with saturated NaHCO$_3$ solution, dried over anhydrous sodium sulfate, filtered and concentrated under reduced pressure. The crude reaction mixture was purified by column chromatography on silica gel (100-200 mesh) and 0-10% ethyl acetate in hexane as eluent to afford title product 11e (12.0 g, 60%) as colorless oil.

ES-MS (m/z) (M+1): 684.58.

$^1$H NMR (400 MHz, CDCl$_3$): δ 7.35-7.22 (m, 20H), 5.85-5.82 (bs, 1H), 4.77-4.48 (m, 8H), 4.06-3.76 (m, 5H), 3.36-3.17 (m, 1H), 3.09-2.91 (m, 1H), 1.10-1.01 (m, 21H).

Step 6: N-(benzyloxy)-N-((2R,3S,4R)-2,3,4-tris(benzyloxy)-5-(triisopropylsilyloxy)pentyl)formamide (11f)

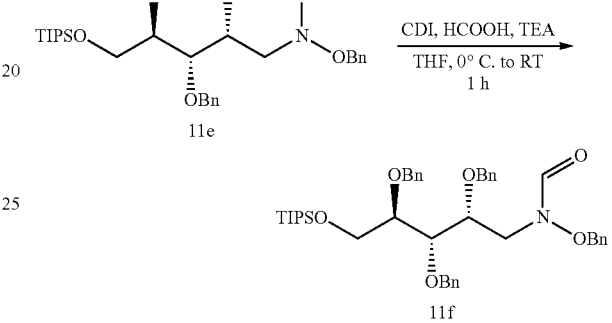

To a cooled solution (0° C.) of carbonyldiimidazole (12.7 g, 78.87 mmol) in THF (100 mL) were added formic acid (2.79 g, 60.67 mmol) and TEA (2.45 g, 12.13 mmol). The reaction mixture was stirred at 0° C. for 30 min. Compound 11e (8.3 g, 12.13 mmol) was dissolved in THF (20 mL) and added dropwise to the reaction mixture. The reaction mixture stirred at RT for 2 h, diluted with water, extracted with ethyl acetate, dried over anhydrous sodium sulfate, filtered and concentrated under reduced pressure. The crude product was purified using combiflash column chromatography on silica gel (100 g) and 0-20% EtOAc:n-hexane as eluent to afford the title product 11f (10.2 g, 77.2%) as colorless oil.

ES-MS (m/z) (M+1): δ 84.58.

$^1$H NMR (400 MHz, DMSO-d$_6$): δ 8.31 and 7.96 (2×s, 1H, 1:1 rotamers, N—CHO), 7.47-7.23 (m, 20H), 4.91-4.44 (m, 8H), 4.12-3.54 (m, 7H), 1.09-0.97 (m, 21H).

Step 7: N-(benzyloxy)-N-((2R,3S,4R)-2,3,4-tris(benzyloxy)-5-hydroxypentyl)formamide (11g)

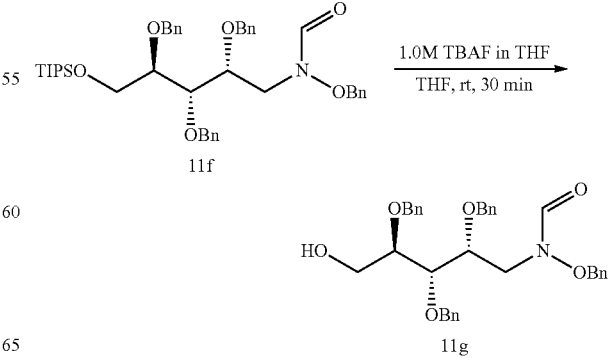

To a stirred solution of 11f (10.0 g, 18.56 mmol) in THF (60 ml) was added TBAF (1.0M in THF) (6 ml) dropwise. The reaction mixture was stirred at RT for 30 min, then diluted with water, extracted with ethyl acetate, dried over anhydrous sodium sulfate, filtered and concentrated under reduced pressure. The crude residue was purified by column chromatography on silica gel (100-200 mesh) and 0-30% ethyl acetate in hexane as eluent to afford title product 11g (7.1 g, 91%) as colorless oil.

ES-MS (m/z) (M+NH$_4$): 573.

$^1$H NMR (400 MHz, DMSO-d$_6$): δ 8.30 and 7.96 (s, 1H, 1:1 rotamers, N—CHO), 7.39-7.21 (m, 20H), 4.91-4.42 (m, 8H), 4.06-3.52 (m, 7H).

Step 8: N-(benzyloxy)-N-((2R,3S,4S)-2,3,4-tris(benzyloxy)-5-oxopentyl)formamide (11h)

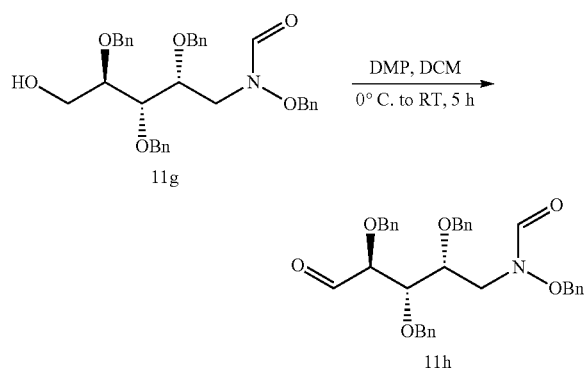

To a stirred solution of 11g (6.9 g, 12.43 mmol) in DCM (100 mL) at 0° C. was added Dess-Martin periodinane (10.54 g, 12.43 mmol) in portions. The reaction mixture was stirred at RT for 5 h, then quenched with NaHCO$_3$ solution and filtered through celite bed. The filtrate was extracted with DCM, dried over anhydrous sodium sulfate, filtered and concentrated under reduced pressure. The crude residue was purified using combiflash silica gel column (40 g) and 0-50% EtOAc:n-hexane as eluent to afford the pure product 11h (3.3 g, 48.5%) as colorless oil. ES-MS (m/z) (M+NH$_4$): 571.12.

$^1$H NMR (400 MHz, CDCl$_3$): δ 9.69 and 9.58 (s, 1H, rotamers of CHO), 8.18 and 7.88 (s, 1H, rotamers of N—CHO), 7.44-7.21 (m, 20H), 4.97-3.71 (m, 13H).

Step 9: Dimethyl(3R,4R,5R,E)-3,4,5-tris(benzyloxy)-6-(N-(benzyloxy)formamido)hex-1-enylphosphonate (11i)

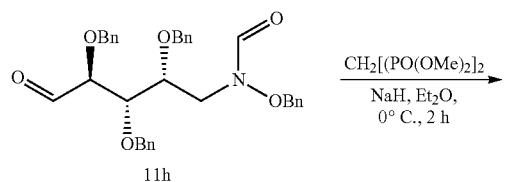

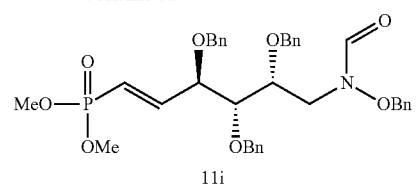

To a cooled solution (0° C.) of tetramethyl-methylenediphosphonate (2.01 g, 8.95 mmol) in diethyl ether (20 mL) was added NaH (60% in mineral oil) (0.208 g, 6.9 mmol). The reaction mixture was stirred at 0° C. for 40 min. Compound 11h (3.2 g, 5.7 mmol) was dissolved in diethyl ether (5 ml) and added dropwise to the reaction mixture. The latter was stirred at 0° C. for 1 hr, then quenched with water, extracted with ethyl acetate, dried over anhydrous sodium sulfate, filtered and concentrated under reduced pressure. The crude reaction mixture was purified by flash chromatography using silica gel column (40 g) and 0-80% ethyl acetate in hexane as eluent to afford pure title product 11i (2.1 g, 55.40%) as a colorless oil.

ES-MS (m/z) (M+1): δ 60.46. LC-MS consistent with desired product.

$^1$H NMR (400 MHz, CDCl$_3$): δ 8.17 and 7.73 (2×s, 1H, 1:1 rotamers, N—CHO), 7.34-7.26 (m, 20H), 6.91 (br s, 1H), 6.02 (br s, 1H), 4.88-3.51 (m, 19H), mixture of isomers.

Step 10: Dimethyl(3R,4R,5R)-3,4,5-tris(benzyloxy)-6-(N-(benzyloxy) formamido)hexylphosphonate (11j)

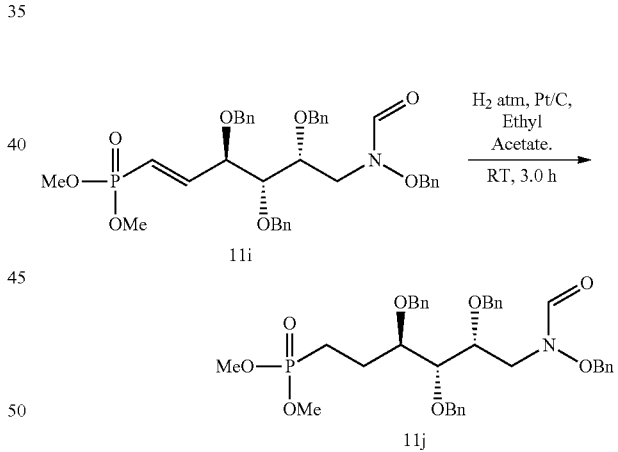

To a stirred solution of 11i (2.0 g, 3.025 mmol) in ethyl acetate (20 ml) was added 10% Pt/C (1 g). The reaction mixture was stirred under H$_2$ atmosphere for 3 h, then filtered through celite bed. Filtrate was concentrated under reduced pressure to obtain crude product, which was further purified flash chromatography using silica gel column (40 g) and 0-100% ethyl acetate in hexane as eluent to afford pure product 11j (1.7 g, 85%) as light yellow oil.

ES-MS (m/z) (M+1): δ 62.45.

$^1$H NMR (400 MHz, CDCl$_3$) δ 8.19 and 7.82 (s, 1H, 1:1 rotamers, N—CHO), 7.33-7.26 (m, 20H), 4.79-4.41 (m, 8H), 3.91-3.33 (m, 11H), 2.05-1.64 (m, 4H).

Step 11: Ethyl((3R,4R,5R)-3,4,5-tris(benzyloxy)-6-(N-hydroxyformamido)hexyl)phosphinic acid (11k)

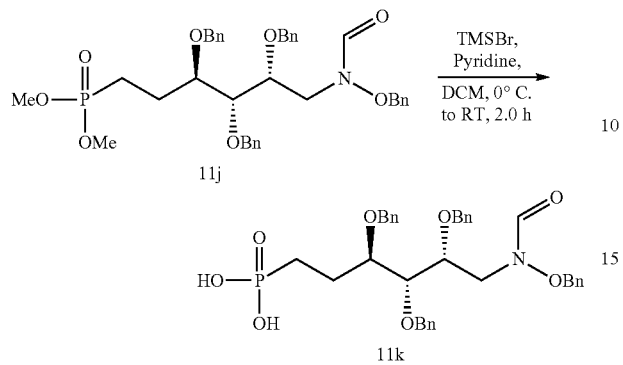

To a cooled (0° C.) solution of 11j (1.6 g, 2.42 mmol) in DCM (20 mL) was added pyridine (1.14 g, 14.52 mmol) and trimethylsilylbromide (2.22 g, 14.52 mmol). The reaction mixture was stirred at RT for 2 h, then quenched with saturated NaHCO₃ solution, extracted with DCM, dried over anhydrous sodium sulfate, filtered and concentrated under reduced pressure to afford the 11k product (1.2 g, 78.13%) as light brown solid.

ES-MS (m/z) (M+1): δ 34.40.

$^1$H NMR (400 MHz, DMSO-d$_6$): δ 8.24 and 7.92 (2×bs, 1H, rotamers of NCHO), 7.30-7.23 (m, 20H), 4.92-4.87 (m, 2H), 4.68-4.59 (m, 1H), 4.56-4.34 (m, 5H), 4.01-3.27 (m, 5H), 2.08-2.03 (m, 2H), 1.89-1.43 (m, 2H).

Step 12: (3R,4R,5R)-3,4,5-trihydroxy-6-(N-hydroxyformamido)hexylphosphonic acid (Example 11)

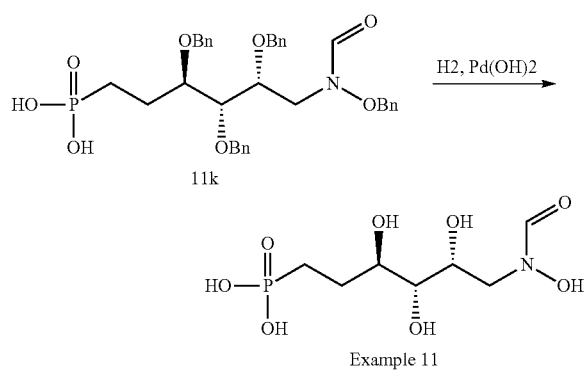

To a stirred solution of 11k (0.8 g, 1.26 mmol) in THF (15 mL) and 5% Acetic acid in water (3 mL) was added Pd(OH)₂ (0.212 g, 1.51 mmol). The reaction mixture was stirred under hydrogen atmosphere for 14 h. After every 3 h the reaction mixture was filtered and fresh Pd(OH)₂ (0.212 g, 1.51 mmol) was added, the reaction progress was monitored by direct mass. The reaction mass was filtered by a micro filter, concentrated and crude compound was further purified by prep HPLC with Zic-Hilic column (19×250 mm, 5 μm, gradient MeCN/5M ammonium acetate, 80 to 30%, flow rate 25 mL/min) and desired fraction was lyophilized to obtain title compound (3R,4R,5R)-3,4,5-trihydroxy-6-(N-hydroxylformamido)hexylphosphonic acid (0.05 g, 6.9%) as white solid.

$^1$H NMR (400 MHz, D₂O for major isomer): δ 8.26 and 7.85 (2×s, 1H, 1:7 rotamers, N—CHO), 4.20-4.18 (m, 1H), 3.80-3.59 (m, 2H), 3.53-3.47 (m, 1H), 3.29-3.25 (m, 1H), 1.97-1.90 (m, 1H), 1.76-1.55 (m, 1H), 1.49-1.43 (m, 2H).

$^{31}$P NMR (D₂O), δ 25.6 (P(O)(OH)₂). C$_6$H$_{16}$NO$_8$P.

ES-MS (m/z): 272.0 (M−H).

Example 12: [1,1-Difluoro-6-(formyl-hydroxy-amino)-(3R,4R,5S)-3,4,5-trihydroxy-hexyl]-phosphonic acid (monosodium salt)

Step 1: [1,1-Difluoro-2-(3R,4R,5R,6R)-(6-methoxy-2,2-dimethyl-tetrahydro-furo[3,4-d][1,3]dioxol-4-yl)-ethyl]-phosphonic acid diethyl ester (12a)

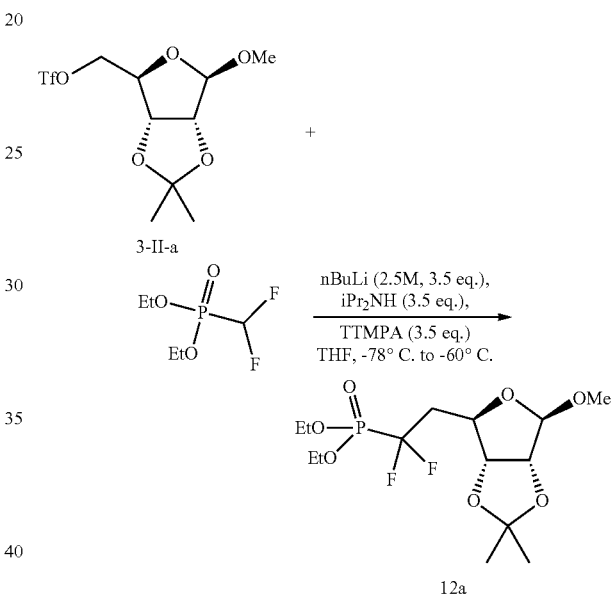

A stirred solution of diisopropylamine (3.2 g, 31.9 mmol) and tris(N,N-tetramethylene)phosphoric acid triamide (8.3 g, 31.9 mmol) in anhydrous THF (45 mL) under nitrogen atmosphere was cooled to −78° C. nBuLi (2.5M in hexane, 12.8 mL, 31.9 mmol) was added dropwise over 15 min via syringe pump and the reaction mixture was warmed to −5° C. in 25 min. The solution was cooled to −78° C. and a solution of diethyl(difluoromethyl)phosphonate (6.2 g, 31.9 mmol) in THF (25 mL) was added over 10 min via syringe pump. A white suspension appeared during the addition. After three minutes a solution of 3-II-a (3.6 g, 9.12 mmol) in THF (30 mL) was added to the suspension at −78° C. over 10 min via syringe pump and then the solution was warmed over 15 min at −60° C. The reaction mixture was quenched with NH₄Cl (100 mL) and the layers were separated. The aqueous layer was extracted three times with EtOAc (3×50 mL). The organic layers were combined, dried over Na₂SO₄, filtered and concentrated under reduced pressure. The residue was purified by chromatography (SiO₂ column 330 g, cyclohexane:EtOAc 75:25 to 60:40) to give the title compound 12a (765 mg, 1.73 mmol, 18% isolated yield) as a slightly yellow oil (assay=83%, estimated by $^1$H NMR).

$^1$H NMR (250 MHz, CDCl₃): δ 4.96 (s, 1H), 4.70-4.60 (m, 3H), 4.36-4.22 (m, 4H, 2×OCH₂CH₃), 3.34 (s, 3H, OC

H̱₃), 2.51-2.29 (m, 2H, CH̱₂—C₂), 1.48 (s, 3H, C—CH̱₃), 1.41-1.35 (m, 6H, 2×OCH̱₂CH₃), 1.31 (s, 3H, C—CH̱₃)

LC-MS ESI⁺: $C_{14}H_{26}F_2O_7P$ [M+H]⁺ calc. 375.1. found 374.9.

Step 2: [1,1-Difluoro-(2R)-2-(3R,4R)-(3,4,5-trihydroxy-tetrahydro-furan-2-yl)-ethyl]-phosphonic acid diethyl ester (12b)

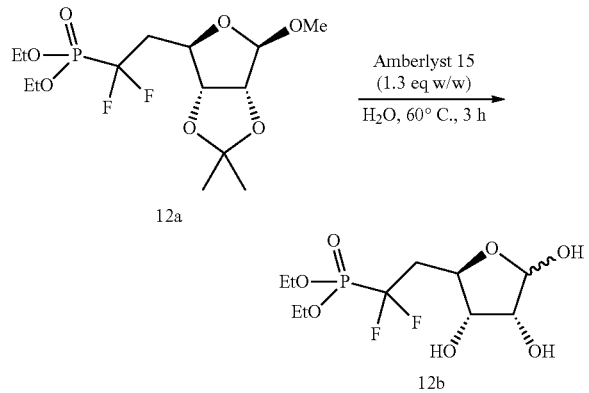

To a stirred solution of compound 12a (1.25 g, 2.67 mmol) in H₂O (6 mL) at 22° C. was added Amberlyst 15 (1.6 g, previously washed with H₂O, 1.3 eq. w/w). The resulting suspension was stirred at 60° C. for 3 hours until TLC (AcOEt:MeOH 95:5) and LC-MS (ESI⁺) indicated complete conversion. The reaction mixture was filtered and the resin was washed with H₂O. pH was adjusted to pH=6.5 by adding 5 mL of 0.1M NaOH aq. solution. The solution was concentrated to approximately 5 mL to give the title compound (2.67 mmol theoretical) in solution in H₂O which was used directly in the next step without further purification.

LC-MS APCI⁺: $C_{10}H_{20}F_2O_7P$ [M+H]⁺ calculated 321.1. found 321.2.

Step 3: (6-Benzyloxyimino-1,1-difluoro-(3R,4R, 5R)-3,4,5-trihydroxy-hexyl)-phosphonic acid diethyl ester (12c)

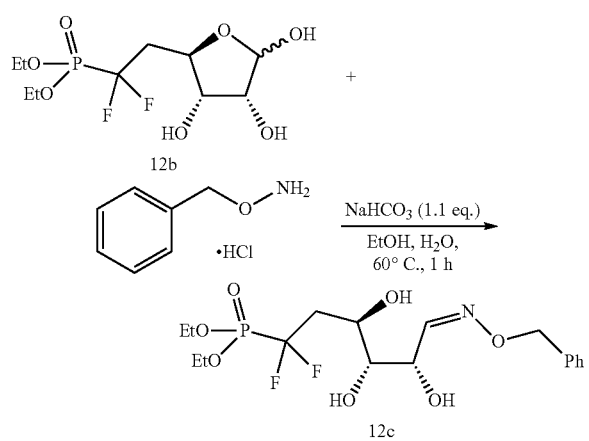

To a stirred solution of compound 12b (850 mg, 2.6 mmol) in H₂O (5 mL) obtained from previous step, was added EtOH (5 mL). Benzylhydroxylamine*HCl (545 mg, 3.38 mmol) and then NaHCO₃ (242 mg, 2.86 mmol) were added and the solution was heated to 60° C. and stirred for 1 h. The reaction mixture was concentrated under reduced pressure and the residue was purified by chromatography (SiO₂ column 40 g, CH₂Cl₂:EtOAc 60:40) to give the title compound 12c (853 mg, 1.90 mmol, 73% isolated yield over two steps) as a colorless oil (assay=95%, estimated by ¹H NMR). The compound was obtained as a mixture of oxime E and Z: 4:1.

¹H NMR (300 MHz, D₂O): δ 7.55 (d, 0.8H, J=7.0 Hz, H̱C=NOBn, E), 7.42-7.36 (m, 5H, Ph), 6.87 (d, 0.2H, J=6 Hz, H̱C=NOBn, Z), 5.11 (s, 2H, OCH̱₂Ph), 4.38-4.25 (m, 4.8H, 2×OCH̱₂CH₃+0.8H), 4.11-3.99 (m, 1.2H), 3.67 (br dd, 1H, J=5.0, 6.7 Hz), 2.63-2.11 (m, 2H, CH̱₂—CF₂), 1.34 (t, 6H, J=7.0 Hz, 2×OCH₂CH̱₃)

LC-MS APCI⁺: $C_{17}H_{27}F_2NO_7P$ [M+H]⁺ calculated 426.1. found 426.2.

Step 4: (6-Benzyloxyamino-1,1-difluoro-(3R,4R, 5S)-3,4,5-trihydroxy-hexyl)-phosphonic acid diethyl ester (12d)

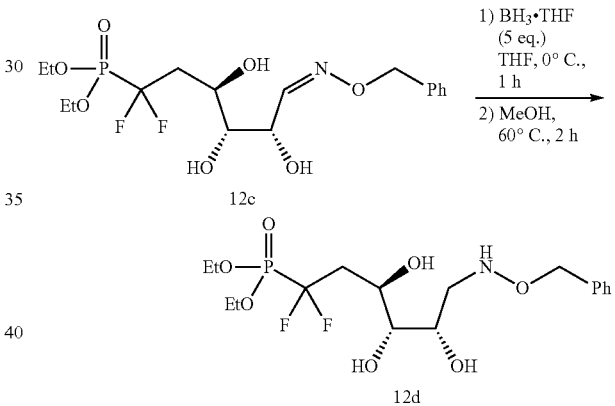

To a stirred solution of oxime 12c (830 mg, 1.86 mmol) in THF (8 mL) at 0° C. under nitrogen atmosphere was added dropwise BH₃·THF (1M, 9.3 mL, 9.3 mmol) via syringe pump over 10 min. The solution was stirred further at 0° C. for 1 hour until TLC (CH₂Cl₂:MeOH 90:10) and LC-MS indicated complete conversion. The reaction mixture was quenched carefully with MeOH (15 mL) at 0° C. and then heated at 60° C. for 2 hours. After cooling, the reaction mixture was concentrated under reduced pressure and the residue was purified by chromatography (SiO₂ column 15 g, EtOAc 100%) to give the title compound (626 mg, 1.32 mmol, 71% isolated yield) as a colorless oil (assay=90%, estimated by ¹H NMR).

¹H NMR (300 MHz, D₂O): δ 7.42-7.36 (m, 5H, Ph), 4.74 (s, 2H, OCH̱₂Ph), 4.38-4.26 (m, 4H, 2×OCH̱₂CH₃), 4.19-4.13 (m, 1H), 3.94-3.86 (m, 1H), 3.56 (t app., 1H, J=6.0 Hz), 3.23 (dd, 1H, J=2.5, 13.8 Hz), 2.84 (dd, 1H, J=9.2, 13.8 Hz), 2.57-2.10 (m, 2H, CH̱₂—CF₂), 1.34 (t, 6H, J=7.0 Hz, 2×OCH₂CH̱₃)

LC-MS APCI⁺: $C_{17}H_{29}F_2NO_2P$ [M+H]⁺ calculated 428.2. found 427.8.

Step 5: (6-Benzyloxyamino-1,1-difluoro-(3R,4R, 5S)-3,4,5-trihydroxy-hexyl)-phosphonic acid monoethyl ester sodium salt (12e)

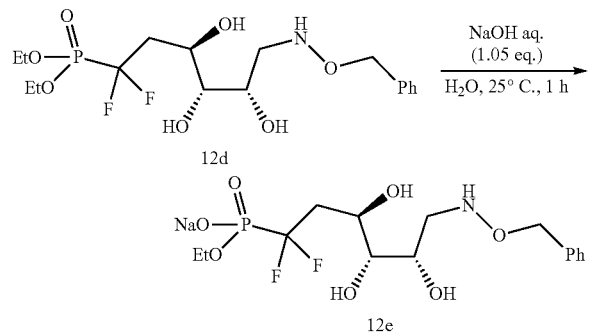

To a stirred solution of compound 12d (250 mg, 0.58 mmol) in $H_2O$ (3 mL) at 23° C., was added aqueous 0.2M NaOH solution (3 mL, 0.60 mmol). The solution was stirred for at 23° C. for 1 hour until LC-MS showed complete conversion. The reaction mixture was freeze and then lyophilised to give the title compound 12e (205 mg, 0.44 mmol, 84% isolated yield) as a white solid (assay=90%, estimated by $^1H$ NMR).

$^1H$ NMR (300 MHz, $D_2O$): δ 7.42-7.36 (m, 5H, Ph), 4.74 (br s, 2H, OC$\underline{H_2}$Ph), 4.37-4.13 (m, 1H), 4.07-3.73 (m, 3H, OC$\underline{H_2}$CH$_3$+H), 3.58-3.53 (m, 1H), 3.28-3.21 (m, 1H), 2.89-2.78 (m, 1H), 2.68-2.12 (m, 2H, C$\underline{H_2}$—CF$_2$), 1.24 (t, 3H, J=7.0 Hz, OCH$_2$C$\underline{H_3}$)

LC-MS APCI$^+$: $C_{15}H_{23}F_2NO_2P$ [M–H]$^-$ calc. 398.1. found 398.0.

Step 6: [6-(Benzyloxy-formyl-amino)-1,1-difluoro-(3R,4R,5S)-3,4,5-trihydroxy-hexyl]-phosphonic acid monoethyl ester sodium salt (12f)

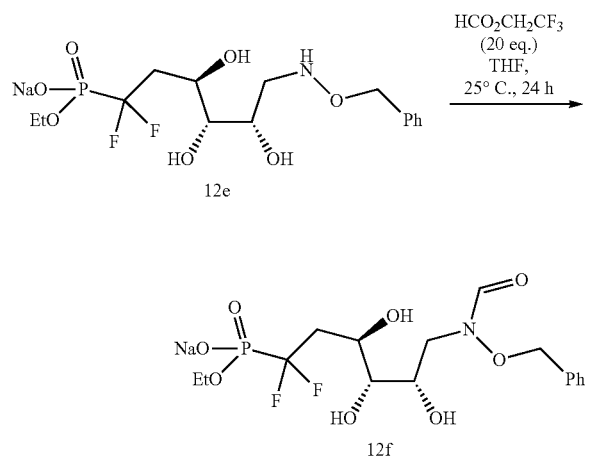

To a stirred solution of hydroxylamine 12e (200 mg, 0.45 mmol) in THF (3 mL) at 25° C. under nitrogen atmosphere was added trifluoroethyl formate (1.21 g, 9.0 mmol). The solution was stirred at 25° C. for 24 hours until LC-MS indicated complete conversion. The reaction mixture was concentrated under reduced pressure and the residue was purified by semi-preparative liquid chromatography (Column: Modulocart QS Strategy 10RP 21.2×250 mm, InterChim, gradient $H_2O$:$CH_3CN$ 95:5 to 50:50 over 20 min, flow rate 12 mL/min, fraction size 5 mL, Detector: MS-ESI$^-$) to give the title compound (63 mg, 0.13 mmol, 29% isolated yield) as a white solid (assay=90%, area % LC-MS and $^1H$ NMR).

$^1H$ NMR (250 MHz, $D_2O$): δ 8.11 (s, 0.3H, NC(=O)H, minor rotamer), 7.90 (s, 0.7H, NC(=O)H, major rotamer), 7.51-7.41 (m, 5H, Ph), 4.97 (s, 2H, OC$\underline{H_2}$Ph), 4.19-3.92 (m, 4H, OC$\underline{H_2}$CH$_3$+2H), 3.72-3.47 (m, 3H) 2.51-2.01 (m, 2H, C$\underline{H_2}$—CF$_2$), 1.24 (t, 3H, J=7.0 Hz, OCH$_2$C$\underline{H_3}$)

LC-MS ESI$^-$: $C_{26}H_{23}F_2NO_8P$ [M–Na]$^-$ calc. 426.1. found 425.9.

Step 7: [1,1-Difluoro-6-(formyl-hydroxy-amino)-(3R,4R,5S)-3,4,5-trihydroxy-hexyl]-phosphonic acid monoethyl ester sodium salt (12h)

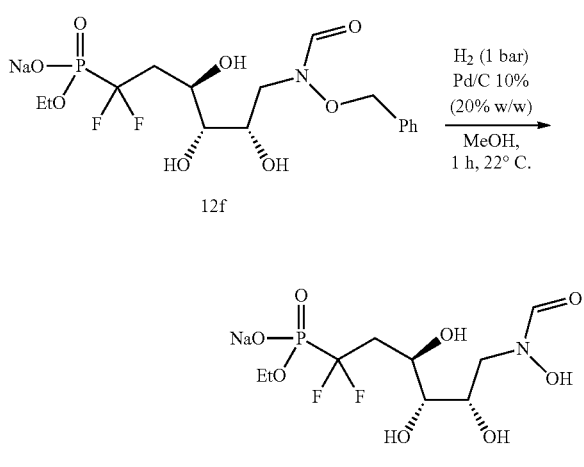

In an autoclave, compound 12f (60 mg, 0.13 mmol) was dissolved in MeOH (0.6 mL). Pd/C 10% Degussa type E101 (12 mg, 20% w/w) was added. The autoclave was purged three times with nitrogen (2 bar) and then three times with $H_2$ (2 bar). The pressure was set to 1 bar of $H_2$ and the reaction mixture was stirred at 22° C. for 1 hour. The autoclave was depressurized and purged with nitrogen. The reaction mixture was filtered over Celite® pad and the residue concentrated under reduced pressure to give the title compound (42 mg, 0.11 mmol, 85% isolated yield) as a white solid (assay=95%, estimated by $^1H$ NMR) which was used without further purification.

$^1H$ NMR (250 MHz, $D_2O$): δ 8.33 (s, 0.13H, NC(=O)H, minor rotamer), 7.88 (s, 0.8H, NC(=O)H, major rotamer), 4.24-4.18 (m, 1H), 4.10-3.98 (m, 3H, OC$\underline{H_2}$CH$_3$+1H), 3.76-3.58 (m, 3H), 2.52-2.03 (m, 2H, C$\underline{H_2}$—CF$_2$), 1.24 (t, 3H, J=7.0 Hz, OCH$_2$C$\underline{H_3}$)

LC-MS ESI$^-$: $C_9H_{17}F_2NO_8P$ [M–H]$^-$ calculated 336.1. found 336.0.

Step 8: [1,1-Difluoro-6-(formyl-hydroxy-amino)-(3R,4R,5S)-3,4,5-trihydroxy-hexyl]-phosphonic acid (monosodium salt) (Example 12)

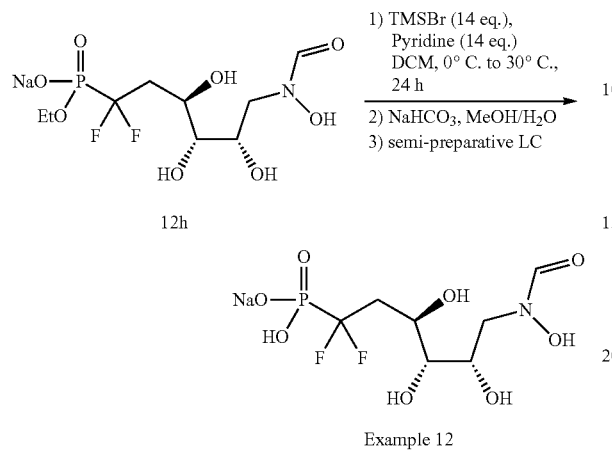

Example 12

To a stirred suspension of 12h (38 mg, 0.10 mmol) in anhydrous $CH_2Cl_2$ (2 mL) at 0° C. under nitrogen atmosphere was added Pyridine (65 μL, 0.80 mmol). TMSBr (109 μL, 0.8 mmol) was added dropwise over 5 min and the reaction mixture was stirred at 0° C. for 2 hours and then 17 hours at 22° C. At this time, starting material was still detected LC-MS (ESI⁻). At 22° C., Pyridine (49 μL, 0.60 mmol) and then TMSBr (82 μL, 0.60 mmol) were added. The reaction mixture was heated to 30° C. and stirred during 5 hours until LC-MS indicated complete conversion. The reaction mixture was concentrated under reduced pressure at 0° C. Water (2 mL) and MeOH (2 mL) were added to the residue at 0° C. and the mixture was neutralized with an aqueous solution of $NaHCO_3$ up to pH=7.5. The solution was stirred at 20° C. until complete desilylation as determined by LC-MS (ESI⁻). The reaction mixture was then lyophilized. The resulting powder was dissolved in $H_2O$ (500 μL) and pH was adjusted to pH=4.5 by adding AcOH in the mixture. The compound was then purified by semi-preparative liquid chromatography (Column: Modulocart QS Strategy 10RP 21.2×250 mm, InterChim, gradient $H_2O$:$CH_3CN$ 3:97 to 40:60 over 15 min, flow rate 12 mL/min, fraction size 5 mL, Detector: MS-ESI⁻) to give the title compound (22 mg, 0.06 mmol, 66% isolated yield) as a yellow solid (assay=95%, estimated by $^1H$ NMR; Area %=91%, TIC Mode in LC-MS).

$^1H$ NMR (250 MHz, $D_2O$): δ 8.31 (s, 0.12H, NC(=O)H, minor rotamer), 7.85 (s, 0.71H, NC(=O)H, major rotamer), 4.1 (br dd, 1H, J=6.8, 8.2 Hz), 4.06-3.97 (m, 1H), 3.76-3.56 (m, 3H), 2.47-2.01 (m, 2H, C$\underline{H}_2$—CF$_2$)

$^{31}P$ NMR (101 MHz, $D_2O$): δ 5.4 (t app., $J_{31P-19F}$=86 Hz)

$^{19}F$ NMR (235 MHz, $D_2O$): δ −108.0 (dd, $J_{31P-19F}$=86 Hz and $J_{19F-19F}$=282 Hz, 1F), −110.2 (dd, $J_{31P-19F}$=86 Hz and $J_{19F-19F}$=282 Hz, 1F)

LC-MS ESI⁻: $C_7H_{13}F_2NO_8P$ [M−H]⁻ calculated 308.0. found 307.9.

Example 13: Sodium [1-(N-hydroxy-N-formylamino)-1,6-dideoxy-D-allo/L-talo-hexitol)] 6-phosphonate

Step 1: Dibenzyl [2,3,4-tri-O-benzyl-1-(N-benzyloxy-N-formylamino)-1,6-dideoxy-D-allo/L-talo-hexitol)] 6-phosphonate (13a)

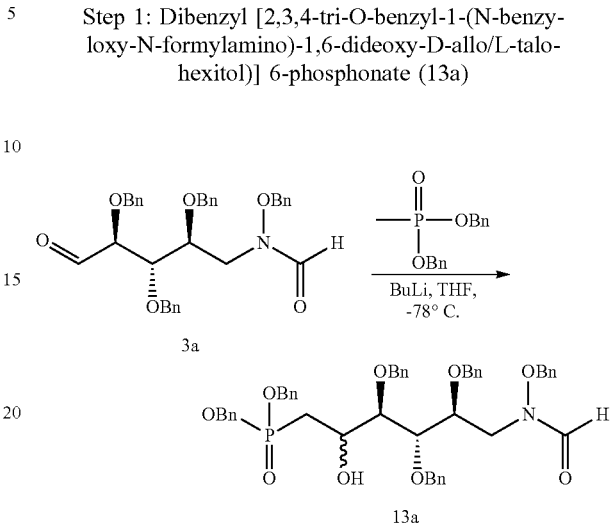

13a

Dibenzyl methanephosphonate (134 mg, 0.48 mmol, obtained as described in Tet. Lett. 1999, 40, 1869-1872) was dissolved in THF (1.5 mL) and cooled to −78° C. Then a 2 M solution of BuLi in hexane (190 μL) was added dropwise and the reaction was stirred at the same temperature for 30 min. Subsequently aldehyde 3a (180 mg, 0.32 mmol, obtained as described in Example 3, synthesis method 1, step 1) was added dropwise and the reaction was stirred at −78° C. Progress of the reaction was monitored by TLC (EtOAc/Hex, 1:2) every 30 min and was quenched after 90 min by adding aq. $NH_4Cl$. The suspension was extracted into EtOAc and washed with brine. The organic phase was dried, concentrated and the residue was purified by column chromatography EtOAc/Hex 1:2 to yield 50 mg (28%) of recovered aldehyde 3a, 55 mg (22%) of the deformylated product 13a' and 25 mg (10%) of 13a as syrup; Data for 13a:

$[\alpha]_D^{20}$+8.6 (c 0.45, $CHCl_3$); $^1H$ NMR-Data (toluene-$d_8$, 90°): δ 8.06 (s, 1H, H-formyl), 7.30-6.94 (m, 30H, H—Ar), 4.95-4.44 (13H, 6×CH$_2$—Ar, H-2), 4.20 (bt, 1H, H-5), 3.93 (bt, 1H, H-4), 3.83 (bt, 1H, H-3), 3.77 (m, 2H, H-6a, H-6b), 2.21 (ddd, 1H, J=15.0 and 2.5 Hz, H-1a), 2.12 (ddd, 1H, H-1b). $^{13}C$ NMR: δ 161.0 (C-formyl), 137.4-124.6 (36C—Ar), 82.5 (d, C—P coupling, J=14 Hz, C-4), 79.8 (C-3), 76.8 (C-2), 76.7 (CH$_2$—Ar), 74.2, 73.5, 72.7 (3×CH$_2$—Ar), 67.5 (d, C—P coupling, J=6 Hz, C-5), 67.0, 67.0 (2×CH$_2$—Ar), 48.3 (C-1), 29.8 (d, C—P coupling J=138 Hz, C-6). $^{31}P$ NMR: δ 25.2 (s). LC-MS data expected mass: 829.33. found 830.4 as M⁺+H.

$^1H$ NMR-Data for 13a' (toluene-$d_8$ 90°, major isomer): δ 7.27-6.95 (m, 30H, H—Ar), 4.92-4.80 (m, 4H, 2×CH$_2$—Ar), 4.68-4.48 (m, 9H, 4×CH$_2$—Ar, H-5), 4.13 (ddd, 1H, H-2), 3.94 (dd, 1H, J=4.6 Hz, H-3), 3.82 (dd, 1H, J=4.9 Hz, H-4), 3.36 (dd, 1H, J=4 Hz, J=14 Hz, H-1a), 3.21 (dd, 1H, J=7 Hz, H-1b), 2.26 (ddd, 1H, J=3, J=15 Hz, H-6a), 2.14 (ddd, 1H, J=7 Hz, H-6b). $^{13}C$ NMR: δ 137.4-124.4 (36C—Ar), 82.4 (d, C—P coupling, J=15 Hz, C-4), 80.2 (C-3), 77.1 (C-2), 75.7, 74.0, 73.5, 72.4 (4×CH$_2$—Ar), 67.6 (d, C—P coupling, J=5 Hz, C-5), 67.0, 66.9 (2×CH$_2$—Ar), 52.8 (C-1), 29.9 (d, C—P coupling J=140 Hz, C-6). $^{31}P$ NMR (242 MHz): δ 32.5 (s). LC-MS data: expected mass 801.34. found 802.4 as M⁺+H. To transform side product 13a' into title compound 13a, carbonyldiimidazole (CDI, 62 mg, 0.38 mmol) was dissolved in THF (1 mL) and cooled to 0° C. Then formic acid (15 µL, 0.38 mmol) was added and the mixture was stirred at 0° C. for 30 min under protected atmosphere. Meanwhile a solution of 13a' (60 mg, 0.075 mmol) in THF (0.5 mL) was prepared. The solution of CDI and formic acid was then added and the mixture was stirred at RT for 36 h (TLC: EtOAc/hexane 1:7). After completeness of the reaction, all volatiles were evaporated, co-evaporated with toluene and the residual material was purified by column chromatography to yield 45 mg (73%) of 13a.

Step 2: Sodium [1-(N-hydroxy-N-formylamino)-1, 6-dideoxy-D-allo/L-talo-hexitol)] 6-phosphonate (Example 13)

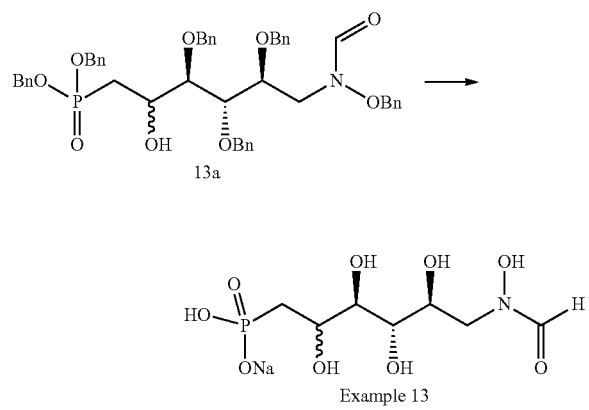

13a

Example 13

Compound 13a (20 mg, 0.024 mmol) was dissolved in 1:2 THF/water and 20% Pd(OH)$_2$—C catalyst (4 mg) was added. The reaction was stirred overnight (18 h) under hydrogen atmosphere (1 bar) and checked by TLC (Chloroform/Methanol/Water 10:10:3). The catalyst was then filtered off and the filtrate was washed with 1:1 water/methanol mixture (1:1) and purified by HILIC separation (column: Sequant ZIC HILIC 10×250 mm, Merck, Gradient MeCN/H$_2$O 85 to 40%, flow rate 3 mL, fraction size 2 mL). Purity of fractions was checked by $^1$H NMR and product containing fractions were pooled and lyophilized to give title compound (0.65 mg, 10%) as white solid; [α]$_D^{20}$+17.4 (c 0.2, water); $^1$H NMR (D$_2$O, 600 MHz, ratio of rotamers 4.1:1): δ 8.31 (s, CHO, minor form), 7.86 (s, 1H, CHO major isomer), 4.27 (ddd, 1H, J=8.7, J=4.7 Hz, H-2), 4.19 (dt, 1H, J=3.6 (2×), J=9.8 Hz H-5), 3.80 (dd, 1H, J=8.3, J=4.0 Hz, H-3), 3.76 (dd, 1H, J=8.2, J=4.4 Hz, H-4), 3.72-3.70 (m, 2H, H-1a, H-1b), 1.11 (ddd, 1H, J=3.5, J=14.6 Hz, H6a), 1.65 (ddd, 1H, J=9.3, J=14.9 Hz, H-6b). $^{31}$P NMR (D$_2$O): δ 29.4. $^{13}$C NMR (D$_2$O, 125 MHz): δ 75.13 (d, J=9.3 Hz, C-4), 73.62 (C-3), 69.82 (C-5), 68.53 (C-2), 54.06 (C-1), 30.79 (d, J=104.1 Hz, C-6). Mass Data: LC-MS (HILIC) calculated for: C$_7$H$_{16}$NO$_9$P (289.0563) m/z: 290.0 (M+H)$^+$, 287.9 (M−H)$^−$.

Example 14: Sodium 1-(N-benzyloxy-N-formylamino)-1-deoxy-D-ribo-5-(E)-hexenitol 6-phosphonate

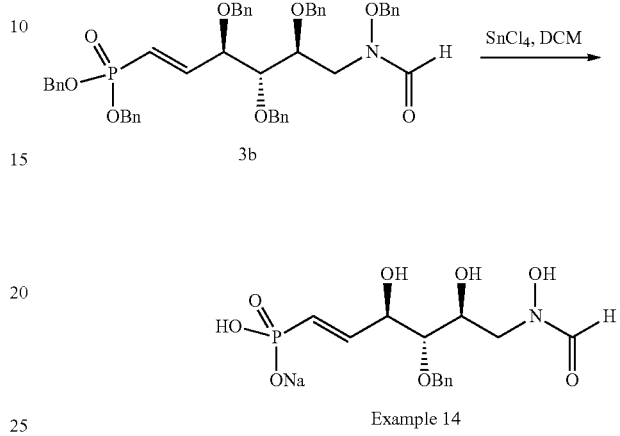

3b

Example 14

Compound 3b (20 mg, 0.025 mmol) was dissolved in dry DCM (0.5 mL) and a 1 M solution of SnCl$_4$ in DCM (0.17 mmol) was added dropwise. The reaction was stirred at RT overnight. After this time another aliquot (0.1 mmol) of the reagent was added and stirred for another 3 h. Then the mixture was poured onto calculated amount of sodium bicarbonate dissolved in water (2 mL) and stirred for 10 min. Then DCM was evaporated and the residue containing insoluble tin(IV) salts was filtered through cotton and micro filter (2×). The filtrate was concentrated and purified by ZIC-HILIC chromatography (column: Sequant ZIC HILIC 10×250 mm, Merck, Gradient MeCN/H$_2$O 85 to 40%, flow rate 3 mL, fraction size 2 mL). Purity of fractions was checked by $^1$H NMR and product containing fractions were pooled and lyophilized to give title compound (3.56 mg, 54%) as white solid. To remove residual sodium bicarbonate, the material was passed over DOWEX-50 (H+) and the pH of the filtrate was adjusted to 7.0 by addition of 0.01 M NaOH. [α]$_D^{20}$+4.1 (c 0.4, D$_2$O); $^1$H NMR (D$_2$O 600 MHz, ratio of rotamers 7.5:1): δ 8.28 (s, CH=O, minor rotamer), 7.82 (s, 1H, CH=O, major rotamer), 6.25 (dt, 1H, J=6.5, J=17.4 Hz, H-5), 6.08 (dt, 1H, J=16.1 Hz H-6), 4.37 (bt, 1H, J=6.1 Hz, H-4), 4.07 (ddd, 1H, J=2.6 Hz, J=6.7 Hz, J=8.3 Hz, H-2), 3.74-3.70 (m, 2H, H-3, H-1a), 3.64 (ddd, 1H, J=13.6, J=7.3 Hz, H-1b). $^{13}$C NMR (D$_2$O, 125 MHz): δ 156.07 (C=O), 137.09 (C-5), 131.68 (d, J=167.0 Hz, C-6), 75.09 (C-3), 72.99 (d, J=17.0 Hz, C-4), 67.46 (C-2), 54.34 (C-1). $^{31}$P NMR (242 MHz, D$_2$O): δ 9.62 (s). LC-MS (HILIC) m/z: calculated for: C$_2$H$_{24}$NO$_8$P (271.0457). found 271.9. (M+H)$^+$, 543.1 (2M+H)$^+$, 269.8 (M−H)$^−$, 541.0 (2M−H)$^−$.

Example 15: ((3S,5R)-3,5-dihydroxy-6-(N-hydroxy-formamido)-hexyl)phosphonic acid

Step 1: Dithiocarbonic acid O-[(5R,6S,6aR)-5-(2,2-dimethyl-[1,3]dioxolan-4-yl)-2,2-dimethyl-tetrahydro-furo[2,3-d][1,3]dioxol-6-yl] ester S-methyl ester (15a)

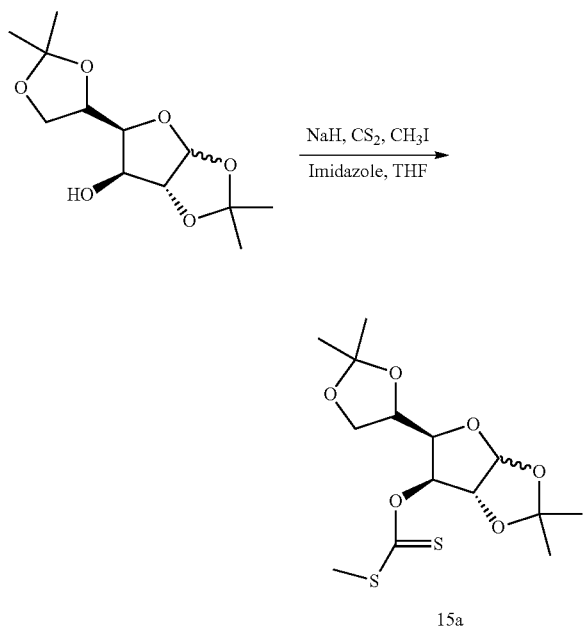

To a solution of 1,2:5,6-Di-O-isopropylidene-α-D-glucofuranose (30.0 g, 115.25 mmol) in dry THF imidazole (0.078 g, 1.15 mmol, 0.01 equiv.) was added followed by NaH (6.92 g, 173.0 mmol, 1.5 equiv.) added portion wise at 0° C. and the mixture was stirred at the same temperature for 20 min. To the mixture was added carbon disulfide (17.5 g, 230.76 mmol, 2.0 eq.) at 0° C., then, after stirring the reaction mixture for 30 min at 0° C., iodomethane (19.33 g, 136.14 mmol, 1.18 equiv.) was added at 0° C. Reaction was allowed to warm to room temperature with stirring and monitored by TLC (10% EtOAc:Hexane with 10% $H_2SO_4$:EtOH staining). After completion of reaction, reaction mass was quenched by acetic acid (15 mL), diluted with ethyl acetate, washed with water and separated aqueous phase was discarded. Organic phase was neutralized with saturated $NaHCO_3$ aqueous solution, washed with brine. Combined separated organic layers were dried over $Na_2SO_4$, filtered and concentrated under reduced pressure to afford title compound 15a (40.0 g, crude) as yellow oil, which was used in next step without further purification.

$^1$H NMR (400 MHz, $CDCl_3$): δ 5.91-5.90 (t, 2H, J=4.0 Hz), 4.67-4.66 (d, 1H, J=3.6 Hz), 4.34-4.27 (m, 2H), 4.14-4.03 (m, 2H), 2.58 (s, 3H), 1.56 (s, 3H), 1.41 (s, 3H), 1.32 (s, 3H), 1.31 (s, 3H).

Step 2: (5S,6aR)-5-(2,2-Dimethyl-[1,3]dioxolan-4-yl)-2,2-dimethyl-tetrahydro-furo[2,3-d][1,3]dioxole

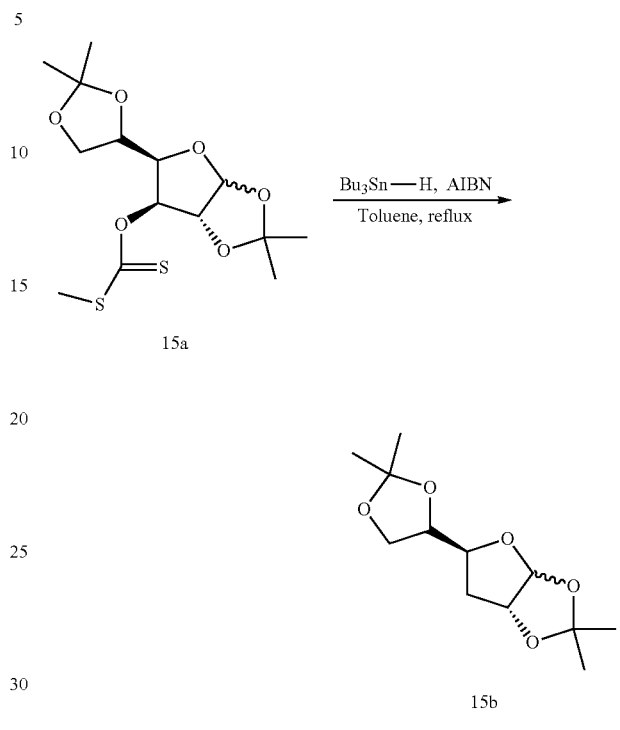

To a solution of compound 15a (40.0 g, 114.28 mmol) and AIBN (0.187 g, 1.142 mmol, 0.01 eq.) in dry toluene under argon was added tributyltin hydride (66.51 g, 228.57 mmol, 2.0 eq.) under inert atmosphere. Reaction mixture was heated at 115° C. for 2 h (progress was monitored by TLC: 20% EtOAc:Hexane with 10% $H_2SO_4$:EtOH staining) and. concentrated under reduced pressure. The residue was purified using column chromatography on 100-200 mesh silica gel EtOAc:n-hexane gradient as eluent to afford the title product 15b (21.20 g, 76.0%) as colorless oil.

$^1$H NMR (400 MHz, $CDCl_3$): δ 5.81-5.80 (d, 1H, J=3.6 Hz), 4.76-4.73 (t, 1H, J=4.4 Hz), 4.18-4.05 (m, 3H), 3.85-3.78 (m, 1H), 2.20-2.15 (m, 1H), 1.50 (s, 3H), 1.42 (s, 3H), 1.35 (s, 3H), 1.31 (s, 3H).

Step 3: 1-((5S,6aR)-2,2-Dimethyl-tetrahydro-furo[2,3-d][1,3]dioxol-5-yl)-ethane-1,2-diol

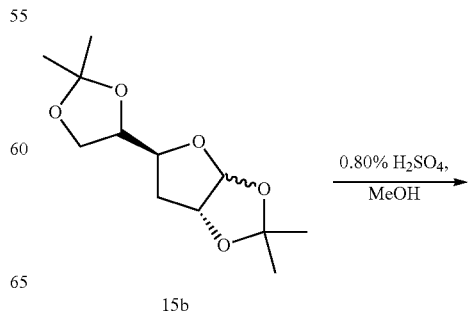

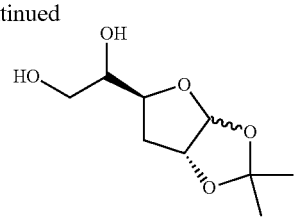

15c

To a solution of 15b (21.0 g, 86.06 mmol) in methanol (252 mL) was added 0.8% aqueous solution of H$_2$SO$_4$ (111.3 mL) at 0° C. and reaction mixture was stirred at room temperature for 3 h. Reaction progress was monitored by TLC (80% EtOAc:Hexane with 10% H$_2$SO$_4$:EtOH staining). After completion of the reaction, the mixture was neutralized by BaCO$_3$ powder and filtered through celite bed. Filtrate was concentrated under reduced pressure to afford yellowish oil, which was then purified by flash chromatography on silica gel (eluents: hexane/ethyl acetate) to afford compound 15c (10.61 g, 60.45%) as colorless oil.

$^1$H NMR (400 MHz, CDCl$_3$): δ 5.80-5.79 (d, 1H, J=3.6 Hz), 4.76-4.74 (t, 1H, J=4.4 Hz), 4.25-4.20 (m, 1H), 3.95-3.91 (m, 1H), 3.74-3.69 (m, 1H), 3.62-3.50 (m, 1H), 2.42-2.41 (d, 1H, J=4.0 Hz), 2.09-2.03 (m, 2H), 1.88-1.81 (m, 1H), 1.51 (s, 3H), 1.32 (s, 3H).

Step 4: (5S,6aR)-2,2-Dimethyl-tetrahydro-furo[2,3-d][1,3]dioxole-5-carbaldehyde (15d)

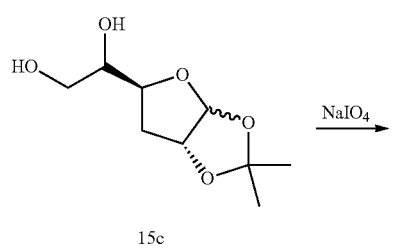

To a solution of compound 15c (10.6 g, 51.96 mmol) in methanol (150 mL) was added portion wise at 0° C. sodium meta periodate (13.34 g, 62.35 mmol, 1.2 equiv.). After addition reaction mixture was allowed to be stirred at RT for 3 h. Reaction progress was monitored by TLC (80% EtOAc: Hexane with 10% H$_2$SO$_4$:EtOH and 2,4-DNP staining). After completion the reaction, the mixture was filtered through celite pad and filtrate was concentrated under reduced pressure to afford compound 15d (9.6 g, crude) as colorless oil. The crude compound was used as such in next step without further purification.

$^1$H NMR (400 MHz, CDCl$_3$): δ 9.68 (s, 1H), 5.84-5.81 (m, 1H), 4.79-4.58 (m, 1H), 4.33-4.25 (m, 1H), 2.13-2.05 (m, 1H), 1.92-1.75 (m, 1H), 1.51 (s, 3H), 1.31 (s, 3H).

Step 5: [(E)-2-((5S,6aR)-2,2-Dimethyl-tetrahydro-furo[2,3-d][1,3]dioxol-5-yl)-vinyl]-phosphonic acid dimethyl ester (15e)

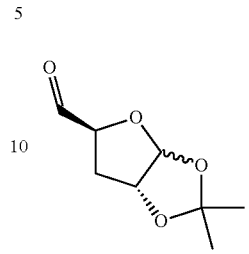

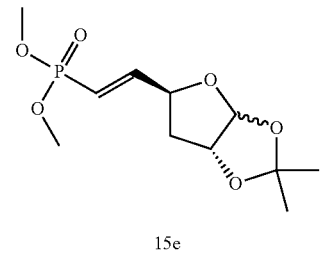

To a solution of tetramethyl-methylenediphosphonate (10.52 g, 45.32 mmol, 1.3 eq.) in diethyl ether (60 mL) was added NaH (60% in mineral oil) (1.67 g, 41.86 mmol, 1.2 eq.) portion wise at 0° C., and the mixture was stirred at 0° C. for 45 min.

To this mixture compound 15d (6.0 g, 34.88 mmol) dissolved in diethyl ether (40 mL) was added drop wise at 0° C. After addition the reaction mixture was allowed to warm to room temperature and stirred for 20 min. (the completion of the reaction was monitored by TLC: 80% EtOAc:hexane with 10% H$_2$SO$_4$:EtOH staining), it was diluted with ethyl acetate and washed with water and brine. Combined organic phases were dried over Na$_2$SO$_4$, concentrated under reduced pressure to afford yellow oil, which was then purified by chromatography on 100-200 mesh silica gel (eluents: hexane and EtOAc gradient) to afford the title compound 15e (5.84 g, 60.26%) as colorless oil.

$^1$H NMR (400 MHz, CDCl$_3$): δ 6.86-6.75 (m, 1H), 6.64-5.92 (m, 1H), 5.86-5.85 (m, 1H), 4.79-4.75 (m, 2H), 3.73 (s, 3H), 3.70 (s, 3H), 2.30-2.25 (m, 1H), 1.64-1.56 (m, 1H), 1.51 (s, 3H), 1.32 (s, 3H).

Step 6: [2-((5S,6aR)-2,2-Dimethyl-tetrahydro-furo[2,3-d][1,3]dioxol-5-yl)-ethyl]-phosphonic acid dimethyl ester (15f)

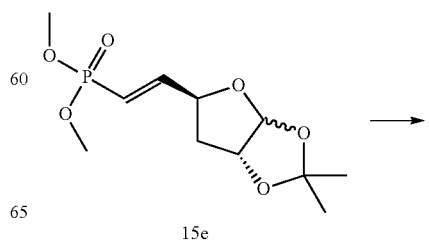

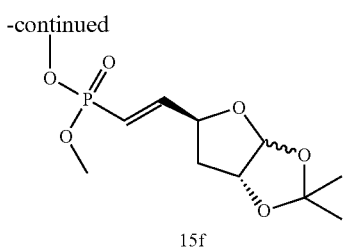

15f

To a solution of 15e (6.5 g, 23.38 mmol) in methanol was added 10% Pd/C (1.95 g, 50% moisture) and reaction mixture was stirred under hydrogen atmosphere (1 atm) for 3 h. Reaction progress was monitored by TLC (100% EtOAc with 10% $H_2SO_4$:EtOH stain). After completion of the reaction, the mixture was filtered through celite bed and filtrate was concentrated under reduced pressure to afford compound 15f (5.6 g, crude) as yellowish oil. The crude compound was used as such in next step without further purification.

$^1$H NMR (400 MHz, CDCl$_3$) δ 5.78-5.77 (d, 1H, J=3.6 Hz), 4.71-4.69 (m, 1H), 4.21-4.16 (m, 1H), 3.73 (s, 3H), 3.70 (s, 3H), 2.12-2.06 (m, 1H), 1.93-1.71 (m, 5H), 1.45 (s, 3H), 1.29 (s, 3H).

Step 7: [2-((2S,4R)-4,5-Dihydroxy-tetrahydro-furan-2-yl)-ethyl]-phosphonic acid dimethyl ester (15g)

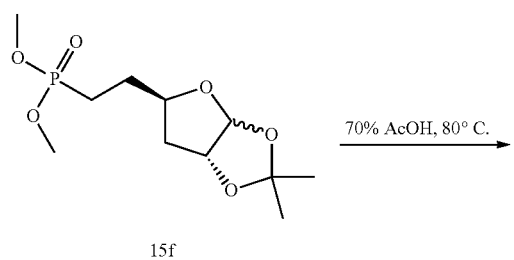

15f

A solution of the compound 15f (5.5 g, 19.64 mmol) in 70% acetic acid (247 mL, 45 mL/g) was heated up to 80° C. for 26 h. Reaction progress was monitored by ELSD and TLC (10% MeOH:DCM with 10% $H_2SO_4$:EtOH staining). Reaction mixture was concentrated under reduced pressure and obtained residue was purified by flash chromatography on silica gel (eluents: DCM/MeOH gradient) to afford title compound 15g (1.92 g, 40.80%) as colorless oil.

$^1$H NMR (400 MHz, MeOD): δ 5.11 (s, 1H), 4.61 (s, 1H), 4.31-4.24 (m, 1H), 4.08-4.07 (m, 1H), 3.75 (s, 3H), 3.73 (s, 3H), 3.34 (s, 1H), 2.05-1.74 (m, 6H).

Step 8: ((3S,5R)-6-Benzyloxyimino-3,5-dihydroxy-hexyl)-phosphonic acid dimethyl ester (15i)

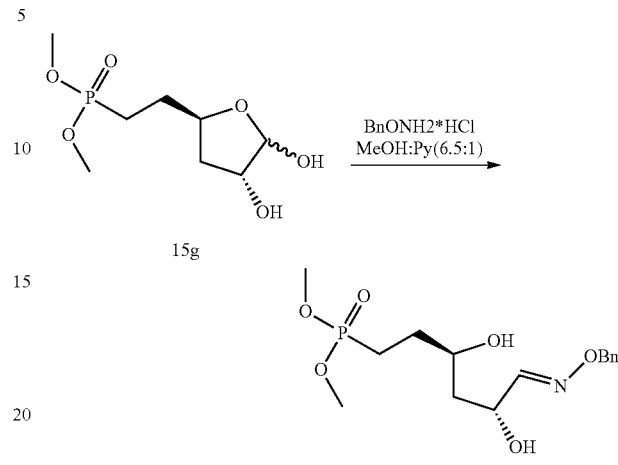

A solution of compound 15g (1.90 g, 7.916 mmol) and O-benzylhydroxylamine hydrochloride (1.89 g, 11.87 mmol, 1.50 eq.) in the mixture methanol:pyridine (6.5:1) was heated up to 65° C. for 6 h (reaction monitored by TLC: 10% MeOH:DCM with 10% $H_2SO_4$:EtOH stain). Reaction mixture was concentrated under reduced pressure, and obtained residue was purified by flash chromatography on silica gel (eluents: DCM/MeOH gradient) to afford title compound 15h (1.82 g, 66.60%) as colorless oil.

$^1$H NMR (400 MHz, DMSO) δ 7.37-7.29 (m, 5H), 5.28-5.24 (m, 1H), 5.03-5.00 (m, 2H), 4.63-4.58 (m, 1H), 4.21-4.18 (m, 1H), 3.60 (s, 3H), 3.57 (s, 3H), 3.48-3.47 (br, 1H), 1.88-1.74 (m, 1H), 1.72-1.57 (m, 4H), 1.53-1.44 (m, 1H).

Step 9: ((3S,5R)-6-Benzyloxyamino-3,5-dihydroxy-hexyl)-phosphonic acid dimethyl ester (15i)

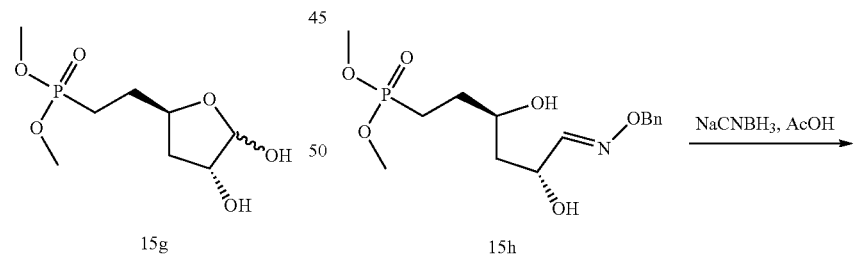

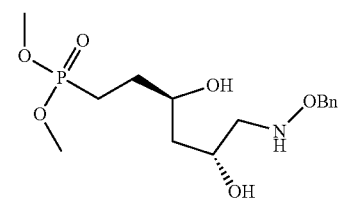

15i

To a solution of the compound 15h (1.80 g, 5.21 mmol) in acetic acid (20 mL) sodium cyanoborohydride (1.29 g, 20.86 mmol, 4.0 equiv.) was added at 0° C. and reaction mixture was stirred at room temperature for 1 h. Then reaction mass diluted with DCM and washed with water. Combined separated organic phases were neutralized with saturated aqueous solution of sodium bicarbonate and washed with brine, then dried over sodium sulfate, filtered and concentrated under reduced pressure. Obtained crude residue was purified by flash chromatography on silica gel (eluents: DCM/MeOH gradient) to afford title compound 15i (1.62 g, 88.39%) as colorless oil.

$^1$H NMR (400 MHz, DMSO) δ 7.40-7.28 (m, 5H), 6.47 (br, 1H), 4.62-4.60 (m, 4H), 3.75 (br, 1H), 3.61 (s, 3H), 3.59 (s, 3H), 2.81 (br, 1H), 2.70-2.67 (m, 1H), 1.90-1.59 (m, 3H), 1.46-1.41 (m, 3H).

Step 10: [(3S,5R)-6-(Benzyloxy-formyl-amino)-3,5-dihydroxy-hexyl]-phosphonic acid dimethyl ester (15j)

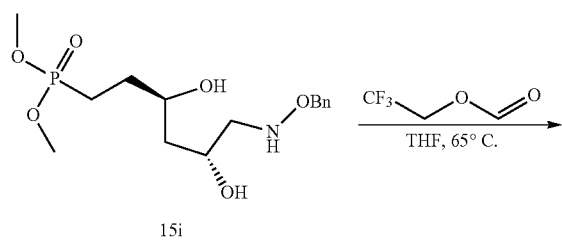

A solution of compound 15i (1.5 g, 4.32 mmol) and 2,2,2-trifluoroethylformate (5.53 g, 43.22 mmol, 10.0 equiv.) in THF (15 mL) was heated to 65° C. for 26 h with stirring (monitoring by LCMS). Then reaction mixture was concentrated under reduced pressure and crude residue was purified by flash chromatography on silica gel (eluents: DCM/MeOH gradient) to afford title compound 15j (0.820 g, 50.61%) as colorless oil.

$^1$H NMR (400 MHz, DMSO): δ 8.23 and 7.89 (2*s, 1H, 1:1.3 rotamers, CHO), 7.42-7.39 (m, 5H), 5.75 (s, 1H), 4.91 (m, 3H), 4.68-4.67 (br s, 1H), 3.81 (m, 1H), 3.61 (s, 3H), 3.58 (s, 3H), 3.39 (br s, 1H), 1.90-1.79 (m, 1H), 1.77-1.61 (m, 2H), 1.45-1.23 (m, 3H).

Step 11: [(3S,5R)-6-(Formyl-hydroxy-amino)-3,5-dihydroxy-hexyl]-phosphonic acid dimethyl ester (15k)

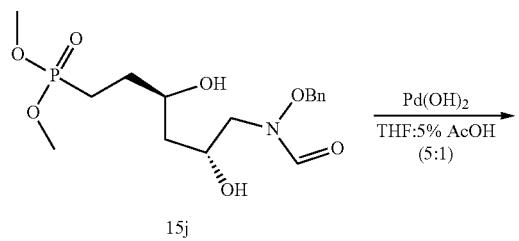

To a solution of the compound 15j (0.200 g, 0.533 mmol) in THF:5% AcOH (mixture 5:1, 6 mL) was added Pd(OH)$_2$ (0.050 g, 20% w/w, 50% moisture) and reaction mixture was stirred under hydrogen atmosphere (1 atm) for 1 h at room temperature (monitored by MS and TLC: 20% MeOH:DCM with 10% H$_2$SO$_4$:EtOH stain). Then the mixture was filtered through celite bed and filtrate was concentrated under reduced pressure to afford crude title compound 15k (0.146 g, crude) as brown oil, which was used as such in next step without further purification.

$^1$H NMR (400 MHz, DMSO) δ 9.48 and 9.48 (2*s, 1H, 1:2 rotamers, N—OH), 8.26 and 7.81 (2*s, 1H, 1:2 rotamers, CHO), 4.80-4.64 (m, 2H), 3.82-3.72 (br s, 1H), 3.62 (s, 3H), 3.59 (s, 3H), 3.24 (s, 1H), 1.87-1.79 (m, 3H), 1.73-1.55 (m, 3H).

Step 12: ((3S,5R)-3,5-dihydroxy-6-(N-hydroxyformamido)-hexyl)phosphonic acid (15l, Example 15)

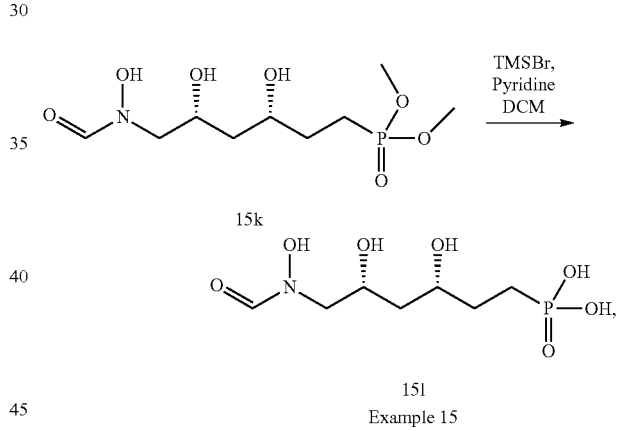

To a solution of bromotrimethylsilane (0.579 g, 3.78 mmol, 6.0 equiv.) in DCM (5 mL) under inert atmosphere pyridine (0.298 g, 3.78 mmol, 6.0 equiv.) was added at 0° C. After that a solution of compound 15k (0.180 g, 0.631 mmol) in DCM (3 mL) was added dropwise to above solution at 0° C. and obtained reaction mixture was stirred for 1.5 h at 0° C. (progress was monitored by MS). After completion of reaction, the mixture was concentrated under reduced pressure at 30° C. to dryness and the crude residue was purified by prep-HPLC (sample dilution in acetinitrile/H$_2$O mixture, column—ZIC HILIC 21.2*250 mm, 5 μm; Mobile Phase: A-ACN, B— 5 mM Ammonium Acetate aq. solution, flow rate—15 mL/min, ELSD detection) to afford title compound 15l, Example 15 (0.020 g, yield 12.34%).

$^1$H NMR (400 MHz, D$_2$O): δ 8.34 and 7.91 (2*s, 1H, 1:6 rotamers, CHO), 4.2-4.12 (br s, 1H), 3.96-3.94 (br s, 1H), 3.68-3.56 (m, 2H), 1.74-1.53 (m, 6H).

$^{31}$P NMR (D$_2$O): δ 25.61 (P(O)(OH)$_2$).

ES-MS (m/z): 256.0 (M−H).

Examples of Pharmaceutical Compositions

Solutions for IV administration have been prepared by diluting the compound of example 2 at 1-20 mg/mL in physiological serum (0.9% sodium chloride in non-pyrogenic water) or in glucose solution (1-5% glucose in non-pyrogenic water), with and without addition of erythromycin (1-5 mg/mL).

Other solutions for IV administration have been prepared by diluting 500 mg of compound of example 2 in 100 mL of physiological serum (0.9% sodium chloride in non-pyrogenic water) or of glucose solution (5% glucose in non-pyrogenic water).

Pharmacological Study of the Compounds of the Invention
Inhibition of the Enzymatic Activity of GmhA (Luminescent Assay):

The assay buffer "AB" contained 50 mM Hepes pH7.5, 1 mM $MnCl_2$, 25 mM KCl, 0.012% Triton-X100, 1 mM dithiothreitol (DTT) and 0.1 µM Myelin basic protein (MBP). The following components were added in a white polystyrene Costar plate up to a final volume of 30 µL: 10 µL inhibitor dissolved in DMSO/water 50/50, and 20 µL GmhA of E. coli in AB. After 30 min of pre-incubation at room temperature, 30 µL of Substrates mix in AB were added in each well to a final volume of 60 µL. This reaction mixture was then composed of 2 nM GmhA, 3 µM sedoheptulose-7-phosphate (Sigma), 3 µM ATP (Sigma) and 50 nM HldE of E. coli in assay buffer. After 30 minutes of incubation at room temperature, 100 µL of the revelation mix were added to a final volume of 160 µL, including the following constituents at the respective final concentrations: 10000 light units/mL luciferase (Sigma), 20 µM D-luciferin (Sigma), 100 µM N-acetylcysteamine (Aldrich). Luminescence intensity was immediately measured on Luminoskan (Thermofisher) and converted into inhibition percentages. For $IC_{50}$ determinations, the inhibitor was tested at 6 to 10 different concentrations, and the related inhibitions were fitted to a classical Langmuir equilibrium model using XLFIT (IDBS).

Inhibition of E. coli $C_7$ (018:K1:H7) LPS Biosynthesis:
Principle:

E. coli $C_7$ (018:K1:H7) is a Newborn Meningitidis E. coli (NMEC) strain which displays a typical LPS made of Lipid A successively branched with the inner and outer core oligosaccharides, and finally with the O-antigen repeats. The inner core contains several heptose residues. An inhibitor of the LPS heptosylation pathway should therefore reduce dramatically the size of LPS from full-length to the so-called 'Re-LPS' limited to lipid A branched with 2 Kdo residues. A simple way of monitoring LPS size and composition consists in running LPS gel electrophoresis (FIG. 1): a wild type E. coli strain displays several bands including those for full and core LPS but none for Re-LPS. On the contrary, a delta-hldE mutant defective for LPS-heptosylation biosynthesis displays only the Re-LPS band.

Bacterial Culture:

The effect of heptosylation inhibitors on E. coli LPS was assessed as described below. The compounds to be tested were prepared in deionised water/DMSO (50/50) solutions and added (25 µL) in sterile culture microtubes. The strain used in this study was E. coli $C_7$ (018:K1:H7). The bacteria were isolated on tryptic soy agar (TSA) overnight. Isolated colonies were cultured in 10 mL of Luria-Bertani medium (LB) at 37° C. up to an optical density (OD) of typically 0.15. These exponentially growing bacteria were finally diluted to 5e5 cfu/mL and added in each well (225 µL) for incubation with the compounds at 37° C. for approximately 5 hours, up to an optical density of ≈0.2-0.4. Some test compounds e.g. phospho-sugars required Glucose-6-Phosphate (G6P, from Sigma) to be added in the culture medium in order to activate their active transport into the bacterial cytosol via the phospho-sugar transporter UhpT. This was achieved by adding in the culture tube 2.5 µL of a 10 mM water solution of G6P (100 µM final concentration).

LPS Extraction:

Bacterial cultures were normalized via OD determination, pelleted and washed with 1 mL Phosphate-Buffer-Saline (PBS). The pellets were then denatured for 10 min at 95-100° C. in 50 µL of Sodium dodecyl sulphate 0.2% (SDS), beta-mercaptoethanol 1%, Glycerol 36%, Tris pH 7.4 30 mM and bromophenol blue 0.001%. Samples were cooled down to room temperature, supplemented with 1.5 µl of proteinase K at 20 mg/mL, incubated for 1 hour at 55° C. and centrifuged for min at 13,000 rpm at 25° C. The resulting supernatant, containing LPS, was finally analysed by SDS-PAGE electrophoresis.

LPS SDS-PAGE Electrophoresis:

Polyacrylamide gels (16%/4% acrylamide for separation and concentration respectively) were prepared, loaded with 8 µL of LPS extracts and migrated.

Silver Staining:

Gels were incubated overnight in 5% acetic acid/40% ethanol/deionised water, treated by 1% periodic acid/5% acetic acid for 15 min, washed 4 times for 10 min in deionised water and finally incubated for 18 min in the dark in a silver nitrate solution composed of 56 mL NaOH 0.1N, 4 mL ammoniac 33%, 45 mL AgNO3 5% (Tsai and Frasch) and 195 mL deionised water. Gels were then washed extensively in deionised water for 30 min and incubated for 10-15 min (up to LPS bands apparition) in the revelation mix composed of 300 mL deionised water, 300 µL formaldehyde 36.5% (Fluka) and 100 µL citric acid 2.3M. The revelation was stopped by incubating the gels in acetic acid 10% for 5 min. Gels were finally washed in deionised water, numerized with a Samsung PL51 camera and analysed by ImageJ software. The percentage of inhibition of LPS heptosylation was defined as the relative area of the Re-LPS band compared to the cumulated areas of Re-LPS and Core-LPS bands.

Inhibitory Activities of Selected Compounds:

Compounds described in examples 5, 6, 10, 11 and 15 display $IC_{50}$ values between 500 nM and 100 µM on GmhA of E. coli.

Compounds described in examples 1-4, 7-9 and 12-14 display $IC_{50}$ values <500 nM on GmhA of E. coli.

Compounds described in examples 2, 4, 7-9, 12, 13 display in the presence of 100 µM G6P at least 50% inhibition of E. coli C7 LPS heptosylation at concentrations <1 mM.

Data of inhibitory activities of some example compounds are presented in the table:

| Compound | $IC_{50}$ GmhA E. coli | $EC_{50}$ of E. coli C7 LPS heptosylation inhibition |
| --- | --- | --- |
| Example 2 | 2.4 nM | 18 µM |
| Example 3 | 3 nM | 18 µM |
| Example 7 | 46 nM | 220 µM |
| Example 8 | 27 nM | 180 µM |
| Example 9 | 15 nM | 76 µM |

Combination with Antibiotics on E. coli $C_7$ (018:K1:H7):

The compound to be tested was diluted in 50 mM HEPES buffer pH 7.4 from 10 mM stock solution. 5 µL of compound dilution or buffer were distributed in a sterile clear round bottom 96-well polystyrene microplate (Corning). 5 μL of serial 2-fold dilutions of reference antibiotics (Erythromycin (Fluka), Rifampicin (Fluka), or Synercid® (Monarch Pharmaceuticals)) in DMSO were added. An exponentially growing preculture of *E. coli* $C_7$ (O18:K1:H7) in LB was diluted to 1e4 cfu/mL and supplemented with 100 μM G6P, and 90 μL of this suspension were added to the microplates. After overnight incubation at 37° C., the minimal inhibitory concentration (MIC) of the antibiotics were determined for each test compound concentration, as the lowest antibiotic concentration for which no bacterial pellet is visible without magnification.

Activity of Selected Compound in Combination with Antibiotics on *E. coli* C7:

Compound described in example 2 displays in the presence of 100 μM G6P a 32-fold potentiation of erythromycin (MIC from 32 to 1 μg/mL), and a 16-fold potentiation of rifampicin (MIC from 4 to 0.25 μg/mL) and Synercid® (MIC from 128 to 8 μg/mL) at concentrations <1 mM.

We provide here novel compounds active on a LPS heptosylation target while also demonstrating their ability to reach and inhibit this target in the cytosol of clinically relevant Gram-negative bacteria.

Data obtained on bacteria lacking heptoses show that such compounds have the potential to induce a high sensitivity of Gram-negative bacteria to the host complement or to detergents and hydrophobic antibiotics. They have therefore the potential to prevent or inhibit bacterial infection alone or in combination with an antibiotic, antivirulent or immunostimulating drug (Annu. Rev. Biochem. 2002, 635). Such inhibitors provide a novel way to treat or prevent bloodstream infections caused by pathogenic Gram negative bacteria, without affecting the commensal flora and with less selective pressure than conventional antibacterial agents.

The invention claimed is:
1. The compounds having the general formula (I)

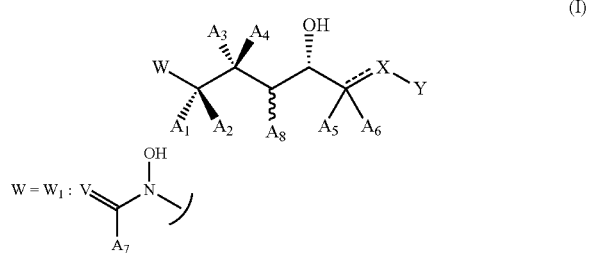

wherein,
$A_1$ and $A_2$, identical or different, are H, $(C_1-C_6)$alkyl, $(C_1-C_6)$fluoroalkyl, $(C_2-C_6)$alkenyl, $(C_2-C_6)$alkynyl, $(C_1-C_6)$alkyl-$OR_a$, $(C_1-C_6)$alkyl-$SR_a$, $(C_1-C_6)$alkyl-$NR_aR_b$, $OR_a$, $SR_a$, $NR_aR_b$, or $COR_a$;
$A_3$ is H, OH or form a carbonyl with $A_4$;
$A_4$ is H, OH or form a carbonyl with $A_3$;
$A_5$ is H, $CR_aR_bOH$, F, OH or forms a double bond with X in the case where X is CH;
$A_6$ is H or F;
X is $CH_2$, CHF, $CF_2$, CHOH, O, or a simple bond, or X is CH in the case where $A_5$ forms with X a double bond;
Y is $P(O)(OR_a)(OR_b)$ or $P(O)(OR_a)(NR_aR_b)$;
V is O;
$A_7$ is H, $(C_1-C_6)$alkyl, $(C_1-C_6)$fluoroalkyl, $(C_2-C_6)$alkenyl, $(C_2-C_6)$alkynyl or $(C_1-C_6)$alkyl-$OR_a$;
As is OH or H;
$R_a$ and $R_b$, identical or different, are selected from the group consisting of H, $(C_1-C_6)$alkyl, $(C_1-C_6)$fluoroalkyl, $(C_1-C_6)$alkyl-OH and $(C_1-C_6)$alkyl-O—$(C_1-C_6)$alkyl; in the form of pure diastereoisomers and mixtures of diastereoisomers, as well as the cyclic hemiketal or cyclic hemiacetal forms for compounds bearing carbonyl and hydroxyl groups, and their addition salts thereof with acids and bases.

2. The compounds of formula (I) and their addition salts thereof with acids and bases, according to claim 1, wherein Y is $P(O)(OH)_2$.

3. The compounds of general formula (I) and pharmaceutically acceptable addition salts thereof with acids and bases as defined in claim 2, for use as drugs.

4. The compounds of formula (I) and their addition salts thereof with acids and bases, according to claim 1, wherein X is $CH_2$, CHF, $CF_2$, CHOH or O.

5. The compounds of formula (I) and their addition salts thereof with acids and bases, according to claim 1, wherein $A_1$ and $A_2$ are H or one of them is H and the other is $(C_1-C_6)$alkyl or one of them is H and the other is fluoro($C_1$-$C_6$)alkyl or one of them is H and the other is $(C_1-C_6)$alkyl-$OR_a$ or one of them is H and the other is $(C_1-C_6)$alkyl-$SR_a$ or one of them is H and the other is $COR_a$, $R_a$ being as defined in claim 1, or one of them is H and the other is OH.

6. The compounds of formula (I) and their addition salts thereof with acids and bases, according to claim 1, wherein when $A_3$ forms a carbonyl with $A_4$, As is OH or $CR_aR_bOH$, $R_a$ and $R_b$ being as defined in claim 1, and when $A_3$ doesn't form a carbonyl with $A_4$, As is H or F.

7. The compounds of formula (I) and their addition salts thereof with acids and bases, according to claim 1, wherein $A_7$ is H or $(C_1-C_6)$alkyl.

8. The compounds of formula (I) according to claim 1 which names follow:
N-hydroxy-N-formylamino-1-deoxy-D-ribitol-5-phosphate, [6-(Formyl-hydroxy-amino)-(3R,4R,5S)-3,4,5-trihydroxy-hexyl]-phosphonic acid, [[6-(Formyl-hydroxy-amino)-(3R,4R,5S)-1,3,4,5-tetra-hydroxy-hexyl]-phosphonic acid, [(2S,3S,4S)-5-(Formyl-hydroxy-amino)-2,3,4-trihydroxy-pentyl]-phosphonic acid (1-(N-benzyloxy-N-formylamino)-1,5-dideoxy-D-ribitol] 5-phosphonic acid), 1-(N-benzyloxy-N-formylamino)-1-deoxy-5,6-dihydroxy-D-ribo-hexitol)]-6-phosphonic acid, [(3R,4R,5S)-6-(Formyl-hydroxy-amino)-3,4,5,7-tetrahydroxy-heptyl]-phosphonic acid (diastereoisomers DIA1 and DIA2), [1-Fluoro-6-(formyl-hydroxy-amino)-(3R,4R,5S)-3,4,5-trihydroxy-hexyl]-phosphonic acid, (3R,4S,5R)-3,4,5-trihydroxy-6-(N-hydroxyformamido) hexyl)phosphonic acid, (3R,4R,5R)-3,4,5-trihydroxy-6-(N-hydroxyformamido)-hexylphosphonic acid, [1,1-Difluoro-6-(formyl-hydroxy-amino)-(3R,4R,5S)-3,4,5-trihydroxy-hexyl]-phosphonic acid, [1-(N-hydroxy-N-formylamino)-1,6-dideoxy-D-allo/L-talo-hexitol)] 6-phosphonic acid, 1-(N-benzyloxy-N-formylamino)-1-deoxy-D-ribo-5-(E)-hexenitol 6-phosphonic acid and their addition salts thereof with acids and bases, in particular their sodium salts.

9. The compounds of general formula (I) and pharmaceutically acceptable addition salts thereof with acids and bases, as defined in claim 8, for use as drugs.

10. The compounds of general formula (I) and pharmaceutically acceptable addition salts thereof with acids and bases as defined in claim 1, for use as drugs.

11. The compounds of general formula (I) and pharmaceutically acceptable addition salts thereof with acids and bases as defined in claim 1 for use as drugs for the therapeutical treatment of infections due to Gram-negative bacteria in human or animals.

12. The compounds of general formula (I) and pharmaceutically acceptable addition salts thereof with acids and bases, as defined in claim 1, for use as drugs in combination with an antibacterial, an antivirulence agent, a drug reinforcing the host innate immunity or a combination of any of them.

13. The compounds of general formula (I) and pharmaceutically acceptable addition salts thereof with acids and bases, as defined in claim 1, for use as drugs in combination with macrolides, streptogramins, pleuromutilins, FabI inhibitors, rifamycins, lipopeptides, GM-CSF or a combination of any of them.

14. Pharmaceutical compositions containing as active principle a compound of general formula (I) or a pharmaceutically acceptable addition salt thereof with an acid or a base, as defined in claim 1.

15. Mixture or pharmaceutical association comprising as active principles a compound of formula (I) or a pharmaceutically acceptable addition salt thereof with an acid or a base, as defined in claim 1, and an antibacterial, an antivirulence agent, a drug reinforcing the host innate immunity or a combination of any of them.

16. Mixture or pharmaceutical association comprising as active principles a compound of formula (I) or a pharmaceutically acceptable addition salt thereof with an acid or a base, as defined in claim 1, and a macrolide, a streptogramin, a pleuromutilin, a FabI inhibitor, a rifamycin, a lipopeptide, a GM-CSF or a combination of any of them.

* * * * *